US006720142B1

(12) United States Patent
Hall

(10) Patent No.: US 6,720,142 B1
(45) Date of Patent: Apr. 13, 2004

(54) METHOD OF DETERMINING EVOLUTIONARY POTENTIAL OF MUTANT RESISTANCE GENES AND USE THEREOF TO SCREEN FOR DRUG EFFICACY

(75) Inventor: Barry G. Hall, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 09/640,882

(22) Filed: Aug. 18, 2000

Related U.S. Application Data

(60) Provisional application No. 60/149,813, filed on Aug. 19, 1999.

(51) Int. Cl.[7] ............................................. C12Q 1/68
(52) U.S. Cl. ..................................... 435/6; 435/440
(58) Field of Search ................................. 435/6, 440

(56) References Cited

U.S. PATENT DOCUMENTS

| | | | | | |
|---|---|---|---|---|---|
| 5,605,793 | A | * | 2/1997 | Stemmer ........................ | 435/6 |
| 5,766,842 | A | * | 6/1998 | Melnick et al. ................ | 435/5 |
| 6,063,562 | A | | 5/2000 | Melnick et al. ................ | 435/5 |
| 6,130,036 | A | * | 10/2000 | Loeb et al. ..................... | 435/5 |
| 2001/0014444 | A1 | * | 8/2001 | Melnick et al. ................ | 435/4 |
| 2001/0044101 | A1 | * | 11/2001 | Melnick et al. ................ | 435/6 |

FOREIGN PATENT DOCUMENTS

WO    WO 96/08580    3/1996

OTHER PUBLICATIONS

Sirawaraporn et al., "Antifolate–Resistant Mutants of *Plasmodium falciparum* Dihydrofolate Reductase," *Proc. Natl. Acad. Sci. USA* 94:1124–1129 (1997).
Crameri et al., "Molecular Evolution of an Arsenate Detoxification Pathway by DNA Shuffling," *Nature Biotechnology* 15:436–438 (1997).
Stanssens et al. "Efficient Oligonucleotide–Directed Construction of Mutations in Expression Vectors by the Gapped Duplex DNA Method Using Alternating Selectable Markers," *Nucleic Acids Research* 17(12):4441–4454 (1989).
Vakulenko et al., "Selection and Charaterization of β–Lactam–β–Lactamase Inactivator Resistant Mutants Following PCR , Mutagenesis of the TEM–1 β–Lactamase Gene," *Antimicrobial Agents and Chemotherapy* 42(7):1542–1548 (1998).
Vaillancourt et al., "The HIV Type 1 Protease Inhibitor Saquinavir Can Select for Multiple Mutations that Confer Increasing Resistance," *AIDS Research and Human Retroviruses* 15(4):355–363 (1999).

Crameri et al., "DNA Shuffling of a Family of Genes from Diverse Species Accelerates Directed Evolution," *Nature* 391:288–291 (1998).
Canica et al., "Phenotypic Study of Resistance of β–Lactamase–Inhibitor–Resistant TEM Enzymes Which Differ by Naturally Occurring Variations and by Site–Directed Substitution at $Asp^{276}$," *Antimicrobial Agents and Chemotherapy* 42(6):1323–1328 (1998).
Reetz et al., "Superior Biocatalysts by Directed Evolution," *Topics in Current Chemistry* 200:31–57 (1999).
Hall, "Experimental Evolution of Ebg Enzyme Provides Clues About the Evolution of Catalysis and to Evolutionary Potential," *FEMS Microbiology Letters* 174:1–8 (1999).
Hall, "Toward an Understanding of Evolutionary Potential," *FEMS Microbiology Letters* 178:1–6 (1999).
Zhao et al., "Optimization of DNA Shuffling for High Fidelity Recombination," *Nucleic Acids Research* 25(6):1307–1308 (1997).
Zhao et al., "Functional and Nonfunctional Mutations Distinguished by Random Recombination of Homologous Genes," *Proc. Natl. Acad. Sci. USA* 94:7997–8000 (1997).
Zhang et al., "Directed Evolution of a Fucosidase from a Galactosidase by DNA Shuffling and Screening," *Proc. Natl. Acad. Sci. USA* 94:4504–4509 (1997).
Yano et al., "Directed Evolution of an Aspartate Aminotransferase with New Substrate Specificities," *Proc. Natl. Acad. Sci. USA* 95:5511–5515 (1998).
Harayama, "Artificial Evolution by DNA Shuffling," *Tibtech* 16:76–82 (1998).
Stemmer, "Rapid Evolution of a Protein In Vitro by DNA Shuffling," *Nature* 370(4):389–391 (1994).
Christians et al., "Directed Evolution of Thymidine Kinase for AZT Phosphorylation Using DNA Family Shuffling," *Nature Biotechnology* 17:259–264 (1999).

* cited by examiner

*Primary Examiner*—Kenneth R. Horlick
(74) *Attorney, Agent, or Firm*—Nixon Peabody LLP

(57) ABSTRACT

The present invention relates to a method of predicting the evolutionary potential of a mutant resistance gene, which is carried out by providing a host cell which includes a mutant resistance gene either including two or more nucleic acid modifications or encoding a mutant polypeptide including two or more amino acid modifications, wherein the mutant resistance gene or mutant polypeptide confers a selectable advantage to the host cell, and then determining whether the mutant resistance gene is likely to evolve through two or more independent mutation events. Also disclosed are the resulting mutant resistance genes and their encoded polypeptides, and methods of using such mutant resistance genes to screen a drug for anti-pathogenic activity against a pathogen and assessing the potential longevity of a candidate anti-pathogenic drug.

41 Claims, 15 Drawing Sheets

```
   1 CGTATGGCAA TGAAAGACGG TGAGCTGGTG ATATGGGATA GTGTTCACCC TTGTTACACC
  61 GTTTTCCATG AGCAAACTGA AACGTTTTCA TCGCTCTGGA GTGAATACCA CGACGATTTC
 121 CGGCAGTTTC TACACATATA TTCGCAAGAT GTGGCGTGTT ACGGTGAAAA CCTGGCCTAT
 181 TTCCCTAAAG GGTTTATTGA GAATATGTTT TTCGTCTCAG CCAATCCCTG GGTGAGTTTC
 241 ACCAGTTTTG ATTTAAACGT GGCCATCATG TTTGACAGCT TATCATCGAC TGCACGGTGC
 301 ACCAATGCTT CTGGCGTCAG GCAGCCATCG GAAGCTGTGG TATGGCTGTG CAGGTCGTAA
 361 ATCACTGCAT AATTCGTGTC GCTCAAGGCG CACTCCCGTT CTGGATAATG TTTTTTGCGC
 421 CGACATCATA ACGGTTCTGG CAAATATTCT GAAATGAGCT GTTGACAATT AATCATCCGG
 481 CTCGTATAAT GTGTGGAATT GTGAGCGGAT AACAATTTCA CACAGGAAAC AGACCATGGC
 541 TGGTGACCAC GTCGTGGAAT GCCTTCGAAT TCAGCACCTG CACATGGGAC GTCGACCTGA
 601 GGTAATTATA ACCCGGGCCC TATATATGGA TCCAATTGCA ATGATCATCA TGACAGATCT
 661 GCGCGCGATC GATATCAGCG CTTTAAATTT GCGCATGCTA GCTATAGTTC TAGAGGTACC
 721 GGTTGTTAAC GTTAGCCGGC TACGTATACT CCGGAATATT AATAGGCCTA GGATGCATAT
 781 GGCGGCCGCC TGCAGCTGGC GCCATCGATA CGCGTACGTC GCGACCGCGG ACATGTACAG
 841 AGCTCGAGAA GTACTAGTGG CCAGGACCCA ACGCTGCCCG AGATGCGCCG CGTGCGGCTG
 901 CTGGAGATGG CGGACGCGAT GGATATGTTC TGCCAAGGGT TGGTTTGCGC ATTCACAGTT
 961 CTCCGCAAGA ATTGATTGGC TCCAATTCTT GGAGTGGTGA ATCCGTTAGC GAGGTGCCGC
1021 CGGCTTCCAT TCAGGTCGAG GTGGCCCGGC TCCATGCACC GCGACGCAAC GCGGGGAGGC
1081 AGACAAGGTA TAGGGCGGCG CCTACAATCC ATGCCAACCC GTTCCATGTG CTCGCCGAGG
1141 CGGCATAAAT CGCCGTGACG ATCAGCGGTC CAGTGATCGA AGTTAGGCTG GTAAGAGCCG
1201 CGAGCGATCC TTGAAGCTGT CCCTGATGGT CGTCATCTAC CTGCCTGGAC AGCATGGCCT
1261 GCAACGCGGG CATCCCGATG CCGCCGGAAG CGAGAAGAAT CATAATGGGG AAGGCCATCC
1321 AGCCTCGCGT CGCGAACGCC AGCAAGACGT AGCCCAGCGC GTCGGCCGCC ATGCCGGCGA
1381 TAATGGCCTG CTTCTCGCCG AAACGTTTGG TGGCGGGACC AGTGACGAAG GCTTGAGCGA
1441 GGGCGTGCAA GATTCCGAAT ACCGCAAGCG ACAGGCCGAT CATCGTCGCG CTCCAGCGAA
1501 AGCGGTCCTC GCCGAAAATG ACCCAGAGCG CTGCCGGCAC CTGTCCTACG AGTTGCATGA
1561 TAAAGAAGAC AGTCATAAGT GCGGCGACGA TAGTCATGCC CCGCGCCCAC CGGAAGGAGC
1621 TGACTGGGTT GAAGGCTCTC AAGGGCATCG GTCGACGCTC TCCCTTATGC GACTCCTGCA
1681 TTAGGAAGCA GCCCAGTAGT AGGTTGAGGC CGTTGAGCAC CGCCGCCGCA AGGAATGGTG
1741 CATGCAAGGA GATGGCGCCC AACAGTCCCC CGGCCACGGG CCTGCCACC ATACCCACGC
1801 CGAAACAAGC GCTCATGAGC CCGAAGTGGC GAGCCCGATC TTCCCCATCG GTGATGTCGG
1861 CGATATAGGC GCCAGCAACC GCACCTGTGG CGCCGGTGAT GCCGGCCACG ATGCGTCCGG
1921 CGTAGAGGAT CCACAGGACG GGTGTGGTCG CCATGATCGC GTAGTCGATA GTGGCTCCAA
1981 GTAGCGAAGC GAGCAGGACT GGGCGGCGGC CAAAGCGGTC GGACAGTGCT CCGAGAACGG
2041 GTGCGCATAG AAATTGCATC AACGCATATA GCGCTAGCAG CACGCCATAG TGACTGGCGA
2101 TGCTGTCGGA ATGGACGATA TCCCGCAAGA GGCCCGGCAG TACCGGCATA ACCAAGCCTA
2161 TGCCTACAGC ATCCAGGGTG ACGGTGCCGA GGATGACGAT GAGCGCATTG TTAGATTTCA
2221 TACACGGTGC CTGACTGCGT TAGCAATTTA ACTGTGATAA ACTACCGCAT TAAAGCTTAT
2281 CGATGATAAG CTGTCAAACA TGAGAATTAC AACTTATATC GTATGGGGCT GACTTCAGGT
2341 GCTACATTTG AAGAGATAAA TTGCACTGAA ATCTAGAAAT ATTTTATCTG ATTAATAAGA
2401 TGATCTTCTT GAGATCGTTT TGGTCTGCGC GTAATCTCTT GCTCTGAAAA CGAAAAAACC
2461 GCCTTGCAGG GCGGTTTTTC GAAGGTTCTC TGAGCTACCA ACTCTTTGAA CCGAGGTAAC
2521 TGGCTTGGAG GAGCGCAGTC ACCAAAACTT GTCCTTTCAG TTTAGCCTTA ACCGGCGCAT
2581 GACTTCAAGA CTAACTCCTC TAAATCAATT ACCAGTGGCT GCTGCCAGTG GTGCTTTTGC
2641 ATGTCTTTCC GGGTTGGACT CAAGACGATA GTTACCGGAT AAGGCGCAGC GGTCGGACTG
2701 AACGGGGGGT TCGTGCATAC AGTCCAGCTT GGAGCGAACT GCCTACCCGG AACTGAGTGT
2761 CAGGCGTGGA ATGAGACAAA CGCGGCCATA ACAGCGGAAT GACACCGGTA AACCGAAAGG
2821 CAGGAACAGG AGAGCGCACG AGGGAGCCGC CAGGGGAAA CGCCTGGTAT CTTTATAGTC
2881 CTGTCGGGTT TCGCCACCAC TGATTTGAGC GTCAGATTTC GTGATGCTTG TCAGGGGGGC
2941 GGAGCCTATG GAAAAACGGC TTTGCCGCGG CCCTCTCACT TCCCTGTTAA GTATCTTCCT
```

Figure 2A

```
3001 GGCATCTTCC AGGAAATCTC CGCCCCGTTC GTAAGCCATT TCCGCTCGCC GCAGTCGAAC
3061 GACCGAGCGT AGCGAGTCAG TGAGCGAGGA AGCGGAATAT ATCCTGTATC ACATATTCTG
3121 CTGACGCACC GGTGCAGCCT TTTTTCTCCT GCCACATGAA GCACTTCACT GACACCCTCA
3181 TCAGTGCCAA CATAGTAAGC CAGTATACAC TCCGCTAGCG CTGATGTCCG GCGGTGCTTT
3241 TGCCGTTACG CACCACCCCG TCAGTAGCTG AACAGGAGGG ACAGCTGATA GAAACAGAAG
3301 CCACTGGAGC ACCTCAAAAA CACCATCATA CACTAAATCA GTAAGTTGGC AGCATCACCC
3361 GACGCACTTT GCGCCGAATA AATACCTGTG ACGGAAGATC ACTTCGCAGA ATAAATAAAT
3421 CCTGGTGTCC CTGTTGATAC CGGGAAGCCC TGGGCCAACT TTTGGCGAAA ATGAGACGTT
3481 GATCGGCACG TAAGAGGTTC CAACTTTCAC CATAATGAAA TAAGATCACT ACCGGGCGTA
3541 TTTTTTGAGT TATCGAGATT TTCAGGAGCT AAGGAAGCTA AAATGGAGAA AAAAATCACT
3601 GGATATACCA CCGTTGATAT ATCCCAATGG CATCGTAAAG AACATTTTGA GGCATTTCAG
3661 TCAGTTGCTC AATGTACCTA TAACCAGACC GTTCAGCTGG ATATTACGGC CTTTTTAAAG
3721 ACCGTAAAGA AAAATAAGCA CAAGTTTTAT CCGGCCTTTA TTCACATTCT TGCCCGCCTG
3781 ATGAATGCTC ATCCGGAATT C
```

Figure 2B

```
   1 CGTATGGCAA TGAAAGACGG TGAGCTGGTG ATATGGGATA GTGTTCACCC TTGTTACACC
  61 GTTTTCCATG AGCAAACTGA AACGTTTTCA TCGCTCTGGA GTGAATACCA CGACGATTTC
 121 CGGCAGTTTC TACACATATA TTCGCAAGAT GTGGCGTGTT ACGGTGAAAA CCTGGCCTAT
 181 TTCCCTAAAG GGTTTATTGA GAATATGTTT TTCGTCTCAG CCAATCCCTG GGTGAGTTTC
 241 ACCAGTTTTG ATTTAAACGT GGCCATCATG TTTGACAGCT TATCATCGAC TGCACGGTGC
 301 ACCAATGCTT CTGGCGTCAG GCAGCCATCG GAAGCTGTGG TATGGCTGTG CAGGTCGTAA
 361 ATCACTGCAT AATTCGTGTC GCTCAAGGCG CACTCCCGTT CTGGATAATG TTTTTTGCGC
 421 CGACATCATA ACGGTTCTGG CAAATATTCT GAAATGAGCT GTTGACAATT AATCATCCGG
 481 CTCGTATAAT GTGTGGAATT GTGAGCGGAT AACAATTTCA CACAGGAAAC AGACCATGGC
 541 TGGTGACCAC GTCGTGGAAT GCCTTCGAAT TCAGCACCTG CACATGGGAC GTCGACCTGA
 601 GGTAATTATA ACCCGGGCCC TATATATGGA TCCAATTGCA ATGATCATCA TGACAGATCT
 661 GCGCGCGATC GATATCAGCG CTTTAAATTT GCGCATGCTA GCTATAGTTC TAGAGGTACC
 721 GGTTGTTAAC GTTAGCCGGC TACGTATACT CCGGAATATT AATAGGCCTA GGATGCATAT
 781 GGCGGCCGCC TGCAGCTGGC GCCATCGATA CGCGTACGTC GCGACCGCGG ACATGTACAG
 841 AGCTCGAGAA GTACTAGTTT ACGTTGACAC CATCGAATGG CGCAAAACCT TTCGCGGTAT
 901 GGCATGATAG CGCCCGGAAG AGAGTCAATT CAGGGTGGTG AATGTGAAAC CAGTAACGTT
 961 ATACGATGTC GCAGAGTATG CCGGTGTCTC TTATCAGACC GTTTCCCGCG TGGTGAACCA
1021 GGCCAGCCAC GTTTCTGCGA AAACGCGGGA AAAAGTGGAA GCGGCGATGG CGGAGCTGAA
1081 TTACATTCCC AACCGCGTGG CACAACAACT GGCGGGCAAA CAGTCGTTGC TGATTGGCGT
1141 TGCCACCTCC AGTCTGGCCC TGCACGCGCC GTCGCAAATT GTCGCGGCGA TTAAATCTCG
1201 CGCCGATCAA CTGGGTGCCA GCGTGGTGGT GTCGATGGTA GAACGAAGCG GCGTCGAAGC
1261 CTGTAAAGCG GCGGTGCACA ATCTTCTCGC GCAACGCGTC AGTGGGCTGA TCATTAACTA
1321 TCCGCTGGAT GACCAGGATG CCATTGCTGT GGAAGCTGCC TGCACTAATG TTCCGGCGTT
1381 ATTTCTTGAT GTCTCTGACC AGACACCCAT CAACAGTATT ATTTTCTCCC ATGAAGACGG
1441 TACGCGACTG GGCGTGGAGC ATCTGGTCGC ATTGGGTCAC CAGCAAATCG CGCTGTTAGC
1501 GGGCCCATTA AGTTCTGTCT CGGCGCGTCT GCGTCTGGCT GGCTGGCATA AATATCTCAC
1561 TCGCAATCAA ATTCAGCCGA TAGCGGAACG GGAAGGCGAC TGGAGTGCCA TGTCCGGTTT
1621 TCAACAAACC ATGCAAATGC TGAATGAGGG CATCGTTCCC ACTGCGATGC TGGTTGCCAA
1681 CGATCAGATG GCGCTGGGCG CAATGCGCGC CATTACCGAG TCCGGGCTGC GCGTTGGTGC
1741 GGATATCTCG GTAGTGGGAT ACGACGATAC CGAAGACAGC TCATGTTATA TCCCGCCGTC
1801 AACCACCATC AAACAGGATT TTCGCCTGCT GGGGCAAACC AGCGTGGACC GCTTGCTGCA
1861 ACTCTCTCAG GGCCAGGCGG TGAAGGGCAA TCAGCTGTTG CCCGTCTCAC TGGTGAAAAG
1921 AAAAACCACC CTGGCGCCCA ATACGCAAAC CGCCTCTCCC CGCGCGTTGG CCGATTCATT
1981 AATGCAGCTG GCACGACAGG TTTCCCGACT GGAAAGCGGG CAGTGAGCGC AACGCAATTA
2041 ATGTGAGTTA GCGCGAATTG ATCTGAATTC TCATGTTTGA CAGCTTATCA TCGACTGCAC
2101 GGTGCACCAA TGCTTCTGGC GTCAGGCAGC CATCGGAAGC TGTGGTATGG CTGTGCAGGT
2161 CGTAAATCAC TGCATAATTC GTGTCGCTCA AGGCGCACTC CCGTTCTGGA TAATGTTTTT
2221 TGCGCCGACA TCATAACGGT TCTGGCAAAT ATTCTAGTGG CCAGGACCCA ACGCTGCCCG
2281 AGATGCGCCG CGTGCGGCTG CTGGAGATGG CGGACGCGAT GGATATGTTC TGCCAAGGGT
2341 TGGTTTGCGC ATTCACAGTT CTCCGCAAGA ATTGATTGGC TCCAATTCTT GGAGTGGTGA
2401 ATCCGTTAGC GAGGTGCCGC CGGCTTCCAT TCAGGTCGAG GTGGCCCGGC TCCATGCACC
2461 GCGACGCAAC GCGGGGAGGC AGACAAGGTA TAGGGCGGCG CCTACAATCC ATGCCAACCC
2521 GTTCCATGTG CTCGCCGAGG CGGCATAAAT CGCCGTGACG ATCAGCGGTC CAGTGATCGA
2581 AGTTAGGCTG GTAAGAGCCG CGAGCGATCC TTGAAGCTGT CCCTGATGGT CGTCATCTAC
2641 CTGCCTGGAC AGCATGGCCT GCAACGCGGG CATCCCGATG CCGCCGGAAG CGAGAAGAAT
2701 CATAATGGGG AAGGCCATCC AGCCTCGCGT CGCAACGCC AGCAAGACGT AGCCCAGCGC
2761 GTCGGCCGCC ATGCCGGCGA TAATGGCCTG CTTCTCGCCG AAACGTTTGG TGGCGGGACC
2821 AGTGACGAAG GCTTGAGCGA GGGCGTGCAA GATTCCGAAT ACCGCAAGCG ACAGGCCGAT
2881 CATCGTCGCG CTCCAGCGAA AGCGGTCCTC GCCGAAAATG ACCCAGAGCG CTGCCGGCAC
2941 CTGTCCTACG AGTTGCATGA TAAAGAAGAC AGTCATAAGT GCGGCGACGA TAGTCATGCC
```

Figure 4A

```
3001 CCGCGCCCAC CGGAAGGAGC TGACTGGGTT GAAGGCTCTC AAGGGCATCG GTCGACGCTC
3061 TCCCTTATGC GACTCCTGCA TTAGGAAGCA GCCCAGTAGT AGGTTGAGGC CGTTGAGCAC
3121 CGCCGCCGCA AGGAATGGTG CATGCAAGGA GATGGCGCCC AACAGTCCCC CGGCCACGGG
3181 GCCTGCCACC ATACCCACGC CGAAACAAGC GCTCATGAGC CCGAAGTGGC GAGCCCGATC
3241 TTCCCCATCG GTGATGTCGG CGATATAGGC GCCAGCAACC GCACCTGTGG CGCCGGTGAT
3301 GCCGGCCACG ATGCGTCCGG CGTAGAGGAT CCACAGGACG GGTGTGGTCG CCATGATCGC
3361 GTAGTCGATA GTGGCTCCAA GTAGCGAAGC GAGCAGGACT GGGCGGCGGC CAAAGCGGTC
3421 GGACAGTGCT CCGAGAACGG GTGCGCATAG AAATTGCATC AACGCATATA GCGCTAGCAG
3481 CACGCCATAG TGACTGGCGA TGCTGTCGGA ATGGACGATA TCCCGCAAGA GGCCCGGCAG
3541 TACCGGCATA ACCAAGCCTA TGCCTACAGC ATCCAGGGTG ACGGTGCCGA GGATGACGAT
3601 GAGCGCATTG TTAGATTTCA TACACGGTGC CTGACTGCGT TAGCAATTTA ACTGTGATAA
3661 ACTACCGCAT TAAAGCTTAT CGATGATAAG CTGTCAAACA TGAGAATTAC AACTTATATC
3721 GTATGGGGCT GACTTCAGGT GCTACATTTG AAGAGATAAA TTGCACTGAA ATCTAGAAAT
3781 ATTTTATCTG ATTAATAAGA TGATCTTCTT GAGATCGTTT TGGTCTGCGC GTAATCTCTT
3841 GCTCTGAAAA CGAAAAAACC GCCTTGCAGG GCGGTTTTTC GAAGGTTCTC TGAGCTACCA
3901 ACTCTTTGAA CCGAGGTAAC TGGCTTGGAG GAGCGCAGTC ACCAAAACTT GTCCTTTCAG
3961 TTTAGCCTTA ACCGGCGCAT GACTTCAAGA CTAACTCCTC TAAATCAATT ACCAGTGGCT
4021 GCTGCCAGTG GTGCTTTTGC ATGTCTTTCC GGGTTGGACT CAAGACGATA GTTACCGGAT
4081 AAGGCGCAGC GGTCGGACTG AACGGGGGT TCGTGCATAC AGTCCAGCTT GGAGCGAACT
4141 GCCTACCCGG AACTGAGTGT CAGGCGTGGA ATGAGACAAA CGCGGCCATA ACAGCGGAAT
4201 GACACCGGTA AACCGAAAGG CAGGAACAGG AGAGCGCACG AGGGAGCCGC CAGGGGGAAA
4261 CGCCTGGTAT CTTTATAGTC CTGTCGGGTT TCGCCACCAC TGATTTGAGC GTCAGATTTC
4321 GTGATGCTTG TCAGGGGGGC GGAGCCTATG GAAAACGGC TTTGCCGCGG CCCTCTCACT
4381 TCCCTGTTAA GTATCTTCCT GGCATCTTCC AGGAAATCTC CGCCCCGTTC GTAAGCCATT
4441 TCCGCTCGCC GCAGTCGAAC GACCGAGCGT AGCGAGTCAG TGAGCGAGGA AGCGGAATAT
4501 ATCCTGTATC ACATATTCTG CTGACGCACC GGTGCAGCCT TTTTTCTCCT GCCACATGAA
4561 GCACTTCACT GACACCCTCA TCAGTGCCAA CATAGTAAGC CAGTATACAC TCCGCTAGCG
4621 CTGATGTCCG GCGGTGCTTT TGCCGTTACG CACCACCCCG TCAGTAGCTG AACAGGAGGG
4681 ACAGCTGATA GAAACAGAAG CCACTGGAGC ACCTCAAAAA CACCATCATA CACTAAATCA
4741 GTAAGTTGGC AGCATCACCC GACGCACTTT GCGCCGAATA AATACCTGTG ACGGAAGATC
4801 ACTTCGCAGA ATAAATAAAT CCTGGTGTCC CTGTTGATAC CGGGAAGCCC TGGGCCAACT
4861 TTTGGCGAAA ATGAGACGTT GATCGGCACG TAAGAGGTTC CAACTTTCAC CATAATGAAA
4921 TAAGATCACT ACCGGGCGTA TTTTTTGAGT TATCGAGATT TTCAGGAGCT AAGGAAGCTA
4981 AAATGGAGAA AAAAATCACT GGATATACCA CCGTTGATAT ATCCCAATGG CATCGTAAAG
5041 AACATTTTGA GGCATTTCAG TCAGTTGCTC AATGTACCTA TAACCAGACC GTTCAGCTGG
5101 ATATTACGGC CTTTTTAAAG ACCGTAAAGA AAAATAAGCA CAAGTTTTAT CCGGCCTTTA
5161 TTCACATTCT TGCCCGCCTG ATGAATGCTC ATCCGGAATT C
```

Figure 4B

```
   1 CGTATGGCAA TGAAAGACGG TGAGCTGGTG ATATGGGATA GTGTTCACCC TTGTTACACC
  61 GTTTTCCATG AGCAAACTGA AACGTTTTCA TCGCTCTGGA GTGAATACCA CGACGATTTC
 121 CGGCAGTTTC TACACATATA TTCGCAAGAT GTGGCGTGTT ACGGTGAAAA CCTGGCCTAT
 181 TTCCCTAAAG GGTTTATTGA GAATATGTTT TTCGTCTCAG CCAATCCCTG GGTGAGTTTC
 241 ACCAGTTTTG ATTTAAACGT GGCCATCATG TTTGACAGCT TATCATCGAC TGCACGGTGC
 301 ACCAATGCTT CTGGCGTCAG GCAGCCATCG GAAGCTGTGG TATGGCTGTG CAGGTCGTAA
 361 ATCACTGCAT AATTCGTGTC GCTCAAGGCG CACTCCCGTT CTGGATAATG TTTTTTGCGC
 421 CGACATCATA ACGGTTCTGG CAAATATTCT GAAATGAGCT GTTGACAATT AATCATCCGG
 481 CTCGTATAAT GTGTGGAATT GTGAGCGGAT AACAATTTCA CACAGGAAAC AGATCATGAC
 541 TGGTGACCAC GTCGTGGAAT GCCTTCGAAT TCAGCACCTG CACATGGGAC GTCGACCTGA
 601 GGTAATTATA ACCCGGGCCC TATATATGGA TCCAATTGCA ATGATCATCA TGTCAGATCT
 661 GCGCGCGATC GATATCAGCG CTTTAAATTT GCGCATGCTA GCTATAGTTC TAGAGGTACC
 721 GGTTGTTAAC GTTAGCCGGC TACGTATACT CCGGAATATT AATAGGCCTA GGATGCATAT
 781 GGCGGCCGCC TGCAGCTGGC GCCATCGATA CGCGTACGTC GCGACCGCGG ACATGTACAG
 841 AGCTCGAGAA GTACTAGTTT ACGTTGACAC CATCGAATGG CGCAAAACCT TTCGCGGTAT
 901 GGCATGATAG CGCCCGGAAG AGAGTCAATT CAGGGTGGTG AATGTGAAAC CAGTAACGTT
 961 ATACGATGTC GCAGAGTATG CCGGTGTCTC TTATCAGACC GTTTCCCGCG TGGTGAACCA
1021 GGCCAGCCAC GTTTCTGCGA AAACGCGGGA AAAAGTGGAA GCGGCGATGG CGGAGCTGAA
1081 TTACATTCCC AACCGCGTGG CACAACAACT GGCGGGCAAA CAGTCGTTGC TGATTGGCGT
1141 TGCCACCTCC AGTCTGGCCC TGCACGCGCC GTCGCAAATT GTCGCGGCGA TTAAATCTCG
1201 CGCCGATCAA CTGGGTGCCA GCGTGGTGGT GTCGATGGTA GAACGAAGCG GCGTCGAAGC
1261 CTGTAAAGCG GCGGTGCACA ATCTTCTCGC GCAACGCGTC AGTGGGCTGA TCATTAACTA
1321 TCCGCTGGAT GACCAGGATG CCATTGCTGT GGAAGCTGCC TGCACTAATG TTCCGGCGTT
1381 ATTTCTTGAT GTCTCTGACC AGACACCCAT CAACAGTATT ATTTCTCCC ATGAAGACGG
1441 TACGCGACTG GGCGTGGAGC ATCTGGTCGC ATTGGGTCAC CAGCAAATCG CGCTGTTAGC
1501 GGGCCCATTA AGTTCTGTCT CGGCGCGTCT GCGTCTGGCT GGCTGGCATA AATATCTCAC
1561 TCGCAATCAA ATTCAGCCGA TAGCGGAACG GGAAGGCGAC TGGAGTGCCA TGTCCGGTTT
1621 TCAACAAACC ATGCAAATGC TGAATGAGGG CATCGTTCCC ACTGCGATGC TGGTTGCCAA
1681 CGATCAGATG GCGCTGGGCG CAATGCGCGC CATTACCGAG TCCGGGCTGC GCGTTGGTGC
1741 GGATATCTCG GTAGTGGGAT ACGACGATAC CGAAGACAGC TCATGTTATA TCCCGCCGTC
1801 AACCACCATC AAACAGGATT TTCGCCTGCT GGGGCAAACC AGCGTGGACC GCTTGCTGCA
1861 ACTCTCTCAG GGCCAGGCGG TGAAGGGCAA TCAGCTGTTG CCCGTCTCAC TGGTGAAAAG
1921 AAAAACCACC CTGGCGCCCA ATACGCAAAC CGCCTCTCCC CGCGCGTTGG CCGATTCATT
1981 AATGCAGCTG GCACGACAGG TTTCCCGACT GGAAAGCGGG CAGTGAGCGC AACGCAATTA
2041 ATGTGAGTTA GCGCGAATTG ATCTGAATTC TCATGTTTGA CAGCTTATCA TCGACTGCAC
2101 GGTGCACCAA TGCTTCTGGC GTCAGGCAGC CATCGGAAGC TGTGGTATGG CTGTGCAGGT
2161 CGTAAATCAC TGCATAATTC GTGTCGCTCA AGGCGCACTC CCGTTCTGGA TAATGTTTTT
2221 TGCGCCGACA TCATAACGGT TCTGGCAAAT ATTCTAGTGG CCAGGACCCA ACGCTGCCCG
2281 AGATGCGCCG CGTGCGGCTG CTGGAGATGG CGGACGCGAT GGATATGTTC TGCCAAGGGT
2341 TGGTTTGCGC ATTCACAGTT CTCCGCAAGA ATTGATTGGC TCCAATTCTT GGAGTGGTGA
2401 ATCCGTTAGC GAGGTGCCGC CGGCTTCCAT TCAGGTCGAG GTGGCCCGGC TCCATGCACC
2461 GCGACGCAAC GCGGGGAGGC AGACAAGGTA TAGGGCGGCG CCTACAATCC ATGCCAACCC
2521 GTTCCATGTG CTCGCCGAGG CGGCATAAAT CGCCGTGACG ATCAGCGGTC CAGTGATCGA
2581 AGTTAGGCTG GTAAGAGCCG CGAGCGATCC TTGAAGCTGT CCCTGATGGT CGTCATCTAC
2641 CTGCCTGGAC AGCATGGCCT GCAACGCGGG CATCCCGATG CCGCCGGAAG CGAGAAGAAT
2701 CATAATGGGG AAGGCCATCC AGCCTCGCGT CGCAACGCC AGCAAGACGT AGCCCAGCGC
2761 GTCGGCCGCC ATGCCGGCGA TAATGGCCTG CTTCTCGCCG AAACGTTTGG TGGCGGGACC
2821 AGTGACGAAG GCTTGAGCGA GGGCGTGCAA GATTCCGAAT ACCGCAAGCG ACAGGCCGAT
2881 CATCGTCGCG CTCCAGCGAA AGCGGTCCTC GCCGAAAATG ACCCAGAGCG CTGCCGGCAC
2941 CTGTCCTACG AGTTGCATGA TAAAGAAGAC AGTCATAAGT GCGGCGACGA TAGTCATGCC
```

Figure 5A

```
3001 CCGCGCCCAC CGGAAGGAGC TGACTGGGTT GAAGGCTCTC AAGGGCATCG GTCGACGCTC
3061 TCCCTTATGC GACTCCTGCA TTAGGAAGCA GCCCAGTAGT AGGTTGAGGC CGTTGAGCAC
3121 CGCCGCCGCA AGGAATGGTG CATGCAAGGA GATGGCGCCC AACAGTCCCC CGGCCACGGG
3181 GCCTGCCACC ATACCCACGC CGAAACAAGC GCTCATGTGC CCGAAGTGGC GAGCCCGATC
3241 TTCCCCATCG GTGATGTCGG CGATATAGGC GCCAGCAACC GCACCTGTGG CGCCGGTGAT
3301 GCCGGCCACG ATGCGTCCGG CGTAGAGGAT CCACAGGACG GGTGTGGTCG CCATGATCGC
3361 GTAGTCGATA GTGGCTCCAA GTAGCGAAGC GAGCAGGACT GGGCGGCGGC CAAAGCGGTC
3421 GGACAGTGCT CCGAGAACGG GTGCGCATAG AAATTGCATC AACGCATATA GCGCTAGCAG
3481 CACGCCATAG TGACTGGCGA TGCTGTCGGA ATGGACGATA TCCCGCAAGA GGCCCGGCAG
3541 TACCGGCATA ACCAAGCCTA TGCCTACAGC ATCCAGGGTG ACGGTGCCGA GGATGACGAT
3601 GAGCGCATTG TTAGATTTCA TACACGGTGC CTGACTGCGT TAGCAATTTA ACTGTGATAA
3661 ACTACCGCAT TAAAGCTTAT CGATGATAAG CTGTCAAACA TGAGAATTAC AACTTATATC
3721 GTATGGGGCT GACTTCAGGT GCTACATTTG AAGAGATAAA TTGCACTGAA ATCTAGAAAT
3781 ATTTTATCTG ATTAATAAGA TGATCTTCTT GAGATCGTTT TGGTCTGCGC GTAATCTCTT
3841 GCTCTGAAAA CGAAAAAACC GCCTTGCAGG GCGGTTTTTC GAAGGTTCTC TGAGCTACCA
3901 ACTCTTTGAA CCGAGGTAAC TGGCTTGGAG GAGCGCAGTC ACCAAAACTT GTCCTTTCAG
3961 TTTAGCCTTA ACCGGCGCAT GACTTCAAGA CTAACTCCTC TAAATCAATT ACCAGTGGCT
4021 GCTGCCAGTG GTGCTTTTGC ATGTCTTTCC GGGTTGGACT CAAGACGATA GTTACCGGAT
4081 AAGGCGCAGC GGTCGGACTG AACGGGGGGT TCGTGCATAC AGTCCAGCTT GGAGCGAACT
4141 GCCTACCCGG AACTGAGTGT CAGGCGTGGA ATGAGACAAA CGCGGCCATA ACAGCGGAAT
4201 GACACCGGTA AACCGAAAGG CAGGAACAGG AGAGCGCACG AGGGAGCCGC CAGGGGGAAA
4261 CGCCTGGTAT CTTTATAGTC CTGTCGGGTT TCGCCACCAC TGATTTGAGC GTCAGATTTC
4321 GTGATGCTTG TCAGGGGGGC GGAGCCTATG GAAAACGGC TTTGCCGCGG CCCTCTCACT
4381 TCCCTGTTAA GTATCTTCCT GGCATCTTCC AGGAAATCTC CGCCCCGTTC GTAAGCCATT
4441 TCCGCTCGCC GCAGTCGAAC GACCGAGCGT AGCGAGTCAG TGAGCGAGGA AGCGGAATAT
4501 ATCCTGTATC ACATATTCTG CTGACGCACC GGTGCAGCCT TTTTTCTCCT GCCACATGAA
4561 GCACTTCACT GACACCCTCA TCAGTGCCAA CATAGTAAGC CAGTATACAC TCCGCTAGCG
4621 CTGATGTCCG GCGGTGCTTT TGCCGTTACG CACCACCCCG TCAGTAGCTG AACAGGAGGG
4681 ACAGCTGATA GAAACAGAAG CCACTGGAGC ACCTCAAAAA CACCATCATA CACTAAATCA
4741 GTAAGTTGGC AGCATCACCC GACGCACTTT GCGCCGAATA AATACCTGTG ACGGAAGATC
4801 ACTTCGCAGA ATAAATAAAT CCTGGTGTCC CTGTTGATAC CGGGAAGCCC TGGGCCAACT
4861 TTTGGCGAAA ATGAGACGTT GATCGGCACG TAAGAGGTTC CAACTTTCAC CATAATGAAA
4921 TAAGATCACT ACCGGGCGTA TTTTTTGAGT TATCGAGATT TTCAGGAGCT AAGGAAGCTA
4981 AAATGGAGAA AAAAATCACT GGATATACCA CCGTTGATAT ATCCCAATGG CATCGTAAAG
5041 AACATTTTGA GGCATTTCAG TCAGTTGCTC AATGTACCTA TAACCAGACC GTTCAGCTGG
5101 ATATTACGGC CTTTTTAAAG ACCGTAAAGA AAAATAAGCA CAAGTTTTAT CCGGCCTTTA
5161 TTCACATTCT TGCCCGCCTG ATGAATGCTC ATCCGGAATT C
```

Figure 5B

```
wild-type  ATGGTCAAAA CGACGCTCTG CGCCTTATTA ATTACCGCCT CTTGCTCCAC ATTTGCTGCC   60
AmpC13A    .......... .......... ....C..... .......... .......... ..........
AmpC41A    .......... .......... ....C..... .......... .......... ..........
AmpC21B    .......... .......... .......... .......... .......... ..........

wild-type  CCTCAACAAA TCAACGATAT TGTGCATCGC ACAATTACCC CGCTTATAGA GCAACAAAAG  120
AmpC13A    .......... .......... .......... .......... .......... ..........
AmpC41A    .......... .......... .......... .......... .......... ..........
AmpC21B    .......... .......... .......... .......... .......... ..........

wild-type  ATCCCGGGTA TGGCGGTGGC GGTAATTTAT CAGGGTAAAC CTTATTACTT TACCTGGGGC  180
AmpC13A    .......... .......... .......... .......... .......... ..........
AmpC41A    .......... .......... .......... .......... .......... ..........
AmpC21B    .......... .......... .......... .......... .......... ..........

wild-type  TATGCGGACA TCGCCAAAAA GCAGCCCGTC ACACAGCAAA CGTTGTTTGA GTTAGGTTCG  240
AmpC13A    .......... ....T..... .......... .......... .......... ..........
AmpC41A    .......... ....T..... .......... .......... .......... ..........
AmpC21B    .......... .......... .......... .......... .......... ..........

wild-type  GTCAGCAAAA CATTTACTGG CGTGCTTGGT GGCGACGCTA TTGCTCGAGG GGAAATCAAG  300
AmpC13A    .......... .......... .......... .......... .......... ..........
AmpC41A    .......... .......... .......... .......... .......... ..........
AmpC21B    .......... .......... .......... .......... .......... ..........

wild-type  TTAAGCGATC CCACAACAAA ATACTGGCCT GAACTTACCG CTAAACAGTG GAATGGGATC  360
AmpC13A    .......... .......... .......... .......... .......... ..........
AmpC41A    .......... .......... .......... .......... .......... ..........
AmpC21B    .......... .......... .......... .......... .......... ..........

wild-type  ACACTATTAC ATCTCGCAAC CTACACTGCT GGCGGCCTGC CATTGCAGGT GCCGGATGAG  420
AmpC13A    .......... .......... .......... .......... .......... ..........
AmpC41A    T......... .......... .......... .......... .......... ..........
AmpC21B    .......... .......... .......... .......... .......... ..........

wild-type  GTGAAATCCT CAAGCGACTT GCTGCGCTTC TATCAAAACT GGCAGCCTGC ATGGGCTCCA  480
AmpC13A    .......... .......... .......... .......... .......... ..........
AmpC41A    .......... .......... .......... .......... .......... ..........
AmpC21B    .......... .......... .......... .......... .......... ..........

wild-type  GGAACACAAC GTCTGTATGC CAACTCCAGT ATCGGTTTGT TCGGCGCACT GGCTGTGAAG  540
AmpC13A    .......... .......... .......... .......... .......... ..........
AmpC41A    .......... .......... .......... .......... .......... ..........
AmpC21B    .......... .......... .......... .......... .......... ..........

wild-type  CCGTCTGGTT TGAGTTTTGA GCAGGCGATG CAAACTCGTG TCTTCCAGCC ACTCAAACTC  600
AmpC13A    .......... .......... .......... .......... .......... ..........
AmpC41A    .......... .......... .......... .......... .......... ..........
AmpC21B    .......... .......... .......... .......... ......G... ..........

wild-type  AACCATACGT GGATTAATGT ACCGCCCGCA GAAGAAAAGA ATTACGCCTG GGGATATCGC  660
AmpC13A    .......... .......... .......... .......... .......... ..........
AmpC41A    .......... .......... .......... .......... .......... ..........
AmpC21B    .......... .......... .......... .......... .......... ..........
```

Figure 8A

```
wild-type  GAAGGTAAGG CAGTGCATGT TTCGCCTGGG GCGTTAGATG CTGAAGCTTA TGGTGTGAAG   720
AmpC13A    .......... .......... .......... .......... .......... ..........
AmpC41A    ..G....... .......... .......... .......... .......... ..........
AmpC21B    .......... .......... .......... .......... .C........ ..........

wild-type  TCGACCATTG AAGATATGGC CCGCTGGGTG CAAAGCAATT TAAAACCCCT TGATATCAAT   780
AmpC13A    .......... .......... .......... .......... .......... ..........
AmpC41A    .......... .......... .......... .......... .......... ..........
AmpC21B    .......... .......... .......... .......... .......... ..........

wild-type  GAGAAAACGC TTCAACAAGG GATACAACTG GCACAATCTC GCTACTGGCA AACCGGCGAT   840
AmpC13A    .......... .......... .......... .......... .......... ..........
AmpC41A    .......... .......... .......... .......... .......... ..........
AmpC21B    .......... .......... .......... .......... .......... ..........

wild-type  ATGTATCAGG GCCTGGGCTG GGAAATGCTG GACTGGCCGG TAAATCCTGA CAGCATCATT   900
AmpC13A    .......... .......... .......... .......... .......... ..........
AmpC41A    .......... .......... .......... .......... .......... ..........
AmpC21B    .......... .......... ........G. .......... ...G...... ..........

wild-type  AACGGCAGTG ACAATAAAAT TGCACTGGCA GCACGCCCCG TAAAAGCGAT TACGCCCCCA   960
AmpC13A    ......C... .......... .......... .......... .......... ..........
AmpC41A    ......C... .......... .......... .......... .......... ..........
AmpC21B    .......... .......... .......... .......... .......... ..........

wild-type  ACTCCTGCAG TACGCGCATC ATGGGTACAT AAAACAGGGG CGACCGGCGG ATTTGGTAGC  1020
AmpC13A    .......... .......... .......... .......... .......... ..........
AmpC41A    .......... .......... .......... .......... .......... ..........
AmpC21B    .......... .......... .......... .......... .......... ..........

wild-type  TATGTCGCGT TTATTCCAGA AAAAGAGCTG GGTATCGTGA TGCTGGCAAA CAAAAACTAT  1080
AmpC13A    .......... .......... .......... .......... .......... ..........
AmpC41A    .......... .......... .......... .......... .......... ..........
AmpC21B    .......... .......... .......... .......... .......... ..........

wild-type  CCCAATCCAG CGAGAGTCGA CGCCGCCTGG CAGATTCTTA ACGCTCTACA GTAA         1134
AmpC13A    .......... .......... .......... .......... .......... ....
AmpC41A    .......... .......... .......... .......... ....C..... ....
AmpC21B    .......... .......... .......... .......... .......... ....
```

Figure 8B

```
wild-type  MVKTTLCALL ITASCSTFAA PQQINDIVHR TITPLIEQQK IPGMAVAVIY QGKPYYFTWG   60
AmpC13A    .......... .......... .......... .......... .......... ..........
AmpC41A    .......... .......... .......... .......... .......... ..........
AmpC21B    .......... .......... .......... .......... .......... ..........

wild-type  YADIAKKQPV TQQTLFELGS VSKTFTGVLG GDAIARGEIK LSDPTTKYWP ELTAKQWNGI  120
AmpC13A    .......... .......... .......... .......... .......... ..........
AmpC41A    .......... .......... .......... .......... .......... ..........
AmpC21B    .......... .......... .......... .......... .......... ..........

wild-type  TLLHLATYTA GGLPLQVPDE VKSSSDLLRF YQNWQPAWAP GTQRLYANSS IGLFGALAVK  180
AmpC13A    .......... .......... .......... .......... .......... ..........
AmpC41A    S......... .......... .......... .......... .......... ..........
AmpC21B    .......... .......... .......... .......... .......... ..........

wild-type  PSGLSFEQAM QTRVFQPLKL NHTWINVPPA EEKNYAWGYR EGKAVHVSPG ALDAEAYGVK  240
AmpC13A    .......... .......... .......... .......... .......... ..........
AmpC41A    .......... .......... .......... .......... .......... ..........
AmpC21B    .......... .....R.... .......... .......... .......... ..........

wild-type  STIEDMARWV QSNLKPLDIN EKTLQQGIQL AQSRYWQTGD MYQGLGWEML DWPVNPDSII  300
AmpC13A    .......... .......... .......... .......... .......... ..........
AmpC41A    .......... .......... .......... .......... .......... ..........
AmpC21B    .......... .......... .......... .......... ........R. ....S.....

wild-type  NGSDNKIALA ARPVKAITPP TPAVRASWVH KTGATGGFGS YVAFIPEKEL GIVMLANKNY  360
AmpC13A    ..R....... .......... .......... .......... .......... ..........
AmpC41A    ..R....... .......... .......... .......... .......... ..........
AmpC21B    .......... .......... .......... .......... .......... ..........

wild-type  PNPARVDAAW QILNALQ*                                                377
AmpC13A    .......... ........
AmpC41A    .......... ........
AmpC21B    .......... ........
```

Figure 9

METHOD OF DETERMINING EVOLUTIONARY POTENTIAL OF MUTANT RESISTANCE GENES AND USE THEREOF TO SCREEN FOR DRUG EFFICACY

The present application claims benefit of U.S. Provisional Patent Application Serial No. 60/149,813 filed Aug. 19, 1999, which is hereby incorporated by reference in its entirety.

This invention was made in part through funding by the National Institutes of Health, Grant No. 1 RO1 GM59092-01. The U.S. government may have certain rights in this invention.

FIELD OF THE INVENTION

The present invention relates to a method of predicting the evolutionary potential of a mutant resistance gene, the resulting mutant resistant genes and their expression products, as well as a method of screening a candidate drug for activity against a pathogen including a mutant resistance gene and a method of assessing the potential longevity of a candidate drug.

BACKGROUND OF THE INVENTION

Antibiotics have proven to be one of medicine's most effective tools in combating disease, but their utility is constantly being challenged by the emergence of antibiotic-resistant target organisms and their future effectiveness is now in doubt. Because of their efficiency, specificity, and general absence of toxicity, β-lactam antibiotics account for about 50% of global antibiotic consumption (Livermore, "Are all beta-lactams Created Equal?" *Scand. J. Infecl. Dis. SuDDI.* 101: 33–43 (1996); Matagne et al., "Catalytic Properties of Class A beta-lactamases: Efficiency and Diversity," *Biochem. J.* 330:581–598 (1998)). Since the clinical introduction of benzylpenicillin about 50 years ago the efficiency of β-lactams has been continuously challenged by the emergence of resistant pathogens. As a result new molecules have been progressively introduced with modifications that are increasingly different from the original penicillin (Matagne et al., "Catalytic Properties of Class A beta-lactamases: Efficiency and Diversity," *Biochem. J.* 330:581-598 (1998)). Genes for resistance to β-lactams are typically plasmid-borne and encode enzymes, called β-lactamases, that degrade and inactivate β-lactam antibiotics. Among plasmid-borne resistance genes the TEM-1 β-lactamase is the most prevalent, accounting for 75% of the β-lactamase in Gram negative organisms worldwide (Amyes, "Genes and Spectrum: The Theoretical Limits," *Clin. Infect. Dis.* 27 Suppl 1:S21–28 (1998)). The success of TEM-1 β-lactamase and its relatives SHV-1, TEM-2 and OXA-1 is partly the result of its location on plasmids with insertion elements that permitted very rapid dissemination of the β-lactamase genes, and partly the result of continued evolution of the enzyme itself in response to the introduction of new drugs, particularly the cephalosporins and extended-spectrum β-lactams known as third generation cephalosporins.

Another group of β-lactamases, the Class C β-lactamases, are generally quite active toward cephalosporins, including the third generation derivatives, but have not been taken as a serious threat until recently, because the genes for Class C β-lactamases are typically located on chromosomes rather than on plasmids. The chromosomal ampC genes are found in a variety of Gram negative bacteria, including both the Enterobacteriaceae and Pseudomonas species. The ampC genes are typically expressed at a low level, as in *E. coli,* or are inducible by penicillins and early generation cephalosporins but not inducible by third and fourth generation cephalosporins. Over the last decade, however, it has been found that Gram negative pathogens that are hyper-producers of ampC β-lactamases are resistant to all but a few of the most recently introduced β-lactam antibiotics (Livermore, "Are all beta-lactams Created Equal?" *Scand. J. Infect. Dis. Suppl.* 101: 33–43 (1996)). By now 25–50% of Enterobacter isolates from ICU patients in many major Western and Far Eastern hospitals are AmpC hyper-producers and are resistant to all penicillins and cephalosporins except imipenem, meropenem, and temicillin (Livermore, "Are all beta-lactams Created Equal?" *Scand. J. Infect. Dis. Suppl.* 101: 33–43 (1996)). Even more worrying are several recent reports of derepressed ampC genes located on plasmids found in pathogenic Gram negative bacteria (Bauernfeind et al., "Characterization of the Plasmidic beta-lactamase CMY-2, which is Responsible for Cepharnycin Resistance," *Antimicrob. Agents Chemother.* 40:221–224 (1996); Horii et al., "Characterization of a Plasmid-borne and Constitutively Expressed blaMOX-1 Gene Encoding AmpC-type beta-lactamase," *Gene* 139:93–98 (1994); Jacoby et al., "More Extended-spectrum beta-lactamases," *Antimicrob. Agents Chemother.* 35:1697–1704 (1991); Papanicolaou et al., "Novel Plasmid-mediated beta-lactamase (MIR-1) Conferring Resistance to Oxyimino- and alpha-methoxy beta-lactams in Clinical Isolates of *Klebsiella pneumoniae,*" *Antimicrob. Agents Chemother.* 34:2200–2209 (1990)). Although Aymes ("Genes and Spectrum: The Theoretical Limits," *Clin. Infect. Dis.* 27 Suppl 1:S21–28 (1998)) suggests that AmpC β-lactamases at present do not seem efficient enough to cause widespread clinical problems, others (Lindberg et al., "Contribution of Chromosomal beta-lactamases to beta-lactam Resistance in Enterobacteria," *Rev. Infect. Dis.* 8 Suppl 3:S292–304 (1986); Morosini et al., "An Extended-spectrum AmpC-type beta-lactamase Obtained by in vitro Antibiotic Selection," *FEMS Microbiol. Lett.* 165:85–90 (1998); Pitout et al., "Antimicrobial Resistance with Focus on beta-lactam Resistance in Gram-negative Bacilli," *Am. J. Med.* 103:51–59 (1997)) are quite concerned that the AmpC β-lactamases constitute a pool from which clinically significant resistant strains may well emerge. That concern is exacerbated by the finding that in a clinical isolate of *Enterobacter cloacae* the AmpC β-lactamase has extended its substrate range to include the oxyimino β-lactams as the result of a tandem duplication of three amino acids (Nukaga et al., "Molecular Evolution of a Class C beta-lactamase Extending its Substrate Specificity," *J. Biol. Chem.* 270:5729–5735 (1995)). More recently, Morosini and his colleagues (Morosini et al., "An Extended-spectrum AmpC-type beta-lactamase Obtained by in vitro Antibiotic Selection," *FEMS Microbiol. Lett.* 165:85–90 (1998)) applied direct selection to isolate a mutant of an *Enterobacter cloacae* AmpC β-lactamase in which the activity toward a fourth generation cephalosporin had increased 267 fold as the result of a single amino acid replacement. Together, the fact that mutations to hyper-expression of AmpC occur readily and the facts that hyper-expressed ampC β-lactamases already confer resistance to penicillins and third generation cephalosporins, are moving onto plasmids, and can easily mutate to significant activity against fourth generation cephalosporins suggest that AmpC β-lactamases may very well constitute a potentially serious clinical threat.

Similar development of resistance can be seen in other antibiotic resistance genes such as the katG, rpoB, and rpsL genes of *Mycobacterium tuberculosis* which have resulted in multi drug resistance to isoniazid, rifampicin and streptomycin (C.D.C., "Outbreak of Multidrug-resistant Tuberculosis—Texas, California, and Pennsylvania," *MMWR* 39:369–372 (1990); C.D.C., "Nosocomial Transmission of Multidrug-resistant Tuberculosis Among HIV-infected Persons—Florida and New York 1988–1991," *MMWR* 40:585–591 (1991); C.D.C., "Transmission of Multidrug-resistant Tuberculosis from an HEV-positive Client in a Residential Substance Abuse Treatment Facility—Michigan," *MMWR* 40:129–131 (1991)); adaptive virus resistance to antiviral agents as seen, for example, with HIV-encoded protease resistance to the protease inhibitors saquinavir, ritonavir, and indinavir (Condra et al., "In vivo Emergence of HIV-1 Variants Resistant to Multiple Protease Inhibitors," *Nature* 374:569–571 (1995)); antifungal resistance genes such as the atrc multiple drug resistance gene of *Aspergillus nidulans* (U.S. Pat. No. 6,060,264 to Skatrud et al.) and pdr1 multidrug resistance gene of *Saccharomyces cerevisiae* (Balzi et al., "Me Multidrug Resistance Gene pdr1 from *Saccharomyces cerevisiae*," *J. Biol. Chem.* 262 (35):16871–16879 (1987)); and the antimalarial resistance genes such as the pfmdrl gene of *Plasmodium falciparum* (Ruetz et al., "The pfmdrl Gene of *Plasmodium falciparum* Confers Cellular Resistance to Antimalarial Drugs in Yeast Cells," *Proc. Natl. Acad. Sci. USA* 93:9942–9947 (1996)).

One problem with conventional drug development strategies is that the pharmaceutical industry responds to a newly-emerged resistant strain by developing a modified version of the drug that was previously effective against the predecessor strain. Thus, the speed with which new drugs can be developed is limited by the fact that design of a new generation of a drug cannot begin until resistance has emerged and the properties of the resistant strains are known. In view of the limitations of a reactive strategy for conventional drug development, it would be more desirable to take a proactive approach for drug development. Hence, it would be very valuable to be able to predict the properties of resistant strains that will inevitably emerge and to begin designing the next generation of drugs in anticipation of that emergence.

The present invention is directed to overcoming these and other deficiencies in the relevant art.

SUMMARY OF THE INVENTION

One aspect of the present invention relates to a method of predicting the evolutionary potential of a mutant resistance gene. This method is carried out by providing a host cell which includes a mutant resistance gene either including two or more nucleic acid modifications or encoding a mutant polypeptide including two or more amino acid modifications, wherein the mutant resistance gene or mutant polypeptide confers a selectable advantage to the host cell, and then determining whether the mutant resistance gene is likely to evolve through two or more independent mutation events.

A further aspect of the present invention relates to a method of screening a drug for anti-pathogenic activity against a pathogen including a mutant anti-pathogenic resistance gene. This method is carried out by providing a host cell which includes a mutant anti-pathogenic resistance gene either including two or more nucleic acid modifications or encoding a mutant anti-pathogenic polypeptide which includes two or more amino acid modifications, wherein the mutant anti-pathogenic resistance gene or mutant anti-pathogenic polypeptide confers a selectable advantage to the host cell; growing the host cell on a selection media comprising a candidate drug or combinations thereof; and then determining whether the host cell is capable of growing on the selection media, wherein absence of host cell growth or proliferation indicates anti-pathogenic activity for the candidate drug or combinations thereof.

Yet another aspect of the present invention relates to a method of assessing the potential longevity of a candidate anti-pathogenic drug. This method is carried out by providing a resistance gene encoding a polypeptide which is ineffective against a candidate anti-pathogenic drug; introducing multiple mutations into the resistance gene to produce a mutant resistance gene which encodes a mutant polypeptide including two or more amino acid modifications, wherein the mutant polypeptide is effective against the candidate anti-pathogenic drug; and then determining the minimum number of mutations required to overcome the activity of the candidate anti-pathogenic drug, wherein the greater the minimum number of mutations, the greater the potential longevity of the candidate anti-pathogenic drug.

A still further aspect of the present invention relates to a mutant resistance gene prepared according to the process which is carried out by providing a resistance gene; introducing a plurality of mutations into the resistance gene to produce a mutant resistance gene which encodes a mutant polypeptide including at least two amino acid modifications, the mutant polypeptide conferring enhanced resistance to host cells including the mutant resistance gene; and then determining whether the mutant protein or polypeptide is likely to evolve through independent mutations.

Such mutant resistance genes include a coding sequence which includes a plurality of mutations, the mutant resistance gene encoding a mutant protein or polypeptide (i) including at least two amino acid modifications, (ii) conferring enhanced resistance to a host cell which expresses the mutant protein or polypeptide, and (iii) being likely to evolve through independent mutations.

Another aspect of the present invention relates to a mutant resistance-conferring protein or polypeptide derived from a resistance-conferring protein or polypeptide, the mutant resistance-conferring protein or polypeptide including at least two amino acid modifications relative to the resistance-conferring protein or polypeptide and being likely to evolve through independent mutations.

The present invention is directed primarily to the development of mutant resistance genes which exhibit increased resistance to conventional drug treatments. For example, with respect to an existing antibiotic resistance gene, such a gene is first mutated in accordance with the present invention to prepare a mutant antibiotic resistance gene that contains a plurality of mutations (i.e., either in the coding region or regulatory region) such that expression of the mutant antibiotic resistance gene confers to its host organism enhanced resistance against conventional antibiotic treatments. Once the mutant antibiotic resistance gene is obtained, it is then determined whether such a mutant antibiotic resistance gene is capable of evolving by a series of individual mutation events. This is determined by replicating discrete mutation events and then selecting for any enhanced activity (i.e., resistance) against conventional antibiotic treatments. This process is repeated by screening singly mutated antibiotic resistance genes, then doubly mutated antibiotic resistance genes, and so on, until it is determined whether the first obtained mutant antibiotic resistance gene is or is not likely to evolve under environmental selection. When it is determined that such a mutant antibiotic resistance gene or a multiply mutated antibiotic resistance gene is capable of evolving (i.e., in response to conventional antibiotics), then such a mutant resistant gene or multiply mutated resistance gene can be used to screen for next generation drugs. In this fashion, it is possible to identify next generation drugs before natural selection would allow for such drug development to occur. Moreover, it is possible to determine whether such next generation drugs are likely to provide long-lasting therapeutic treatment against organisms possessing mutant resistance genes. This determination can be made by assessing the number of discrete mutational events which would be required for an individual to overcome the effects of treatment by such a next generation drug. The greater the number of discrete mutational events which would be required to overcome the efficacy of such a drug, then the more likely that such a drug would have long&-lasting efficacy. This would enable drug manufacturers the opportunity to assess the potential profitability of one drug versus another.

BRIEF DESCRIPTION OF THE DRAWINGS

FIGS. 2A–B illustrate a nucleotide sequence of the plasmid construct pACSE (SEQ. ID. No. 1). The NcoI site at bases 534–539, the BspHI site at 648–653, and the BspHI site at bases 1813–1818 are underlined. The tetracycline resistance gene extends from bases 1032–2222.

FIGS. 4A–B illustrate a nucleotide sequence of the plasmid construct pACSE2 (SEQ. ID. No. 2). The NcoI site at bases 534–539, the BspHI site at 648–653, and the BspHI site at bases 3213–3218 are underlined. The tetracycline resistance gene extends from bases 2432–3622 and the lacI$^Q$ gene extends from bases 944–2026.

FIGS. 5A–B illustrate a nucleotide sequence of the plasmid construct pACSE3 (SEQ. ID. No. 3). Plasmid pACSE3 differs from plasmid pACSE2 of FIGS. 3 and 4A–B only by modification of several restriction sites. Specifically, base 534 was changed from C to T and base 539 was changed from G to A in order to convert the unique NcoI site to a BspHI site, while base 653 was changed from A to T to destroy the existing BspHI site and base 3218 was changed from A to T to destroy existing BspHI site. The unique BspHI site, which extends from bases 534–539, is underlined.

FIGS. 8A–B are a comparative sequence alignment of the coding sequences of a wild-type ampicillin resistance gene (SEQ. ID. No. 4) and three mutant ampicillin resistance genes prepared according to the present invention. The three mutant ampicillin resistance genes are identified as AmpC13A (SEQ. ID. No. 6), AmpC41A (SEQ. ID. No. 8), and AmpC21B (SEQ. ID. No. 10). Only differences between the various sequences are identified.

FIG. 9 is a comparative sequence alignment of the wild-type ampicillin resistance polypeptide (SEQ. ID. No. 5) and the three mutant ampicillin resistance polypeptides of AmpC13A (SEQ. ID. No. 7), AmpC41A (SEQ. ID. No. 9), and AmpC21B (SEQ. ID. No. 11). Only differences between the various sequences are identified.

DETAILED DESCRIPTION OF THE INVENTION

Figure 1:
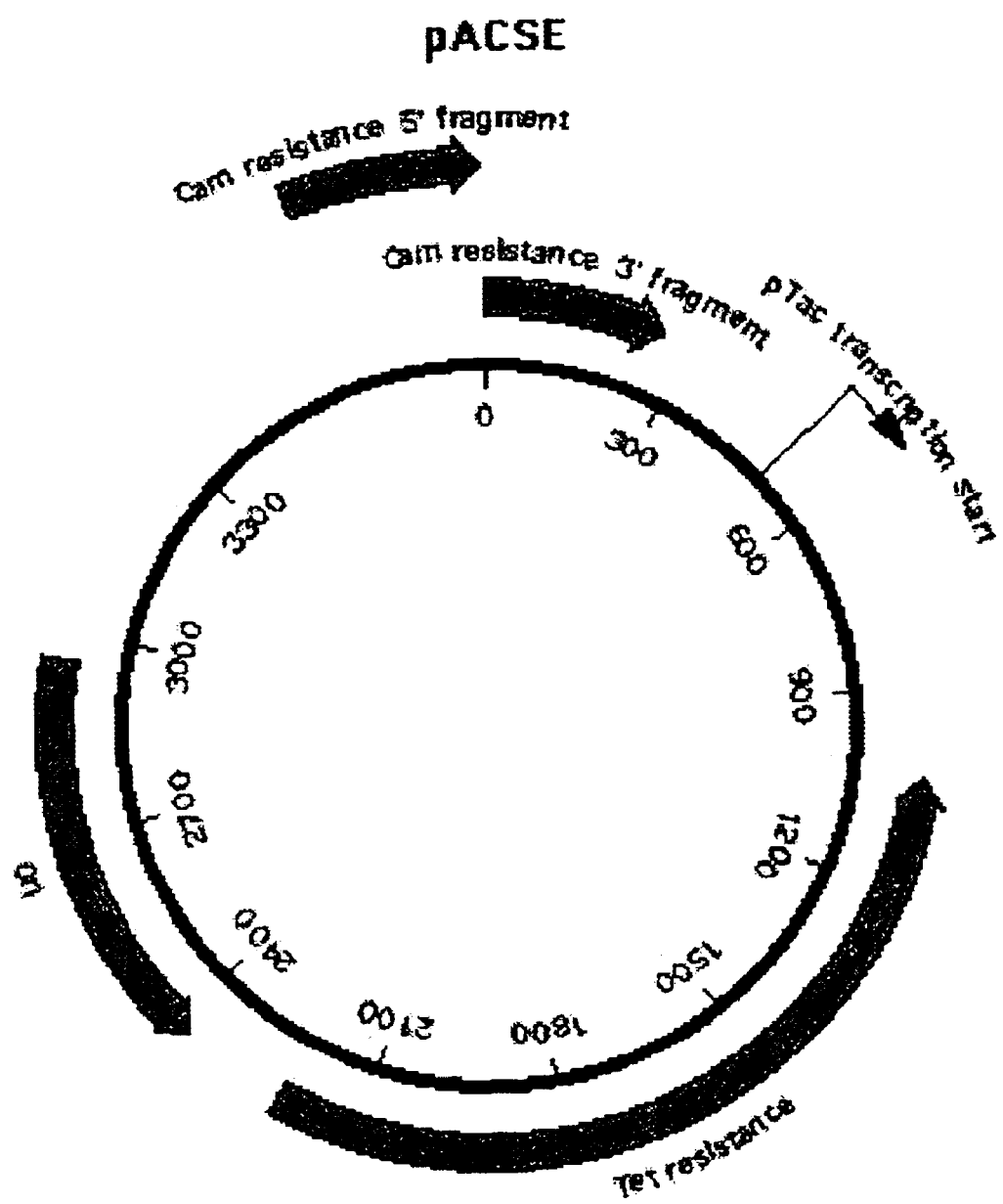
FIG. 1 is a diagram of the plasmid construct pACSE, which contains NcoI and BspHI restriction sites just downstream from the pTac transcription site. A tetracycline resistance gene is provided for selection of transformed host cells.

The present invention relates to a method of predicting the evolutionary potential of a mutant resistance gene. This method is carried out by providing a host cell which includes a mutant resistance gene either including two or more nucleic acid modifications or encoding a mutant polypeptide including two or more amino acid modifications, wherein the mutant resistance gene or mutant polypeptide confers a selectable advantage (e.g., drug resistance) to the host cell, and then determining whether the mutant resistance gene is likely to evolve through two or more independent mutation events.

By providing a mutant resistance gene, it is intended that the mutant resistance gene be developed or prepared from an existing (i.e., wild-type) resistance gene. Hence, once the wild-type resistance gene is obtained, a plurality of mutations are introduced into the wild-type resistance gene to yield a mutant resistance gene. The wild-type resistance gene and its subsequently developed mutant resistance gene can be any gene (or mutant thereof) which provides its host organism with an ability to grow and/or reproduce under conditions which would normally result in host organism death or diminished ability to grow and/or reproduce. Typically, the resistance gene affords host resistance against a drug. The drug can be any compound which disrupts host growth and/or reproduction.

The mode by which resistance can be conferred to a host organism is not important; it is merely necessary for such a gene to confer a selective advantage, such as drug resistance. For example, resistance genes can be generally assigned to five different types of resistance genes based upon the mode by which they confer resistance to their host organisms. One type of resistance gene is characterized by expression products (of the resistance gene) which destroy a therapeutic drug. Without being bound thereby, an example of this type of resistance gene is the ampicillin resistance gene of *E. coli* plasmid pBR322 (Sutcliffe, "Nucleotide Sequence of the Ampicillin Resistance Gene of *Escherichia coli* plasmid pBR322," *Proc. Natl. Acad. Sci. USA* 75:3737–3741 (1978), which is hereby incorporated by reference). A second type of resistance gene is characterized by expression products which effectively pump the drug out of the host cell such that the drug cannot effectively compromise host organism survival. Without being bound thereby, an example of this type of resistance gene is the tetA gene of plasmid RP1, which imparts resistance to tetracycline (Water et al., "The Tetracycline Resistance Determinants of RP1 and Tn1721: Nucleotide Sequence Analysis," *Nucleic Acids Rcs.* 11 (17):6089–6105 (1983), which is hereby incorporated by reference). A third type of resistance gene is characterized by expression products which modify a drug to render it ineffective (i.e., via phosphorylation, acetylation, adenylation, etc.). Without being bound thereby, an example of this type of resistance gene is the aph(32)-Ib gene of plasmid RP4 which imparts resistance to aminoglycosides (Pansegrau et al., "Nucleotide Sequence of the Kanamycin Resistance Determinant of Plasmid RP4: Homology to Other Aminoglycoside 32-Phosphotransferases," *Plasmid* 18:193–204 (1987), which is hereby incorporated by reference). A fourth type of resistance gene is characterized by expression products which mutate frequently, thereby modifying the drug target to diminish the ability of such a drug to compromise host organism survival. Without being bound thereby, an example of this type of resistance is the rapid development of variant proteases by RNA viruses, such as HIV-1 and HIV-2, which can avoid disruption by conventional protease inhibitors (Condra et al., "In vivo Emergence of HIV-1 Variants Resistant to Multiple Protease inhibitors," *Nature* 374:569–571 (1995), which is hereby incorporated by reference). A fifth type of resistance gene is characterized by overproduction of target enzymes that are no longer sensitive to the antibiotic. Without being bound thereby, examples include acquisition of a plasmid-borne dihydropteroate synthase that is not sensitive to inhibition by sulfonamides and Tn4003-borne dihydrofolate reductase that is not inhibited by trimethoprim, both of which are involved in folic acid biosynthesis. Although the two drugs are often used in combination, resistance to the drug combination is now common (Widdowson et al., "Molecular Mechanisms of Resistance to Commonly Used Non-betalactam Drugs in *Streptococcus pneumoniae*," *Semin. Respir. Infect.* 14(3):255–268 (1999), which is hereby incorporated by reference).

Regardless of the mode by which development of resistance can occur, a number of different types of resistance genes and their prepared mutant derivatives are contemplated by the present invention. Preferred resistance genes and their mutant derivatives include, without limitation, antibiotic resistance genes and mutant antibiotic resistance genes, anti-viral resistance genes and mutant anti-viral resistance genes, anti-fungal resistance genes and mutant anti-fungal resistance genes, and anti-protozoal resistance genes and mutant anti-protozoal resistance genes.

Exemplary antibiotic resistance genes include, without limitation, the katG, rpoB, and 1rpsL genes of *Mycobacterium tuberculosis* (C.D.C., "Outbreak of Multidrug-resistant Tuberculosis—Texas, California, and Pennsylvania," MMWR 39:369–372 (1990); C.D.C., "Nosocomial Transmission of Multidrug-resistant Tuberculosis Among HIV-infected Persons—Florida and New York 1988–1991," MMWR 40:585–591 (1991); C.D.C., "Transmission of Multidrug-resistant Tuberculosis from an HIV-positive Client in a Residential Substance Abuse Treatment Facility—Michigan," MMWR 40:129–131 (1991), which are hereby incorporated by reference); ampC genes of Gram negative bacteria, including both the Enterobacteriaceae and Pseudomonas species (Lindberg et al., "Contribution of Chromosomal beta-lactamases to beta-lactam Resistance in Enterobacteria," *Rev. Infect. Dis.* 8 Suppl 3:S292–304 (1986); Morosini et al., "An Extended-spectrum AmpC-type beta-lactamase Obtained by in vitro Antibiotic Selection," *FEMS Microbiol. Lett.* 165:85–90 (1998); and Pitout et al., "Antimicrobial Resistance with Focus on beta-lactam Resistance in Gram-negative Bacilli," *Am. J. Med.* 103:51–59 (1997), which are hereby incorporated by reference); TEM/SHV β-lactamases and their extended spectrum derivatives (reviewed in Jacoby, "Genetics of Extended-spectrum Beta-lactamases," *Eur. J. Clin. Microbiol. Infect. Dis.* 13 Suppl 1:S2–11 (1994), which is hereby incorporated by reference); and aminoglycoside resistance genes (reviewed in Shaw et al., "Molecular Genetics of Aminoglycoside Resistance Genes and Familial Relationships of the Aminoglycoside-modifying Enzymes," *Microbiol. Rev.* 57(1):138–163 (1993), which is hereby incorporated by reference).

Exemplary anti-viral resistance genes include, without limitation, the HIV protease gene (E1-Farrash et al., "Generation and Characterization of a Human Immunodeficiency Virus Type 1 (HIV-1) Mutant Resistant to an HIV-1 Protease Inhibitor," *J. Virol.* 68:233–239 (1994), which is hereby incorporated by reference).

Exemplary anti-fungal resistance genes include, without limitation, the atrc multiple drug resistance gene of *Aspergillus nidulans* (U.S. Pat. No. 6,060,264 to Skatrud et al., which is hereby incorporated by reference) and pdrl multidrug resistance gene of *Saccharomyces cerevisiae* (Balzi et al., "The Multidrug Resistance Gene pdrl from *Saccharomyces cerevisiae*," *J. Biol. Chem.* 262(35):16871–16879 (1987), which is hereby incorporated by reference).

Exemplary anti-protozoal resistance genes include, without limitation, the pfmdrl1 anti-malarial resistance gene of *Plasmodium falciparum* (Ruetz et al., "The pfmdr1 Gene of *Plasmodium falciparum* Confers Cellular Resistance to Antimalarial Drugs in Yeast Cells," *Proc. Nat. Acad. Sci. USA* 93:9942–9947 (1996), which is hereby incorporated by reference).

Regardless of the particular type of resistance gene which is employed, the introduction of a plurality of mutations into a resistance gene to obtain a mutant resistance gene can be performed according to any number of known processes. These include DNA shuffling, error-prone PCR, site-directed mutagenesis, cassette mutagenesis, chemical mutagenesis, or mutator strain induced mutagenesis (See Sambrook et al., *Molecular Cloning: A Laboratory Manual*, Cold Spring Harbor Laboratory, Cold Spring Harbor, N.Y. (1989); Ausubel et al., eds. *Current Protocols in Molecular Biology*, Wiley Interscience, N.Y. (1991), which are hereby incorporated by reference Of these, DNA shuffling is preferred.

DNA shuffling, also known as sexual PCR, is an in vitro method for engineering mutant DNA molecules encoding mutant proteins. DNA shuffling can be performed according to the procedures set forth in Stemmer, "Rapid Evolution of a Protein in vitro by DNA Shuffling," *Nature* 370:389–391 (1994); Stemmer, "DNA Shuffling by Random Fragmentation and Reassembly: In vitro Recombination for Molecular Evolution," *Proc. Natl. Acad. Sci. USA* 91(22): 10747–10751 (1994); and WIPO Publ. No. WO 97/20078, which are hereby incorporated by reference. Briefly, variant DNAs are generated by in vitro homologous recombination via random fragmentation of a parent DNA, followed by re-assembly using PCR, resulting in randomly introduced point mutations. The result of DNA shuffling is a pool of variant sequences that average about 7 mutations per kb of DNA. Once the resulting DNA variants have been cloned into a plasmid or other expression vector and then inserted into host cells, variants exhibiting desired activity can be selected. With an average of 6–7 mutations most genes encode non-functional products, but a powerful selective system can detect and recover those rare variants with the desired improved activity. The process can be repeated in multiple rounds using the selected variants from the previous round of DNA shuffling as the starting point for a subsequent round. Much success in increasing the activity of a target polypeptide has been achieved using DNA shuffling, such as a 32,000 fold increase in activity of TEM-1 β-lactamase (Stemmer, "Rapid Evolution of a Protein in vitro by DNA Shuffling," *Nature* 370:389–391 (1994), which is hereby incorporated by reference), a $10^5$ fold increase in activity of aspartate amino transferase for β-branched amino acids (Yano et al., "Directed Evolution of an Aspartate Aminotransferase with New Substrate Specificities," *Proc. Nat. Acad. Sci. USA* 95:5511–5515 (1998), which is hereby incorporated by reference), and a 1000-fold increase in the fucosidase activity of lacZ β-galactosidase (Zhang et al., "Directed Evolution of a Fucosidase from a Galactosidase by DNA Shuffling and Screening," *Proc. Natl. Acad. Sci. USA* 94:4504–4509 (1997), which is hereby incorporated by reference).

Error-prone PCR is another in vitro method for engineering mutant DNA molecules encoding mutant proteins. This method can be carried out according to the procedures set forth in Leung et al., *Technique* 1:11–15 (1989); and Caldwell and Joyce, *PCR Methods Applic.* 2:28–33 (1992), which are hereby incorporated by reference. Basically, PCR is performed under conditions where the copying fidelity of the DNA polymerase is low, such that a high rate of point mutations is obtained along the entire length of the PCR.

Another in vitro method for engineering mutant DNA molecules encoding mutant proteins is termed cassette mutagenesis, which can be performed according to the procedures set forth in Wells et al., "Cassette Mutagenesis: An Efficient Method for Generation of Multiple Mutations at Defined Sites," *Gene* 34(2–3):315–323 (1985); Crameri et al., "Combinatorial Multiple Cassette Mutagenesis Creates All the Permutations of Mutant and Wild-Type Sequences," *Biotechniques* 18(2):194–196 (1995), which are hereby incorporated by reference. Basically, a plasmid containing the target gene (which is to be mutated) is provided with a unique restriction site on either side of a region which is to be mutated. (Such restriction sites can be generated using site-directed mutagenesis per the procedures set forth in, e.g., Zoller et al., *DNA* 3(6):479–488 (1984), and Reidhaar-Olson et al., *Science* 241:53–57 (1988), which are hereby incorporated by reference.) The plasmid is cut at the restriction sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette, which is designed to have 3' and 5' ends that are compatible with the ends of the linearized plasmid, such that it can be directly ligated to the plasmid. The resulting plasmid contains the mutated target gene sequence.

Basically, the resistance gene can be mutated in one of two ways to enhance the resistance of a host organism (i.e., host cell) against a drug. According to one approach, the resistance gene is mutated in its regulatory regions (e.g., promoter region) to achieve a different level of expression of its encoded product, thereby imparting altered resistance levels against a drug. According to another approach, the resistance gene is mutated in its coding region to achieve expression of a mutant polypeptide which is responsible for imparting altered resistance levels against a drug. Alternatively, both types of mutations can also occur simultaneously.

The mutations which can be introduced into the nucleotide sequence of the mutant resistance gene or the amino acid sequence of the mutant polypeptide include, without limitation, additions, deletions, substitutions, duplications, and rearrangements.

Once obtained, the mutant resistance gene can be inserted into a host cell and screened for its activity (i.e., whether it confers increased resistance to its host). Insertion into the host cell can be carried out by ligating the mutant resistance gene into an expression vector (e.g., plasmid) and then treating the host cell under conditions effective to incorporate the expression vector into the host cell.

Suitable host cells include, but are not limited to, bacteria, virus, yeast, mammalian, insect, plant, and the like. Of these, prokaryotic host cells are preferred, more particularly bacterial host cells, e.g., *Escherichia coli*. Specifically, *E. coli* strains DH5α-E and JM109 have been used in practice of the present invention, although any other prokaryote or eukaryote cells could be used. DH5α-E is particularly useful for the selection phase of DNA shuffling experiments, because it transforms about ten times more efficiently than strain JM109. Increased transformation permits screening an increased number of variants in each experiment. JM109, however, is a preferred strain for use in screening the efficacy of the resistance genes.

When a prokaryotic host cell is selected for subsequent transformation, the promoter region used to construct the recombinant DNA molecule (i.e., transgene) should be appropriate for the particular host. The DNA sequences of eukaryotic promoters, as described infra for expression in eukaryotic host cells, differ from those of prokaryotic promoters. Eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference.

Promoters vary in their "strength" (i.e., their ability to promote transcription). For the purposes of expressing a cloned gene, it is desirable to use strong promoters in order to obtain a high level of transcription and, hence, expression kD of the gene. Depending upon the host cell system utilized, any one of a number of suitable promoters may be used. For instance, when cloning in *E. coli*, its bacteriophages, or plasmids, promoters such as the T7 phage promoter, lac promoter, lrp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacL5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno ("SD") sequence about 7–9 bases 5' to the initiation codon ("ATG") to provide a ribosome binding site. Thus, any SD-ATG combination that can be utilized by host cell ribosomes may be employed. Such combinations include, but are not limited to, the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Figure 3:
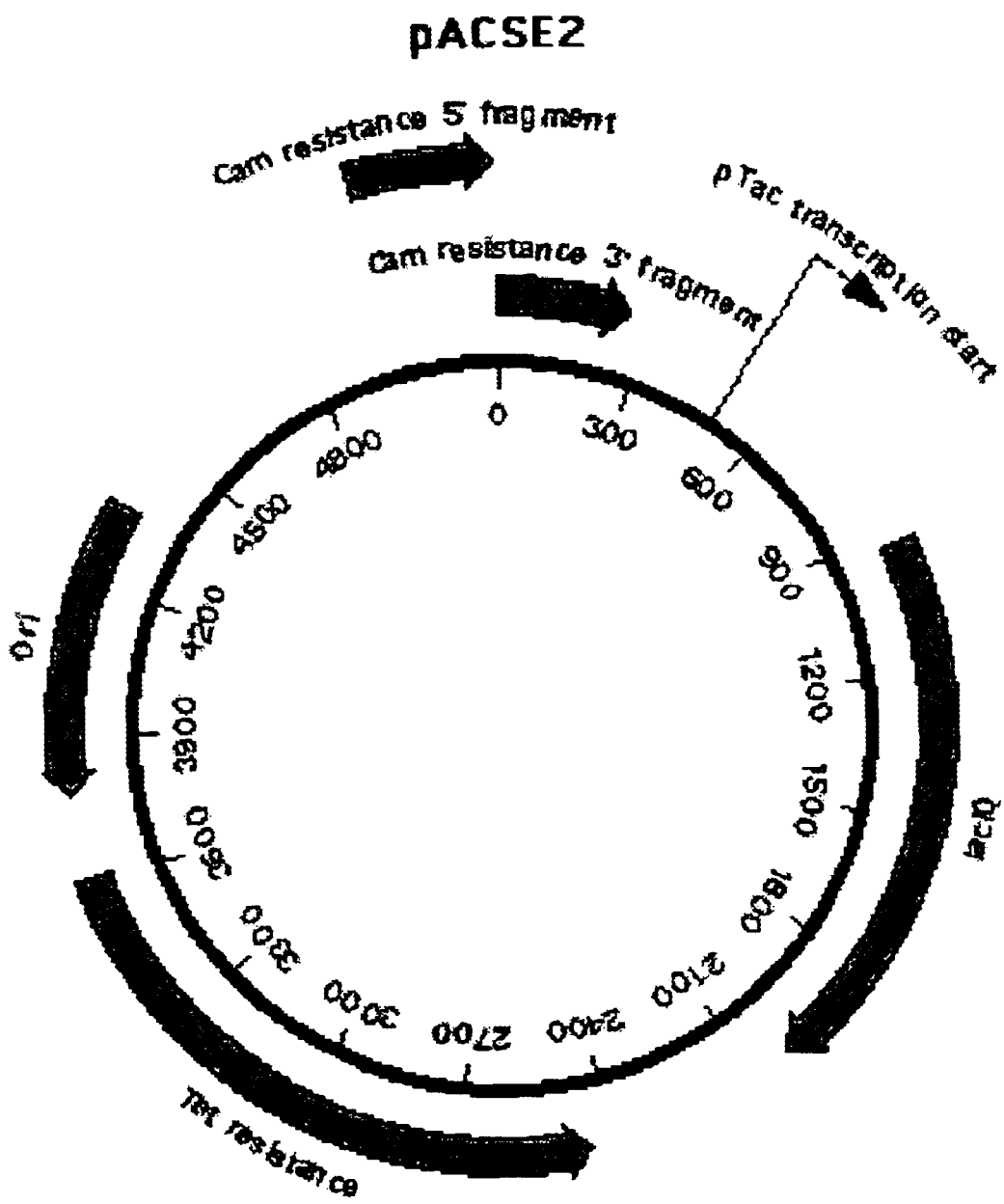
FIG. 3 is a diagram of the plasmid pACSE2, which differs from pACSE of FIG. 1 by the inclusion of the lacI$^Q$ gene.
Figure 6:
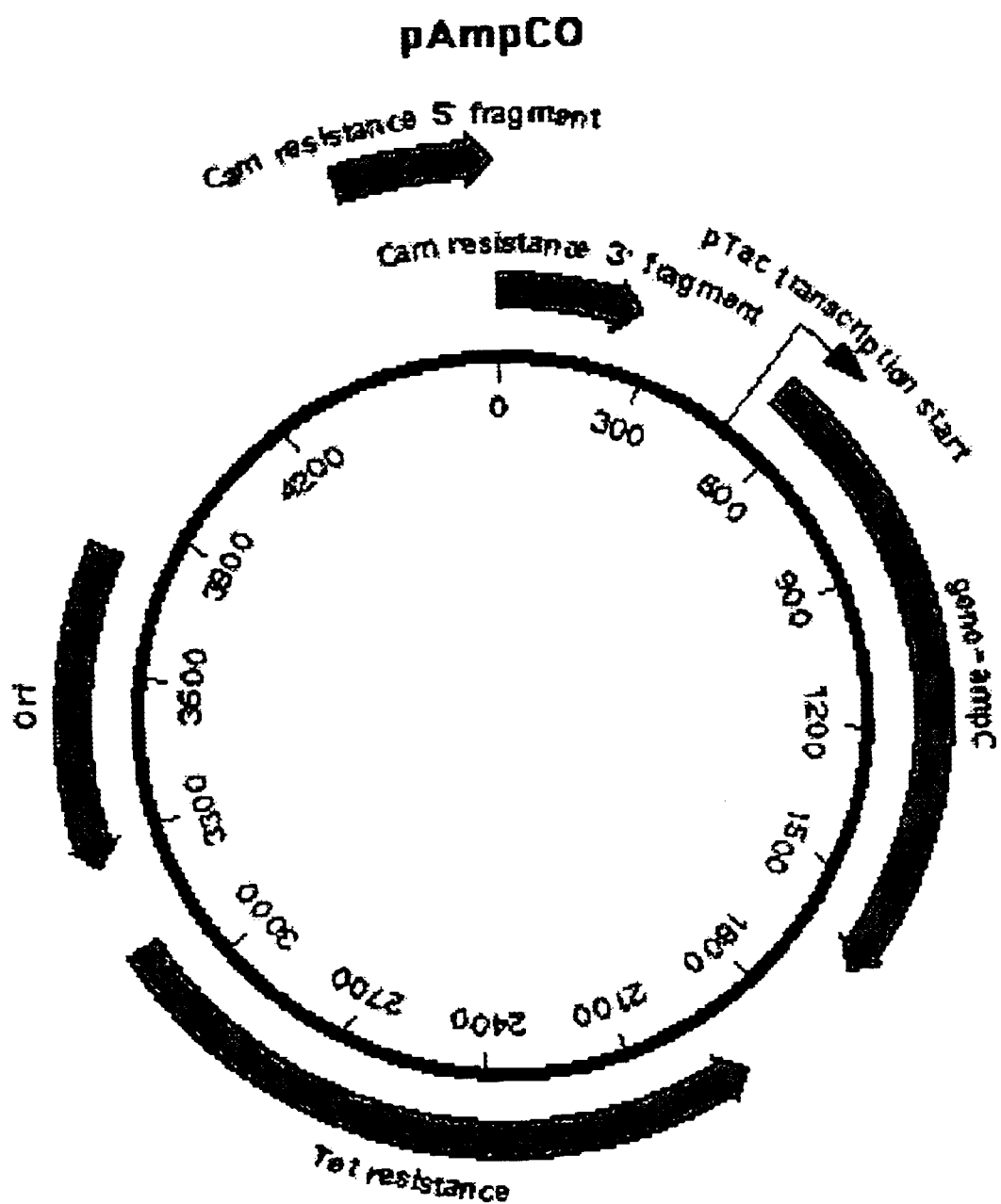
FIG. 6 is a diagram of plasmid pAmpC0, which is a pACSE plasmid containing the polypeptide coding sequence (SEQ. ID. No. 4) of a wild-type ampicillin resistance gene.
Figure 7:
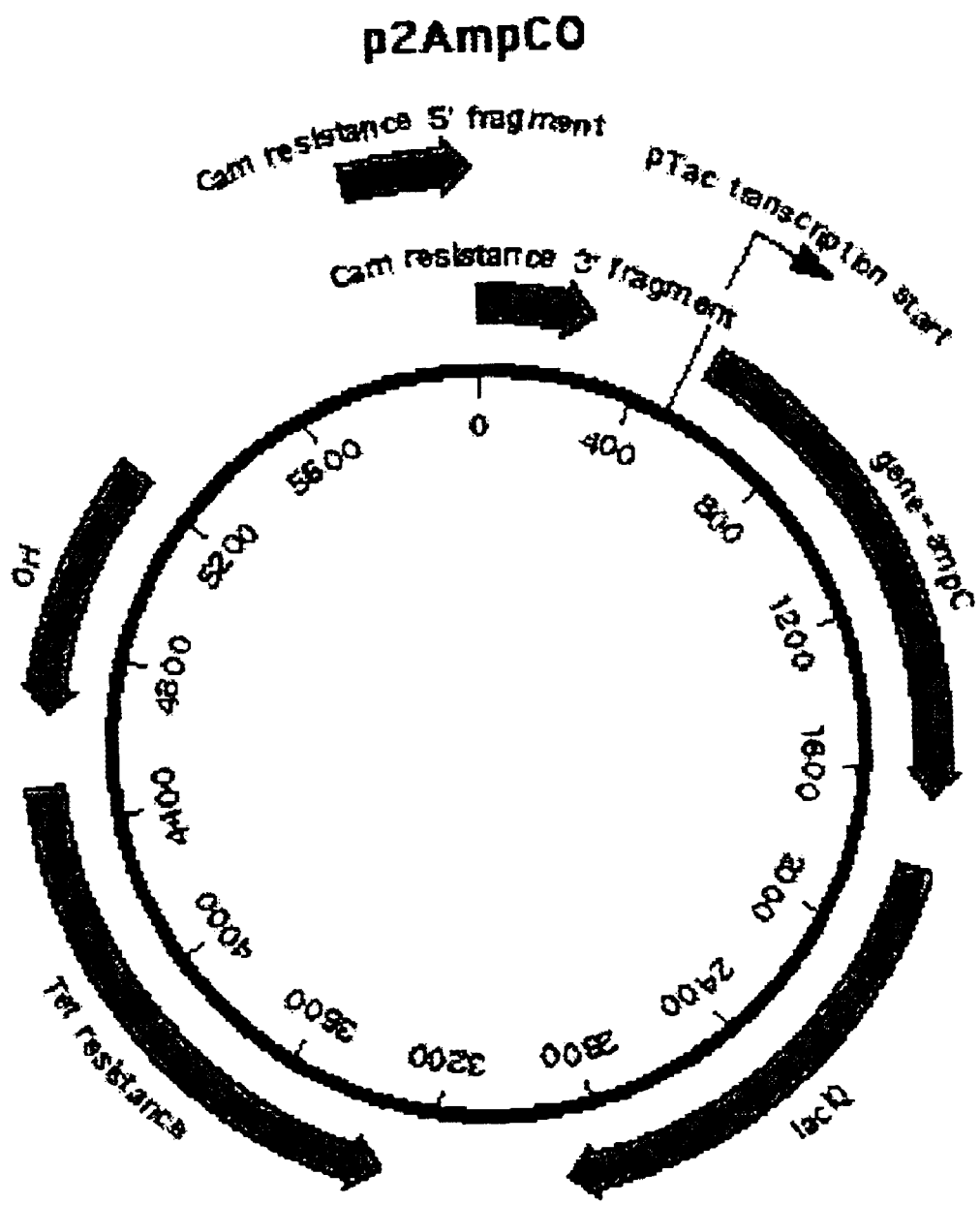
FIG. 7 is a diagram of plasmid p2AmpC0, which is a pACSE plasmid containing the polypeptide coding sequence of an ampicillin resistance gene and the lacI$^Q$ gene.

Preferred expression vectors for use in transforming prokaryotic host cells such as *E. coli* are plasmids, preferably pACSE or derivatives of pACSE, such as pACSE2 or pACSE3. pACSE, whose structure is shown in FIG. 1 and whose nucleotide sequence is shown in FIGS. 2A–B, was constructed as described in Example 1 infra. pACSE2, whose structure is shown in FIG. 3 and whose nucleotide sequence is shown in FIGS. 4A–B, is identical to pACSE except that it carries the lacI$^q$ gene for lac repressor. Presence of the lacI$^q$ gene on the vector ensures that there will always be sufficient repressor to regulate expression of the Xu cloned resistance gene. That in turn assures that, independent of the host cell, all comparisons will be of genes that are expressed at exactly the same level so that the resistance phenotype reflects only the properties of the plasmid-encoded protein, not differences in level of expression. pACSE3 is derived from pACSE2 by site directed mutagenesis of the unique NcoI site (compare FIGS. 4A–B and 5A–B) to convert it to a BspHI site, and site directed mutagenesis of the two BspHI sites of pACSE2 (compare FIGS. 4A–B and 5A–B) to eliminate those sites, thereby rendering the new BspHI site unique. Other derivatives can easily be prepared, e.g., by manipulating specific nucleotides in order to create or destroy restriction enzyme recognition sites or by inserting additional genes coding for drug resistance polypeptides that may be necessary to permit use of the plasmid in other hosts.

Mammalian host cells can also be used to express the mutant resistance gene. Mammalian cells suitable for carrying out the present invention include, among others: COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573), CHOP, and NS-1 cells. Suitable expression vectors for directing expression in mammalian cells generally include a promoter, as well as other transcription and translation control sequences known in the art. Common promoters include SV40, MMTV, metallothionein-1, adenovirus E1a, CMV, immediate early, immunoglobulin heavy chain promoter and enhancer, and RSV-LTR.

Regardless of the selection of host cell, once the mutant resistance gene has been ligated to its appropriate regulatory regions using well known molecular cloning techniques, it can then be introduced into a suitable vector or otherwise introduced directly into a host cell using transformation protocols well known in the art (Sambrook et al., *Molecular Cloning: A Laboratory Manual,* Second Edition, Cold Spring Harbor Press, N.Y. (1989), which is hereby incorporated by reference). Typically, introduction of the mutant resistance gene into host cells is accomplished via transformation, particularly transduction, conjugation, mobilization, or electroporation.

Introduction of the mutant resistance gene can be accomplished either u i by stably incorporating the mutant resistance gene into the genome of the host cell or by incorporating the mutant resistance gene into a plasmid which can be taken up by a host cell. Whether or not the mutant resistance gene is stably incorporated into the host cell genome will depend, at least in part, on the selection of the expression system.

After introducing the mutant resistance gene into the host cell, transformants can be selected on the basis of resistance to a selection agent (e.g., tetracycline) conferred by presence of the expression vector in the host cell.

Next, transformants are collected and then challenged with a drug to determine whether the mutant resistance gene can confer, to the host cell, enhanced drug resistance. The population of transformed host cells constitutes a library of variant resistance genes which have been highly mutated. However, only a small fraction, typically 1–2%, of the library will remain resistant to a particular drug, and only a small fraction of those will have been significantly improved by the mutagenesis. To identify the rare improved mutant resistance genes, the library is expanded and divided into samples such that every sample contains several descendants of each original mutant resistance gene that was still drug resistant. This can be accomplished by growing the host cell on a selection medium that includes one or more drugs against which the precursor resistance gene and/or mutant resistance gene provides resistance (i.e., allowing the host cell to survive). This selects mutant resistance genes which confer some level of resistance from those that do not, thereby increasing the population of host cells containing mutant resistance genes that confer any resistance to the drug.

Selection of host cells bearing mutant resistance genes can be conducted using known techniques including, without limitation, a test for the minimum inhibitory concentration ("MIC") of one or more drugs, disc diffusion of one or more drugs, or both of these tests in combination.

Basically, a MIC determination is carried out by preparing serial dilutions of drugs in a micro-well plate and measuring host cell growth within those wells. The MIC for a particular set of host cells containing a mutant resistance gene is determined by examining the wells to locate the lowest concentration of drug which inhibited cell growth. This is capable of discriminating generally between those host cells containing mutant resistance genes conferring different degrees of resistance against the particular drug.

A disc diffusion test is carried out by spreading approximately $10^7$ cells onto a broth plate and then a set of antibiotic discs, i.e., uniform paper discs containing known amounts of antibiotic drugs, are placed onto the plate. The plate is then incubated overnight. As the drugs diffuse from the discs, the drug concentration decreases with increasing distance from the disc until the concentration declines below an inhibitory level. The result is a clear zone of inhibition within a lawn of cells. The larger the clear zone of inhibition, the more sensitive the cells are to that drug. While direct correlations with MIC levels are not possible, comparisons of plates with different mutant strains allows the sensitivities of those strains to be compared on the basis of the sizes of the zones of inhibition.

Because the MIC test is only as sensitive as the serial dilutions employed (i.e., within a two-fold range), the disc diffusion test provides a more sensitive discrimination among mutants. Thus, the disc diffusion test can distinguish between two mutants which exhibited identical MIC results. Therefore, the combination of tests is desirable.

The best overall resistance to a multiplicity of drugs (i.e., that are used to screen the various mutant resistance genes from each round) can also be measured. The drug resistance score for each mutant resistance gene should reflect the overall improvement in resistance to each of the drugs used. For any one drug the score is best expressed as the log to the base 2 of the MIC ("$\log_2$ MIC"). The resistance to two drugs would then be a point in two dimensional space that is the two $\log_2$ MIC scores on the X and Y axes. The resistance to those same drugs for another mutant would be a different point on the X and Y axes, and the overall improvement would be represented by the distance between those two points. Similarly, for 11 drugs the overall resistance is a point in 1 dimensional space, and improvement is the distance in 11 dimensional space between the two points. For example, E. coli JM 109 carrying the plasmid vector pAmpC0 with a wildtype ampc gene is, thus, 10.5 units from E. coli JM 109 carrying the plasmid vector pACSE without an ampC gene (see Table 1, Example 2).

The improvement scores, or distances, are easily calculated in a spreadsheet by application of the Pythagorean Theorem: for each drug the difference between the $\log_2$ MIC for the strain of interest and the reference strain is calculated, us and that value is squared. The squared values are summed over all of the drugs and the distance (improvement score) is the square root of that sum.

This method can be generalized to any situation that involves comparing scores for candidate proteins when any number of multiple factors are being analyzed in order to identify the best candidate. The reference point can be the absence of the protein, any particular candidate protein of interest, or a moving optimum where the optimum point is defined by the best score among all of the candidates for that particular factor. The factors need not be drug resistance, but could include such items as pH optimum, thermal stability, solvent stability, sensitivity to inhibitors, etc. The factors can easily be weighted according to their perceived importance, and the spreadsheet can easily be set up to automatically identify the best candidate.

Another approach for measuring best overall resistance against a number of drugs can be obtained by serially exposing the host cells containing the mutant resistance genes to a multiplicity of drugs via MIC selection. Host cells are exposed to a first drug in a series of tubes or wells, and resistant host cells are obtained from the tube or well containing the second highest concentration of the first drug which supported cell growth. The selected host cells are then exposed to the second drug, which is added to the first tube of the series and then serially diluted. The following day, resistant host cells from the second highest concentration of the second drug which supported cell growth are obtained. This MIC process is repeated for each of the drugs. The population of host cells obtained following exposure to the final drug in the series are cells that grow at the second highest concentration for each of the drugs tested. That population of host cells can either be used as the starting point for the next cycle of mutagenesis and selection as described, or cells can be further selected by performing a disc diffusion test as described above to identify the single most resistant host cell.

Regardless of the approach for selecting the best mutant resistance gene of the first round, further mutagenesis of the selected mutant resistance gene can be carried out following recovery of the isolated mutant resistance gene from the host cell. After a second round of mutagenesis, carried out as described above, the resulting second round mutant resistance genes are again introduced into host cells and the host cells screened for transformation and then enhanced resistance. As noted above, a population of host cells or the single most-resistant host cell (whether resistant against one drug or a multiplicity of drugs) can be selected. This process of mutagenesis and screening can be repeated for successive rounds, preferably until no further enhancement of the resistance phenotype is perceived, i.e., where the resulting round n mutant resistance gene displays no greater resistance activity than its predecessor round (n−1) mutant resistance gene.

Because the round n mutant resistance genes were no more effective than the selected round (n−1) mutant resistance gene, the round (n−1) mutant resistance gene and its encoded polypeptide (whether mutant or not) can be employed for subsequent sequence analysis. Sequencing of the mutant resistance gene and its encoded polypeptide can be carried out using conventional sequencing equipment. The sequence of the mutant resistance gene and its encoded polypeptide are compared to the wild-type resistance gene and its encoded polypeptide, respectively, and the differences are identified. If only a single mutational difference exists between the mutant resistance gene and the wild-type resistance gene or the mutant polypeptide and the wild-type polypeptide, then it is necessarily true that the mutant resistance gene (and its encoded mutant polypeptide) can evolve from the wild-type resistance gene. The present invention is directed toward determining the evolutionary potential of mutant resistance genes or polypeptides that include a plurality of mutations with respect to the wild-type resistance gene or polypeptide.

According to a preferred aspect of the present invention, the mutant resistance gene encodes a mutant resistance polypeptide that includes two or more amino acid modifications relative to the wild-type resistance polypeptide.

Because individual mutational events occur at a rate of about $4 \times 10^{-10}$ per cell division (Hall, "Spectrum of Mutations That Occur Under Selective and Non-selective Conditions in E. coli ," Genetica 84:73–76 (1991), which is hereby incorporated by reference), it is most likely that naturally evolving wild-type resistance genes will develop one mutation at a time under the selective pressure of a particular drug (i.e., antibiotic, antiviral, antifungal, antiprotozoal, etc.). Therefore, having identified one or more mutant resistance genes which exhibit the greatest increase in resistance activity (i.e., against a particular drug), the next step in the present invention involves determining whether a selected mutant resistance gene is likely to evolve through two or more independent mutation events.

With the differences between the wild-type resistance gene and the mutant resistance gene or the wild-type resistance polypeptide and the mutant resistance polypeptide identified, the next step involves preparing a library of singly mutated resistance genes. The library of singly mutated resistance genes represents an array of possible first mutation events that could eventually evolve into the selected (e.g., round n−1) mutant resistance gene. The singly mutated resistance genes can be generated from the precursor resistance gene by performing site-directed mutagenesis using known procedures, for example, manufacturer's directions accompanying a site directed mutagenesis kit (CloneTech, Palo Alto, Calif.).

If the number of amino acid substitutions in the round (n−1) mutant is large, it may be expensive or inconvenient to introduce each of those substitutions by site-directed mutagenesis. Some of those substitutions may contribute nothing to resistance (i.e., neutral) or may actually reduce the level of resistance below what it would be if those substitutions were not present (i.e., deleterious). The number of neutral and deleterious substitutions may be reduced by back-crossing. Back-crossing is accomplished by: amplifying the gene from the round (n−1) mutant and the wild-type gene under high fidelity conditions using low-error-rate enzymes such as polymerase (StrataGene, La Jolla, Calif.); combining the round (n−1) mutant amplified DNA with a 10- to 20-fold excess of the amplified wild-type DNA; shuffling the combined DNA as described above; cloning and transforming into a suitable host as described above; and selecting for resistance comparable to that of the (n−1) mutant. If the resulting sequence confers resistance equal to or greater than that of the (n−1) mutant sequence, and includes fewer amino acid substitutions, then those amino acid substitutions that were eliminated were either neutral or deleterious and the resulting "back-crossed" mutant may be used in place of the round (n−1) mutant in all subsequent stages of the present invention. This approach does not guarantee removal of all neutral or deleterious mutations because removal is both a matter of probability and a matter of linkage. Those neutral or deleterious substitutions that are tightly linked (i.e., close) to amino acid substitutions that contribute to the resistance phenotype will be less likely to be eliminated than those that are far away from amino acid substitutions that contribute to the resistance phenotype.

According to a preferred aspect of the present invention, each of the singly mutated resistance genes encodes a singly mutated polypeptide consisting of one of the two or more amino acid modifications of the mutant polypeptide. For example, if five amino acid modifications were identified in the round (n−1) mutant resistance polypeptide as compared to the wild-type resistance polypeptide, then five singly mutated resistance genes would be prepared, each coding for a different singly mutated polypeptide containing a single amino acid modification.

Once each of the singly mutated resistance genes has been prepared, they are then inserted individually into host cells and the individual host cells grown on a selection medium to select transformants. The transformed host cells are then grown on a selection medium containing one or more drugs and individual host cells which exhibit increased resistance are selected using the selection techniques described above. Those host cells exhibiting increased activity are selected or, alternatively, only the most resistant host cell population is selected.

It is possible that some of the singly mutated resistance genes confer a decrease or, alternatively, no appreciable increase in resistance activity. Because these singly mutated resistance genes, if they arose in nature, would not be selected over other wild-type resistance genes, they are not selected for further analysis.

It is also possible that none of the host cells in the library of host cells containing singly mutated resistance genes will exhibit increased resistance activity. Because the various singly mutated resistance genes, if they arose in nature, would not be selected over other wild-type resistance genes, it is highly unlikely that the mutant resistance gene (i.e., obtained from round (n−1) of mutagenesis and selection) would evolve any of the independent mutations which were screened via the singly mutated resistance genes. In such a case, the round (n−1) mutant resistance gene and its encoded mutant polypeptide would not be useful for screening drugs, because it would be highly unlikely that the mutant resistance gene or its encoded polypeptide would ever result in nature (i.e., given the selection criteria employed).

After selecting the singly mutated resistance genes which confer increased resistance activity, it is desirable to assess whether any of the selected singly mutated resistance genes confers a substantially identical degree of resistance activity as the mutant resistance gene (i.e., obtained from round (n−1) of mutagenesis and selection). If differences in resistance activity exist between the selected singly mutated resistance gene and the mutant resistance gene, then it is highly probable that additional mutations present in the mutant polypeptide but not in the singly mutated polypeptide are responsible for such differences in activity. However, where there is no appreciable difference in their resistance activity, it is highly probable that Ca, additional mutations present in the mutant polypeptide but not in the singly mutated polypeptide are irrelevant to the selectability of the mutant polypeptide. If true, that would mean that there would be no selection of the mutant resistance gene. Therefore, its evolutionary potential would be highly improbable.

Assuming that difference exist between the resistance activities of the singly mutated polypeptide and the mutant polypeptide, then selected singly mutated resistance genes are modified, e.g., by further site-directed mutagenesis, to prepare one or more doubly mutated resistance genes.

According to the preferred aspect of the present invention, each of the doubly mutated resistance genes encodes a doubly mutated polypeptide. For example, assuming that two of five singly mutated resistance genes resulted in increased resistance activity, then each of the two selected singly mutated resistance genes could be used to prepare libraries of doubly mutated resistance genes which encode polypeptides that include various combinations of two amino acid modifications (i.e., that were present in the mutant polypeptide).

Once each of the doubly mutated resistance genes has been prepared, they are then inserted individually into host cells and the individual host cells grown on a selection medium to select transformants. The transformed host cells are then grown on a selection medium containing one or more drugs and individual host cells which exhibit increased resistance are selected using the selection techniques described above. Those host cells exhibiting increased activity are selected or, alternatively, only the most resistant host cell population is selected.

As before, it is possible that some of the doubly mutated resistance genes confer a decrease or, alternatively, no appreciable increase in resistance activity (as compared to the singly mutated resistance genes). Because these doubly mutated resistance genes, if they arose in nature, would not be selected over naturally-occurring singly mutated resistance genes, they are not selected for further analysis. It is also possible that none of the host cells in the library of host cells containing doubly mutated resistance genes will exhibit increased resistance activity. Because the various doubly mutated resistance genes, if they arose in nature, would not be selected over other naturally-occurring singly mutated resistance genes, it is highly unlikely that the mutant resistance gene (i.e., obtained from round (n−1) of mutagenesis and selection) would evolve any of the independent mutations which were screened via the doubly mutated resistance genes. In such a case, the round (n−1) mutant resistance gene and its encoded mutant polypeptide would not be useful for screening drugs, because it would be highly unlikely that the mutant resistance gene or its encoded polypeptide would ever result in nature (i.e., given the selection criteria employed).

After selecting the doubly mutated resistance genes which confer increased resistance activity, it is desirable to assess whether any of the selected doubly mutated resistance genes confers a substantially identical degree of resistance activity as the mutant resistance gene (i.e., obtained from round (n−1) of mutagenesis and selection). If differences in resistance activity exist between the selected doubly mutated resistance gene and the mutant resistance gene, then it is highly probable that additional mutations present in the mutant polypeptide but not in the doubly mutated polypeptide are responsible for such differences in activity. However, where there is no appreciable difference in their resistance activity, it is highly probable that additional mutations present in the mutant polypeptide but not in the doubly mutated polypeptide are irrelevant to the selectability of the mutant polypeptide. If true, that would mean that there would be no selection of the mutant resistance gene. Therefore, its evolutionary potential would be highly improbable.

Instead, the selected doubly mutant resistance gene and its encoded doubly mutant polypeptide would possess a high probability of evolving by natural selection. Such mutant resistance genes and polypeptides would, therefore, be useful for identifying next-generation drugs capable of overcoming their resistance prior to their highly probably development in nature. This aspect of the present invention is discussed in greater detail below.

However, assuming that difference exist between the resistance activities of the doubly mutated polypeptide and the mutant polypeptide, then selected doubly mutated resistance genes are then modified, e.g., by further site-directed mutagenesis, to prepare one or more triply mutated resistance genes. According to the preferred aspect of the present invention, each of the triply mutated resistance genes encodes a triply mutated polypeptide. For example, assuming that one of various doubly mutated resistance genes resulted in increased resistance activity, then the selected doubly mutated resistance gene would be used to prepare a library of triply mutated resistance genes which encode triply mutated polypeptides that include gown various combinations of three amino acid modifications (i.e., that were present in the mutant resistance polypeptide).

This process of step-wise mutagenesis, selection, and assessment of resistance activity (i.e., relative to the mutant resistance gene/polypeptide identified in round (n−1) of the mutagenesis and selection) is carried out until either the mutant resistance polypeptide is recreated (indicating that it has a highly probable evolutionary potential) or a multiply mutated polypeptide bearing fewer amino acid modifications is identified as having substantially the same resistance activity aside has a highly improbable evolutionary potential and the multiply mutated polypeptide has a highly probably evolutionary potential). Regardless of the outcome, either the mutant resistance gene or the multiply mutated resistance gene can be employed for candidate drug screening as described hereinafter. In such cases where the multiply mutated resistance gene (but not the mutant resistance gene) is likely to evolve, the process of providing a mutant resistance gene is carried out by site-directed mutagenesis and the process of determining evolutionary potential is assessed upon comparing the resistance activity of the multiply mutated polypeptide versus the mutant polypeptide.

Alternatively, where the mutant resistance gene possesses confers enhanced resistance as a result of mutation introduced into noncoding regions of the resistance gene, the singly mutated resistance genes each consist of a single nucleic acid modification to the non-coding region, whereby each encodes the same wild-type resistance polypeptide. In such as case, the step-wise mutagenesis, selection, and assessment of resistance activity (i.e., relative to the mutant resistance gene identified in round (n−1) of the mutagenesis and selection) is carried out until either the mutant resistance gene is recreated (indicating that it has a highly probable evolutionary potential) or a multiply mutated resistance gene bearing fewer nucleotide modifications is identified as having substantially the same resistance activity as the mutant resistance gene (indicating that the mutant resistance gene has a highly improbable evolutionary potential and the multiply mutated resistance gene has a highly probably evolutionary potential).

The entire process, from first round of mutagenesis to last round of mutagenesis, can be performed any number of times to obtain a pool of selected mutant resistance genes. From this pool of mutant resistance genes, a natural evolutionary pathway can be recreated to determine whether such mutant resistance genes are likely to develop in nature or, if not, whether multiply mutated resistance genes encoding fewer amino acid modifications than the mutant resistance genes are likely to develop.

A further aspect of the present invention relates to a mutant resistance gene which is prepared according to the process which includes the steps of providing a resistance gene, introducing a plurality of mutations into the resistance gene to produce a mutant resistance gene which encodes a mutant polypeptide comprising at least two amino acid modifications, the mutant polypeptide conferring enhanced resistance to host cells comprising the mutant resistance gene; and then determining whether the mutant polypeptide is likely to evolve through independent mutations.

By introducing the plurality of mutations into the resistance gene to produce the mutant resistance gene, it is intended that random multiple mutagenesis occur as described above, preferably by DNA shuffling. After mutagenesis, the mutant resistance gene can be inserted into a host cell as described above, transformed host cells can be selected, and then the transformed host cells can be assayed to determine whether they can survive when grown on a selection medium that includes one or more drugs, wherein survival of the host cell indicates that the mutant polypeptide is effective (i.e., confers resistance) against the one or more drugs. As indicated above, the process of mutagenesis, insertion into host cells, and assaying transformed host cells can be repeated, preferably until a subsequent round of mutagenesis yields no substantial increase in resistance activity over the mutant resistance gene from the previous round. After isolating the mutant resistance gene and identifying the sequence of the mutant resistance gene, the step of determining whether the mutant resistance gene possess evolutionary potential is carried out as described above.

The resulting mutant resistance gene or multiply mutated resistance gene, having a coding sequence which includes a plurality of mutations, encodes a mutant protein or polypeptide that (i) includes at least two amino acid modifications (i.e., relative to the wild-type amino acid sequence), (ii) confers enhanced resistance to a host cell which expresses the mutant protein or polypeptide, and (iii) is likely to evolve through independent mutations. The mutant resistance gene can be a mutant antibiotic resistance gene, a mutant antiviral resistance gene, a mutant anti-fungal resistance gene, or a mutant anti-protozoal resistance gene. The coding regions of several mutant antibiotic (ampicillin) resistance genes of the present invention are shown in FIGS. 8A–B and include the nucleotide sequences according to SEQ. ID. Nos. 6, 8, and 10.

The mutant or multiply mutated resistance-conferring protein or polypeptide is expressed by the mutant or multiply mutated resistance gene prepared according to the present invention. The mutant or multiply mutated resistance protein or polypeptide of the present invention includes at least two amino acid modifications relative to the wild-type resistance-conferring protein or polypeptide and is likely to evolve through independent mutations. The mutant resistance-conferring protein or polypeptide can be a mutant antibiotic resistance protein or polypeptide, a mutant anti-viral resistance protein or polypeptide, a mutant anti-fungal resistance protein or polypeptide, a mutant anti-protozoal resistance protein or polypeptide. Several mutant antibiotic (ampicillin) resistance polypeptides of the present invention are shown in FIG. 9 and include the amino acid sequences according to SEQ. ID. Nos. 7, 9, and 11.

By developing a mutant resistance gene in vitro and determining that the mutant resistance gene (or a multiply mutated resistance gene) is likely to evolve by natural selection through a series of at least two independent or successive mutation events, such a mutant resistance gene can be used to develop next generation drugs which are effective against organisms (i.e., pathogenic organisms) that possess those resistance genes. Thus, a further aspect of the present invention relates to a method of screening a drug for anti-pathogenic activity against a pathogen including a mutant anti-pathogenic resistance gene. This method is carried out by providing a host cell that includes a mutant anti-pathogenic resistance gene either including two or more nucleic acid modifications or encoding a mutant anti-pathogenic polypeptide which includes two or more amino acid modifications, wherein the mutant anti-pathogenic resistance gene or mutant anti-pathogenic polypeptide confers a selectable advantage to the host cell, growing the host cell on a selection media that includes a candidate drug or combinations thereof, and then determining whether the host cell is capable of growing on the selection media, wherein absence of host cell growth and/or proliferation indicates anti-pathogenic activity for the candidate drug or combinations thereof.

By providing the host cell, it is intended that the host cell which includes the mutant anti-pathogenic resistance gene can be prepared by providing an anti-pathogenic resistance gene (that can be prepared and isolated as described above), introducing a plurality of mutations into the anti-pathogenic resistance gene to produce the mutant anti-pathogenic resistance gene, and then inserting the mutant anti-pathogenic resistance gene into a host cell under conditions effective for expression of the encoded polypeptide. Preferably, the mutant anti-pathogenic resistance gene includes either mutations resulting in two or more nucleic acid modifications encoding two or more amino acid modifications in the encoded polypeptide, or two or more nucleic acid modifications present in a promoter region. The preparation of the mutant anti-pathogenic resistance gene and its subsequent insertion into a host cell can be carried out as described above.

Having identified a drug or combination of drugs which are effective against host cells that include a mutant resistance gene that it likely to evolve in nature, another important characteristic of the identified drug or combination of drugs is the likelihood that it (they) will provide long-term or continued therapeutic treatment against pathogens in which such resistance genes actually evolve. Thus, a further aspect of the present invention relates to a method of assessing the potential longevity of a candidate anti-pathogenic drug. The premise in performing this method is that the mutant resistance gene of the present invention, which has been determined to be likely to evolve, has actually evolved and become a wild-type gene within the population of a particular pathogen. The greater the minimum number of mutations required to overcome the activity of the anti-pathogenic drug, the greater the potential longevity of the candidate anti-pathogenic drug. For example, it is much more likely a drug will provide only short term activity against a pathogen when only a single mutational event in a pathogen's resistance gene is required to confer resistance against the drug to the pathogen. In sharp contrast, when more than one mutation event must occur in a pathogen's resistance gene, the longevity of the drug's efficacy against the pathogen will be substantially longer and such longevity will be relative to the number of mutational events which must occur to confer resistance against the drug to the pathogen.

Thus, this method is carried out by providing a resistance gene encoding a polypeptide which is ineffective against a candidate anti-pathogenic drug, introducing multiple mutations into the resistance gene to produce a mutant resistance gene which encodes a mutant polypeptide including two or more amino acid modifications, wherein the mutant polypeptide is effective against the candidate anti-pathogenic drug, and then determining the minimum number of mutations required to overcome the activity of the candidate anti-pathogenic drug. Introduction of multiple mutations into a resistance gene can be carried out as described above; however, after introducing such multiple mutations into the resistance gene, the resulting mutant resistance gene is inserted into a host cell as described above, which host cell is then assayed to indicate whether the host cell can survive on a selection medium that includes a candidate anti-pathogenic drug. If the host cell survives, the mutant polypeptide is effective against the candidate anti-pathogenic drug. To determine the minimum number of mutations required to achieve host cell resistance, the two or more amino acid modifications of the mutant polypeptide are identified and then, according to the procedures set forth above, it is determined whether an evolutionary pathway exists for the mutant polypeptide (i.e., multiple rounds of site-directed mutagenesis followed by selection of singly, doubly, or multiply mutated genes exhibiting increased resistance).

EXAMPLES

The following examples are provided to illustrate embodiments of the present invention but are by no means intended to limit its scope.

Example 1

Construction of pACSE Vector

Plasmid pACYC184 (Rose, "The Nucleotide Sequence of pACYC184," *Nucleic Acids Res.* 16(1):355 (1988); Genbank Accession No. X06403, which are hereby incorporated by reference) was digested with restriction endonuclease Mscl (New England Biolabs, Beverly, Mass.) and the digested DNA was subjected to agarose gel electrophoresis. The larger fragment was excised from the gel and purified with a Qiagen Gel Purification Column (Valencia, Calif.).

Using plasmid pSE380, bp 6-662 which contain the pTAC promoter and multiple cloning site cartridge, were PCR amplified using the following primers:

Forward Primer 252 (SEQ ID. No. 12):

GGGGGG<u>TGGC CA</u>TTGTTT OACAGCTTAT CATCG      35

Reverse Primer 253 (SEQ ID. No. 13):

CAGGCTGAAA ATCTTCTCTC ATC      23

Primer 252 includes an MscI site (underlined) at its 5' end, and the resulting amplicon includes an MscI site at the position corresponding to bp 598–603 of pSE380. PCR was performed using Pfu polymerase (Stratagene, La Jolla, Calif.) according to manufacturer's instructions. The resulting amplicon was digested with restriction endonuclease MscI (New England Biolabs, Beverly, Mass.) and purified with a Qiagen PCR Purification column.

The fragment of plasmid pACYC184 and the digested amplicon were combined and ligated with T4 ligase (GibcoBRL, Rockville, Md.) according to manufacturer's instructions, yielding pACSE (FIG. 1).

Table 1 below shows that the plasmid carrying the wild-type ampC gene (ampC0), plasmid pAmpC0, confers resistance to ampicillin, cephalothin, and cefuroxime (boxed cells) but not to pipericillin, temocillin, cefotaxime, ceftazidime, cefepime, imipenem, meropenem, or aztreonam. These properties are similar to naturally occurring AmpC plasmids and indicate that the plasmid-borne wild-type E. coliK12 ampC gene is a valid model for the evolution of ampC β-lactamases in clinical pathogens.

The drug resistance score for each mutant should reflect the overall improvement in resistance to each of the drugs used. For any one drug the score is best expressed as the log to the base 2 of the MIC ("$\log_2$ MIC"). The resistance to two drugs would then be a point in two dimensional space that is the two $\log_2$ MIC scores on the X and Y axes. The resistance to those same drugs for another mutant would be a different point on the X and Y axes, and the overall improvement would be represented by the distance between those two points. Similarly, for 11 drugs the overall resistance is a point in 11-dimensional space, and improvement is the distance in 11 dimensional space between the two points. Strain JM109 carrying the wildtype gene, pAmpC0, is thus 10.5 units from JM109 carrying the plasmid vector pACSE without an AmpC gene (Table 1).

TABLE 1

Results of Minimum Inhibitory Resistance Tests Against Different Antibiotics

| Drug | Clinical Resistance MIC (NCCLS)* | MIC pACSE | MIC pAmpC0 | MIC pAmpC13A | MIC pAmpC41A | MIC pAmpC21B |
|---|---|---|---|---|---|---|
| Ampicillin | 32 | 2 | 128 | 1024 | 1024 | 1024 |
| Pipericillin | 128 | 4 | 16 | 512 | 1024 | 512 |
| Temocillin | 32** | 16 | 16 | 32 | 32 | 16 |
| Cephalothin | 32 | 16 | 1024 | 1024 | 2048 | 4096 |
| Cefuroxime | 32 | 16 | 64 | 64 | 64 | 512 |
| Cefotaxime | 64 | 0.0625 | 1 | 32 | 32 | 16 |
| Ceftazidime | 32 | 0.50 | 2 | 256 | 256 | 32 |
| Cefepime | 32 | 0.03125 | 0.0625 | 8 | 8 | 0.06125 |
| Imipenem | 16 | 0.25 | 0.25 | 0.25 | 0.25 | 0.5 |
| Meropenem | 16 | 0.00195 | 0.00195 | 0.03125 | 0.06125 | 0.03125 |
| Aztreonam | 32 | 0.5 | 4 | 64 | 64 | 32 |
| Distance from pACSE | | 0 | 10.5 | 21.5 | 22.3 | 19.3 |

Example 2
Preparation of E. coli Host Cell Including Wild-type ampC Gene

The ampC gene of E. coliK12 was cloned onto the low-copy-number vector pACSE (prepared according to Example 1), where it is expressed under control of the Lac repressor at a level that confers resistance to ampicillin comparable to that associated with ampC plasmids from clinical isolates. All experiments utilizing ampicillin resistance will be directed toward the cloned and regulated ampC gene (or mutant ampC gene) in such a way that the regulation, i.e., the amount of enzyme produced per cell, will be held constant throughout the experiments and all of the "improvement" in resistance will come from improvement in β-lactamase activity.

Example 3
DNA Shuffling of AmpC Gene

In a first step, the plasmid pAmpC0 is isolated from its E. coli host and then amplified with Taq polymerase in a 100 μl reaction using the following primers:

Forward Primer 266 (SEQ. ID. No. 14):

TCATCCGGCT CGTATAATGT GTA      25

Reverse Primer 267 (SEQ. ID. No. 15):

ATCGCGTCCG CCATCTCCAG      20 in connection with 1–3 ng of plasmid as template. The resulting PCR product is obtained and a 1 μl sample is run on a 1.5% agarose gel. The gel separated sample is then purified on a Qiagen PCR column eluted with 10 mM Tris-HCl (pH 8.0) using Qiagen buffer EB without EDTA. The concentration of the resulting DNA amplicon, which contains the ampC gene, was determined to be 80 ng/µl using a DNA fluorometer.

Next, error-prone DNAase I digestion was performed using 1 82 g amplicon in 20 µl of water, to which was added 2 µl of 10× DNAase I buffer (500 mM potassium maleate pH 6.0, 100 mM $MnCl_2$). The solution was allowed to equilibrate for 10 minutes at 15° C. After equilibration, 1 µl of Promega RQ1 DNAase I was added to the solution and the solution was immediately vortexed and returned to 15° C. Two min. later, 2.5 µl DNAase Stop (3× agarose dye containing 500 mM EDTA) was added and the solution was incubated for 10 min at 90° C. From the incubated solution containing the digested plasmid fragments, a 5 µl sample was obtained and run on 1.5% agarose gel. The fragments were then purified over a CentriSep column (Princeton Separations, Princeton, N.J.) according to manufacturer's instructions. Purified fragments were between about 50 to 100 bp as verified by gel electrophoresis.

To the digested CentriSep purified DNA fragments, an equal volume of Qiagen Taq Polymerase Master Mix+1 µl 50 MM $MgCl_2$ for every 33 µl of reaction volume. Using a Hybrid thermocycler (Model PCR Sprint, Hybrid, Middlesex, UK), the Shuffling program was run for a period of four hours and 15 min. A 5 µl sample of shuffled DNA was obtained from the thermocycler and then run on a 1.5% agarose gel, yielding a smear of DNA having an average size of the ampC containing amplicon. The concentration of the shuffled DNA was measured with a fluorometer and was determined to be greater than the desired 40 ng/µl.

Finally, the shuffled DNA was re-assembled by first preparing a 10× and a 50× dilution of the shuffled DNA solution. Using 2 µl of undiluted,. 10× diluted and 50× diluted product as template in 100 µl, Qiagen Taq reaction was performed using the following primers:

Forward Primer 258 (SEQ. ID. No. 16)

AAAACCATGG TCAAAACGAC GCTCT    25

Reverse Primer 259 (SEQ. ID. No. 17)

GTTGGGTCCT GGCCACTAGT ACTTC    25

From each reaction at a particular dilution, the reaction products were split into two 50 µl aliquots, which were introduced in the Hybaid thermocycler on its reassembly setting. After reassembly, the split reactions were combined together to produce three separate reactions based on the previous dilutions. For each reaction, 1 µl was collected and run on a 1.5% agarose gel to confirm synthesis of full length fragment. The reactions which afforded the highest yield with the least amount of non-specific product were the 10× and 50× dilution reactions, which were combined. This reaction product was purified on Qiagen PCR purification column, then re-suspended in 50 µl of TE, and quantified on fluorometer.

Example 4

Cloning of Multiply Mutated ampC into *E. coli* DH5α-E

The DNA concentration of the reaction product of Example 3 was 36 ng/µl. Accordingly 10 µl of the reaction product was digested with 10 units each of restriction endonucleases NcoI and SacI (New England Biolabs, Beverly, Mass.) in a 20 µl total reaction volume containing 1× New England Biolabs Buffer 4. Following digestions for 1 hour at 37° C. the digest was purified over a Qiagen (Valencia, Calif.) PCR cleanup column and quantified on a DNA Fluorometer.

Plasmid pACSE2 (10 µg) was similarly digested with restriction endonucleases NcoI and SacI and Calf Intestinal Alkaline Phosphatase (New England Biolabs, Beverly, Mass.) in Buffer 4, purified over a Qiagen (Valencia, Calif.) PCR cleanup column, and quantified on a DNA Fluorometer. A stock of this digested plasmid is routinely stored, frozen, in the Hall laboratory (University of Rochester, Rochester, New York).

258 ng of digested pACSE2 (1.4 µl) was combined with 44 µl of digested purified product from Example 3, 31 µl of T4 Ligase and 12.5 µl of 5× T4 ligase buffer (GibcoBrl, Rockville, Md.) and incubated overnight at room temperature.

The resulting ligation product was purified and concentrated by ethanol precipitation, taken up in 10 µl, and two 4 µl aliquots were used to electroporate strain DH5α-E. Following electroporation the transformed cells were incubated in SOC medium at 37° C. for 90 minutes.

Example 5

Selection of *E. coil* Containing Multiply Mutated ampC and Exhibiting Enhanced Resistance

*E. coli* host cells prepared according to Example 4 were diluted into 100 ml MuellerHinton-IPTG (MH-T) broth. Duplicate samples of $10^0$, $10^1$, and $10^2$ dilutions were spread onto L(tet) plates to estimate total transformants, and duplicate $10^0$ and $10^1$ samples were spread onto MH-I(ampicillin) plates to estimate the number of $Amp^R$ transformants. 10 mg ampicillin was added to each culture using 1 ml of a 10 mg/ml ampicillin solution. The culture was allowed to stand overnight at 37° C. without shaking.

Next, the minimum inhibitory concentration of a number of drug was determined. An estimate of viable cells was calculated by assuming that an $A_{600}$ of 1.0 is equivalent to $1.9×10^8$ per ml for DH5α-E cells. A sample of the overnight culture was diluted into 70 ml of MH-I so that the number of cells per ml $10^5$ per ml. The resulting suspension was used to determine MIC in 48-well microtiter plates.

Serial dilutions were prepared by first determining the volume of drug solution to be added to the first well in each row to achieve the desired concentration of drug in a total volume of 1 ml. The MIC was determined for the following drugs: ampicillin, pipericillin, temocillin, cephalothin, cefuroxime, cefotaxime, ceftazidime, cefepime, imipenem, meropenem, and aztreonam. To the first well in each row 1 ml of the diluted cell suspension was added, and to all remaining wells per row 0.5 ml of the diluted cell suspension was added. For each row, the predetermined volume of a drug solution was added to the first well per row, mixed well, and then 0.5 ml of the mixed solution was transferred to the next well, and so on until the serial dilutions were completed. From the last well in each row, 0.5 ml was removed so that all well contained 0.5 ml of the drug-containing culture. Plates were sealed with BreatheEasy film (Diversified Biotech, Boston, Mass.) and maintained overnight at 37° C. with shaking. The following day, the MIC was determined by identifying the lowest drug concentration that completely inhibited growth (i.e., the well was clear). The MICs, in µg/ml, for each of the above-identified drugs was as follows: ampicillin, >1024; pipericillin, >1024; temocillin, 32: cephalothin, 1024; cefuroxime, 512; cefotaxime, 8; ceftazidime, 64; cefepime, 1; imipenem, 0.25; meropenem, 0.03125; and aztreonam, 16.

Example 6

Selection of E. coli Containing Improved ampC Mutants

The population of E. coli cells in Example 5 resulted in identifying 8 drugs, ampicillin, pipericillin, cephalothin, cefuroxime, cefotaxime, ceflazidime, cefepime, and aztreonam, where the MICs were at least 4× greater than those of pAmpC0. Cells from the wells containing the highest concentration of each of these drugs (except cephalothin) that supported growth were streaked onto L(tet) medium. Following overnight incubation at 37° C., two or three colonies from each L(tet) plate were resuspended in 500 µl sterile buffer each, and 100 µl was spread from each suspension onto an MH-I plate. Each plate was stamped with a set of 8 antibiotic discs that included pipericillin, cefuroxime, cefotaxime, ceftazidime, cefepime, imipenem, meropenem, and aztreonam.

Based on the sizes of the zones of inhibition, two isolates that gave the greatest resistance were identified and labeled as pAmpC11D and pAmpC12D, respectively.

Plasmids were prepared from those isolates and were transformed into E. coli strain JM109. MICs conferred by each of those plasmids was determined as in Example 5.

Table 1 shows the MICs of plasmids that were prepared in similar previous experiments. Plasmids pAmpC13A and pAmpC41A (first line) and plasmid pAmpC21B (second line) were prepared by a similar method from that described in Examples 3–5. pAmpC11C and pAmpC13C (third line) were prepared by the identical method from that described. It is believed that the method in Examples 4–6 is preferable to previous methods.

pAmpC13A confers improved resistance to ampicillin, pipericillin, temocillin, cefotaxime, ceftazidime, cefepime, meropenem and aztreonam and results in clinical resistance to ampicillin, cephalothin, cefuroxime, pipericillin, temocillin, ceftazidime, and aztreonam. Those improvements in resistance give pAmpC13A a score of 21.5 units distance from PACSE (Table 1), almost doubling its distance from pACSE. The coding sequence of the mutant ampC gene and the mutant AmpC polypeptide of pAmpC13A are provided as SEQ. ID. Nos. 6 and 7, respectively.

Subsequent rounds of mutagenesis and selection resulted in pAmpC41A which has a slight improvement in resistance to pipericillin and a slightly improved distance from pACSE. The coding sequence of the mutant ampC gene and the mutant AmpC polypeptide of pAmpC41A are provided as SEQ. ID. Nos. 8 and 9, respectively.

A second and independent line of evolved mutants was selected from pAmpC0. After two cycles of mutagenesis and selection, the second line yielded pAmpC21B, which confers clinical resistance to ampicillin, cephalothin, cefuroxime, pipericillin, ceflazidime, and aztreonam. The coding sequence of the mutant ampC gene and the mutant AmpC polypeptide of pAmpC21B are provided as SEQ. ID). Nos. 10 and 11, respectively.

These two independent experiments indicate that sexual PCR can reproducibly evolve improved resistance to multiple β-lactam antibiotics.

Example 7

Sequence Analysis of Selected Mutant ampC Genes

As indicated below and as shown in FIGS. 8A–B and FIG. 9, sequence changes are designated as the wildtype base (or amino acid) with a subscript indicating its position in the coding sequence of protein, followed by the mutant base or amino acid. Thus $T_{25}C$ indicates that the T at position 25 is a C in the mutant.

First Mutant Line

As shown in FIGS. 8A–B, AmpC13A has the following mutations: $T_{25}C$, $C_{195}T$, and $A_{907}C$. Only the $A_{907}C$ mutation results in an amino acid replacement, $S_{303}R$ (FIG. 9). Therefore, this mutant necessarily has evolutionary potential.

As shown in FIGS. 8A–B, AmpC41A has the same three mutations as AmpC13A, and in addition has $A_{361}T$, $A_{663}G$, and $T_{1125}C$, of which the $A_{663}G$ results in a $T_{121}S$ amino acid replacement. As shown in FIG. 9, this mutant possess two amino acid replacements.

For this first line of mutants, i.e., AmpC13A and AmpC41A, half of the mutations are silent.

Second Mutant Line

As shown in FIGS. 8A–B, AmpC21B has the following four mutations $A_{587}G$, $T_{702}C$, $T_{869}G$, and $A_{884}G$. Of those only $T_{702}C$ is silent, the other result in three amino acid replacements $Q_{196}R$, L290& and $N_{295}S$ (FIG. 9).

It is notable that the first two independent lines of experiments resulted in none of the same amino acid replacements despite the fact that the MICs of the final products are very similar (Table 1). The major difference is that the pAmpC41A from the first line gave a 128fold improvement in resistance to cefepime, while the pAmpC21B from the second line gave only a 2-fold increase.

Additional Mutant Lines

The third and fourth mutant lines have not yet been subjected to more than one round of mutagenesis and selection, and products of the first round have not yet been sequenced.

Example 8

Determining Evolutionary Potential By Sequential Site-Directed Mutagenesis

To determine the phenotypic effects of each of the amino acid substitutions, the $A_{907}C$, $A_{587}G$, $A_{663}G$, $T_{869}G$, and $A_{884}G$ mutations are being individually introduced into pAmpC0 by site-directed mutagenesis. It is expected that the $A_{907}C$ mutation will result in MICs that are identical to pAmpC13A. The $A_{587}G$, $A_{663}G$, and $As_{84}G$ mutations will also be introduced individually into AmpC13 to determine whether the combination of any of those mutations with $A_{907}C$ will result in increased resistance levels.

MICs of three of the plasmids containing the wildtype AmpC gene into which the above mutations have been introduced have been determined, as shown in Table 2 below.

TABLE 2

MICs of Single-Mutation Plasmids
Created by Site-Directed Mutagenesis

|  | pACSE | pAmpC0 | pAmpC0-305 | PAmpC0-307 | PAmpC0-308 |
|---|---|---|---|---|---|
| Nucleotide Mutation |  |  | A663 to G | T869 to G | A644 to G |
| Amino Acid Substitution |  |  | T121 to S | L290 to R | N295 to S |
| Ampicillin | 2 | 128 | 128 | 128 | 64 |
| Pipericillin | 4 | 16 | 16 | 16 | 4 |
| Temocillin | 16 | 16 | 16 | 8 | 8 |
| Cephalothin | 16 | 1024 | 512 | 512 | 512 |
| Cefuroxime | 16 | 64 | 32 | 32 | 32 |
| Cefotaxime | 0.0625 | 1 | 1 | 0.5 | 0.5 |
| Ceftazidime | 0.5 | 2 | 2 | 1 | 2 |
| Cefepime | 0.03125 | 0.0625 | 0.0625 | 0.0625 | 0.0625 |
| Imipenem | 0.25 | 0.25 | 0.125 | 0.125 | 0.125 |
| Meropenem | 0.00195 | 0.00195 | 0.01563 | 0.03125 | 0.015625 |
| Aztreonam | 0.5 | 4 | 4 | 4 | 4 |
| Distance from pACSE | 0 | 10.5 | 10.3 | 10.2 | 9.2 |

The MIC conferred by the $T_{869}G$ mutation, resulting in the $L_{290}R$ amino acid substitution, is not significantly different from that conferred by the wildtype gene in plasmid pAmpC0, thus that mutation alone is neutral (see Table 2). Similarly, the MIC conferred by the $A_{663}G$ mutation, resulting in $T_{121}S$ substitution is neutral (see Table 2). Both of these essentially neutral mutations do significantly increase resistance to Meropenem and, thus, might be advantageous under conditions where the primary selection is for improved meropenem resistance. The MIC conferred by the $A_{884}G$ mutation, resulting in the $N_{295}S$ amino acid substitution, is significantly worse than that conferred by the wildtype gene in plasmid pAmpC0 (see Table 2), thus that mutation alone is deleterious. Thus, neither the $T_{869}G$ mutation nor the $A_{884}G$ mutation would by likely to selected as the first mutation. in the evolution of AmpC21 B. Whether any of the $A_{907}C$ or $A_{588}G$ mutations confer a selective advantage and, therefore, would be capable of arising in nature remains to be determined. However, because the only amino acid substitution carried by AmpC13 is $S_{303}R$, it can be inferred that pAmpC0 carrying the corresponding $A_{907}C$ substitution is very likely to be selectively advantageous.

Example 9

Determining Whether in vitro Mutagenesis Mimics Natural Evolution

One of the most important aspects of this invention is to provide evidence that the genes evolved in the laboratory accurately reflect the genes that are likely to evolve in nature. Although it cannot be known or predicted with absolute accuracy exactly what will evolve in nature, what has evolved previously in nature is known and the extent to which in vitro evolution (in the laboratory) parallels past evolution will indicate the confidence levels that the present invention provides.

Figure 10:
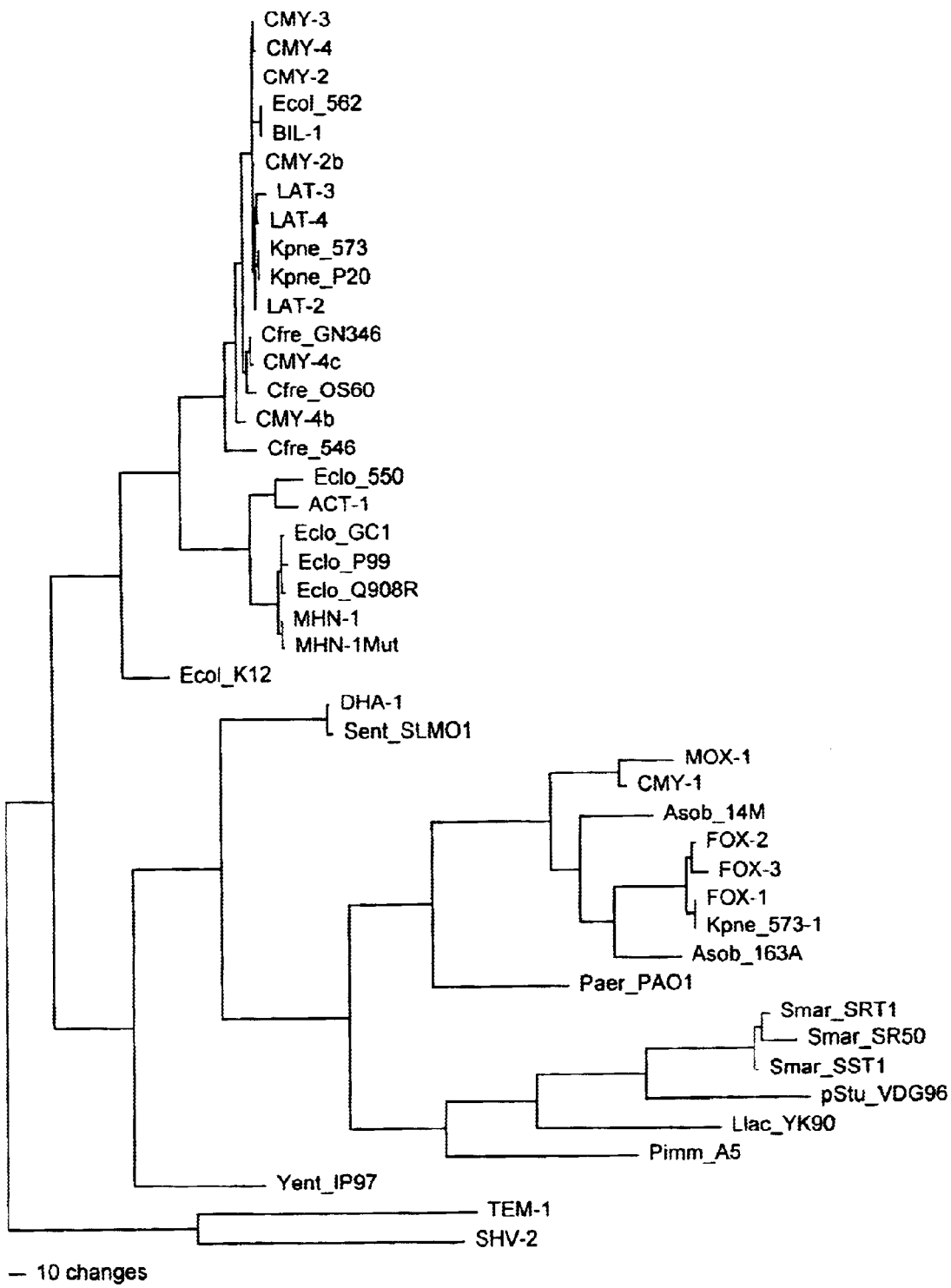
FIG. 10 is a phylogenetic tree of forty-four AmpC genes from different organisms.
Figure 11:
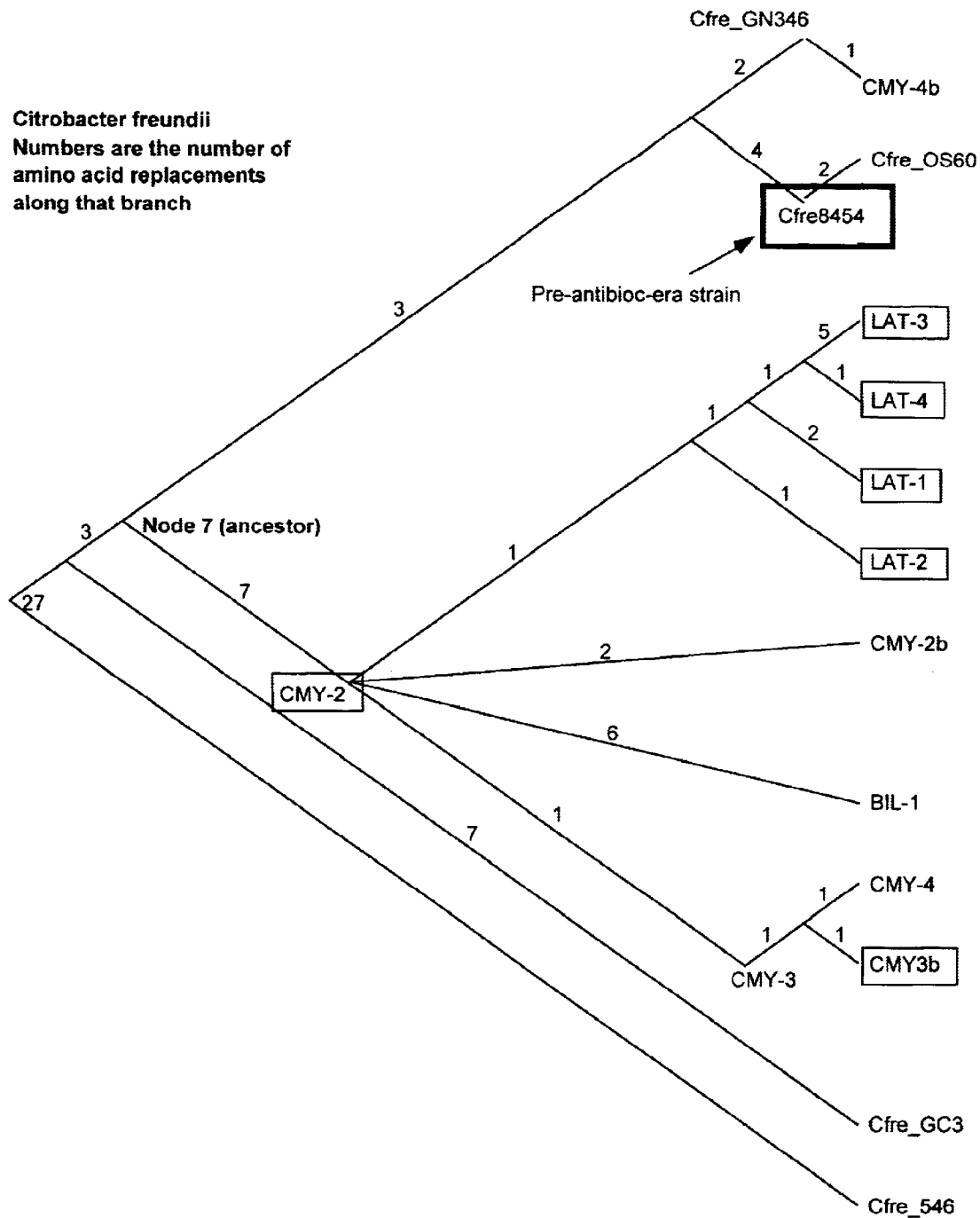
FIG. 11 is an analysis illustrating the sequence variation among AmpC genes that originated from *Citrobacter freundii*.

The sequences of over 50 AmpC genes from clinical isolates are known. Many of those genes are plasmid borne, but some are chromosomal. Phylogenetic analysis (construction of phylogenetic trees) allows one to conclude that the plasmid-borne genes originated from three primary sources: *Citrobacter freundii*, Enterobacter and Pseudomonas species (FIG. 10). The transfer from chromosome to plasmid, and the subsequent spreading of those genes to a variety of Gram negative pathogens has been the result of strong selection due to the heavy use of β-lactam antibiotics. As those genes have spread they have evolved as the result of sequence changes that increased the range of β-lactam antibiotics that they could hydrolyze. A detailed analysis of those sequences that originated from *Citrobacter freundii* allows one to estimate when each of the amino acid replacements occurred along that tree a during evolution (FIG. 11).

Instead of using the *E. coli*K12 wildtype ampC gene, the wildtype ampC from a *Citrobacter freundii* (Cfre) strain that was isolated in the pre-antibiotic era (available from the American Type Culture Collection) will be used. That wildtype gene will not have been subjected to selection for resistance to β-lactam antibiotics. Use of the Cfre ampC will permit direct comparison between the multiply-mutated alleles that are evolved in the laboratory with the alleles that evolved in nature in order to see whether some of the same mutations led to similar resistance phenotypes.

Ten independent lines of the mutagenized ampc gene of *C. freundii* will be established. Each will be subjected to repeated cycles of mutation-selection until no further improvement in resistance levels can be obtained, at which point the best mutant from each line will be isolated, sequenced, back-crossed to eliminate neutral and deleterious mutations, and subjected to Darwinian-selection via stepwise site-directed mutagenesis as described above. The result will be a set of 10 independently-evolved genes, each of which could have evolved in nature.

Convergence is a term used by evolutionary biologists to describe a situation in which genes that appear to be indistinguishable (either phenotypically or at the sequence level) are identical not because they descended from a common ancestor, but because the same solution to a selective challenge evolved independently more than once. Comparison of the ten independent evolutionary lines will permit assessment of convergence at both the phenotypic and sequence levels. Whether isolates are recovered with virtually identical scores and patterns of scores from each of the ten lines, and whether any amino acid replacements are common among the highest scoring mutants in the ten lines will indicate the degree of convergence.

Each of the ten "best" mutants can be thought of as one solution to a problem, the problem being resistance to a set of drugs. Measuring convergence indicates how much the different solutions have in common and suggests something about the variety of solutions that exist in mutation space. The practical application of measuring convergence is that it provides some idea of how many different kinds of genes with significantly improved β-lactamase activity are likely to arise in nature.

The crystal structure of the AmpC β-lactamase has been determined. Existing software accurately predicts the structural changes that result from introduction of specific mutations. It will therefore be possible to generate models of the crystal structures of each of the "best" β-lactamases that have been evolved in the laboratory. It may well be the case that the mutant structures are much more alike than are the mutant sequences themselves. If so, it will simply mean that there are a variety of amino acid substitutions that lead to the same structure with the resulting similar activities.

The fraction of phenotypically indistinguishable sequences that are the same either by sequence or by structure allows us to estimate the number of possible sequences or structures that will produce the same phenotype.

Among the naturally occurring plasmids, CMY-2 (Bauernfeind et al., "Characterization of the Plasmidic Beta-lactamase CMY-2, Which is Responsible for Cephamycin Resistance," *Antimicrob. Agents Chemother.* 40(1):221–224 (1996); Genbank Accession X91 840, which are hereby incorporated by reference) and CMY-2b confer some of the highest levels of resistance to temocillin, cefotaxime, imipenem and meropenem. In order to assure similar levels of gene expression, the ampC genes from each plasmid will be cloned into pACSE2 or pACSE3 and the MIC will be determined for each drug. Because the amino acid replacements that occurred between the wildtype sequence and the plasmid gene sequences can be estimated, as well as the order in which they occurred, it is possible to determine whether evolution in the laboratory followed a pattern similar to that of evolution in nature. A high degree of correspondence between the laboratory patterns and the "natural" patterns will provide good confidence that the laboratory experiments do, in fact, mimic what happens in nature.

Although the invention has been described in detail for the purposes of illustration, it is understood that such detail is solely for that purpose, and variations can be made therein by those skilled in the art without departing from the spirit and scope of the invention which is defined by the following claims.

What is claimed:

1. A method of predicting the evolutionary potential of a mutant resistance gene comprising:

preparing a mutant resistance gene that confers a selectable resistance phenotype to a host cell, said preparing comprising successive rounds of mutagenesis and selection where each of the rounds confers enhancement of the resistance phenotype until clinical resistance is achieved, the mutant resistance gene either including two or more nucleic acid modifications or encoding a mutant polypeptide including two or more amino acid modifications; and determining whether the mutant resistance gene is likely to evolve through two or more independent mutation events, where each independent mutation event confers an enhancement of the resistance phenotype.

2. The method according to claim 1, wherein the mutant resistance gene encodes the mutant polypeptide.

3. The method according to claim 2, wherein each of the two or more amino acid modifications is selected independently from the group consisting of additions, deletions, substitutions, duplications, and rearrangements.

4. The method according to claim 2, wherein said determining comprises:

identifying two or more mutations of the mutant resistance gene which affect the amino acid sequence of the mutant polypeptide;

preparing a first set of singly mutated resistance genes each of which encodes a singly mutated polypeptide consisting of one of the two or more amino acid modifications of the mutant polypeptide;

inserting each of the first set of singly mutated resistance genes individually into one of a first set of host cells; and selecting one or more of the first set of singly mutated resistance genes which confer a selectable enhancement of the resistance phenotype to the host cells of the first set, wherein the absence of any selected singly mutated resistance genes indicates that the mutant resistance gene is unlikely to evolve through independent mutations.

5. The method according to claim 4, wherein said selecting comprises:

introducing the first set of host cells onto a selection media and collecting individual host cells of the first set which grow on the selection media.

6. The method according to claim 5, wherein the selection media comprises at least one antibiotic and the mutant resistance gene is an antibiotic resistance gene.

7. The method according to claim 6, wherein the selection media comprises a plurality of antibiotics.

8. The method according to claim 5, wherein the selection media comprises at least one antiviral agent and the mutant resistance gene is an antiviral resistance gene.

9. The method according to claim 5, wherein the selection media comprises at least one antifungal agent and the mutant resistance gene is an antifungal resistance gene.

10. The method according to claim 5, wherein the selection media comprises at least one antimalarial agent and the mutant resistance gene is an antiprotozoal resistance gene.

11. The method according to claim 4, further comprising:

modifying the selected singly mutated resistance genes, wherein said modifying comprises introducing an additional mutation in the selected singly mutated resistance gene to prepare one or more doubly mutated resistance genes each of which encodes a doubly mutated polypeptide;

inserting each of the one or more doubly mutated resistance genes individually into a second set of host cells; and selecting one or more of the doubly mutated resistance genes which confers a selectable enhancement of the resistance phenotype to the host cells of the second set.

12. The method according to claim 11, wherein said selecting one or more of the doubly mutated resistance genes comprises:

introducing the host cells of the second set onto a selection media and collecting the host cells of the second set which grow on the selection media.

13. The method according to claim 11, further comprising:

repeating the steps of modifying, inserting, selecting, and assessing in succession until each of the two or more mutations of the mutant resistance gene have been recreated, indicating that the mutant resistance gene is likely to evolve through independent mutations.

14. The method according to claim 1, wherein the mutant resistance gene includes two or more nucleic acid modifications, the two or more nucleic acid modifications affecting expression levels of the encoded polypeptide.

15. The method according to claim 14, wherein the two or more nucleic acid modifications are present in a promoter region of the mutant resistance gene.

16. The method according to claim 1, wherein said preparing comprises:

providing a resistance gene;

introducing a plurality of mutations into the resistance gene to produce a mutated resistance gene;

inserting the mutated resistance gene into host cell;

selecting the host cell which exhibits the strongest resistance phenotype;

isolating the mutated resistance gene from the selected host cell; and repeating at least one subsequent round of said providing, introducing, inserting, selecting, and isolating until the mutated resistance gene of a subsequent round exhibits no further enhancement of the resistance phenotype relative to the mutated resistance gene of a preceding round.

17. The method according to claim 16, wherein said introducing is carried out by DNA shuffling, error-prone PCR, or cassette mutagenesis.

18. The method according to claim 16, wherein said inserting is carried out by ligating the mutant resistance gene into a plasmid and treating the host cell under conditions effective to incorporate the plasmid into the host cell.

19. The method according to claim 18, wherein said treating is carried out by electroporation.

20. The method according to claim 18, wherein the plasmid is selected from the group consisting of pACSE, pACSE2, and pACSE3.

21. The method according to claim 1, wherein the host cell is *Escherichia coli*.

22. A method of screening a drug for anti-pathogenic activity against a pathogen including a mutant anti-pathogenic resistance gene, the method comprising:

providing a host cell comprising a mutant anti-pathogenic resistance gene either including two or more nucleic acid modifications or encoding a mutant anti-pathogenic polypeptide which includes two or more amino acid modifications, wherein the mutant anti-pethogenic resistance gene or mutant anti-pathogenic polypeptide confers a selectable advantage to the host cell, the mutant anti-pathogenic resistance gene having been prepared by successive rounds of mutagenesis and selection where each of the rounds confers enhancement of the resistance phenotype until clinical resistance is achieved and having been demonstrated to be likely to evolve through two or more independent mutation events, where each independent mutation event confers an enhancement of the resistance phenotype;

growing the host cell on a selection media comprising a candidate drug or combinations thereof; and determining whether the host cell is capable of growing on the selection media, wherein absence of host cell growth and/or proliferation indicates anti-pathogenic activity for the candidate drug or combination thereof.

23. The method according to claim 22, wherein said providing the host cell comprises:

providing an anti-pathogenic resistance gene;

introducing a plurality of mutations into the anti-pathogenic resistance gene to produce a mutated anti-pathogenic resistance gene;

inserting the mutated anti-pathogenic resistance gene into a host cell;

selecting the host cell which exhibits the strongest resistance phenotype;

isolating the mutated resistance gene from the selected host cell;

repeating said providing, introducing, inserting, selecting, and isolating until the mutated resistance gene of a subsequent round exhibits no further enhancement of the resistance phenotype relative to the mutated resistance gene of a preceding round; and determining whether the mutant resistance gene is likely to evolve through two or more independent mutation events, where each independent mutation event confers an enhancement of the resistance phenotype.

24. The method according to claim 23, wherein the mutant anti-pathogenic resistance gene includes two or more nucleic acid modifications.

25. The method according to claim 24, wherein the two or more nucleic acid modifications are present in a promoter region.

26. The method according to claim 23, wherein the mutant anti-pathogenic resistance gene encodes the anti-pathogenic polypeptide.

27. The method according to claim 23, wherein said introducing is carried out by DNA shuffling, error-prone PCR, or cassette mutagenesis.

28. The method according to claim 23, wherein said inserting is carried out by ligating the mutated anti-pathogenic resistance gene into a plasmid and treating the host cell under conditions effective to incorporate the plasmid into the host cell.

29. The method according to claim 23, wherein said inserting is carried out by ligating the mutant anti-pathogenic resistance gene into a plasmid and treating the host cell under conditions effective to incorporate the plasmid into the host cell.

30. The method according to claim 28, wherein the plasmid is selected from the group consisting of pACSE, pACSE2, and pACSE3.

31. The method according to claim 22, wherein the host cell is *Escherichia coli*.

32. The method according to claim 22, wherein the anti-pathogenic resistance gene and mutant anti-pathogenic resistance genes are selected from the group consisting of (i) antibiotic resistance gene and mutant antibiotic resistance gene, (ii) anti-viral resistance gene and mutant anti-viral resistance gene, (iii) anti-fungal resistance gene and mutant anti-fungal resistance gene, and (iv) anti-protozoal gene and resistance mutant anti-protozoal resistance gene.

33. A method of assessing the potential longevity of a candidate anti-pathogenic drug comprising:

providing a resistance gene encoding a polypeptide which is ineffective against a candidate anti-pathogenic drug;

introducing multiple mutations into the resistance gene to produce a mutant resistance gene which encodes a mutant polypeptide including two or more amino acid modifications, wherein the mutant polypeptide is effective against the candidate anti-pathogenic drug;

determining the minimum number of mutations required to overcome the activity of the candidate anti-pathogenic drug, wherein the greater the minimum number of mutations, the greater the potential longevity of the candidate anti-pathogenic drug.

34. The method according to claim 33, wherein the resistance gene and the mutant resistance gene are selected from the group consisting of (i) antibiotic resistance gene and mutant antibiotic resistance gene, (ii) anti-viral resistance gene and mutant anti-viral resistance gene, (iii) anti-fungal resistance gene and mutant anti-fungal resistance gene, and (iv) anti-protozoal resistance gene and mutant anti-protozoal resistance gene.

35. The method according to claim 33, wherein said introducing is carried out by DNA shuffling, error-prone PCR, or cassette mutagenesis.

36. The method according to claim 33 further comprising after said introducing:

inserting the mutant resistance gene into a host cell; and assaying whether the host cell can survive when grown on a selection media comprising the candidate anti-pathogenic drug, wherein survival of the host cell indicates that the mutant polypeptide is effective against the candidate anti-pathogenic drug.

37. The method according to claim 36, wherein said inserting is carried out by ligating the mutant resistance gene into a plasmid and treating the host cell under conditions effective to incorporate the plasmid into the host cell.

38. The method according to claim 37, wherein said treating is carried out by electroporation.

39. The method according to claim 33, wherein said determining comprises:

identifying the two or more amino acid modifications of the mutant polypeptide;

preparing a plurality of singly mutated resistance genes each of which encodes a singly mutated polypeptide, the singly mutated polypeptide consisting of one of the two or more amino acid modifications of the mutant polypeptide;

inserting each of the plurality of singly mutated resistance genes individually into a first set of host cells; and assaying whether any of the first set of host cells can survive when grown on a selection media comprising the candidate anti-pathogenic drug, wherein survival of any of the first set of host cells indicates that a single mutational event is all that is required to overcome the efficacy of the candidate anti-pathogenic drug.

40. The method according to claim 39, further comprising:

modifying the selected singly mutated resistance genes, wherein said modifying comprises introducing an additional mutation into each of the singly mutated resistance genes to prepare one or more doubly mutated resistance genes each of which encodes a doubly mutated polypeptide, the doubly mutated polypeptide consisting of two of the two or more modifications of the mutant polypeptide;

second inserting each of the one or more doubly mutated genes into a second set of host cells; and assaying whether any of the second set of host cells can survive when grown on the selection media comprising the candidate anti-pathogenic drug, wherein survival of any of the host cells indicates that two mutational events are all that is required to overcome the efficacy of the candidate anti-pathogenic drug.

41. The method according to claim 40, further comprising:

optionally repeating the steps of modifying, second inserting, and assaying in succession until each of the mutations of the mutant resistance gene have been recreated, indicating that each of the two or more amino acid modifications of the mutant polypeptide are required to overcome the efficacy of the candidate anti-pathogenic drug.

\* \* \* \* \*

SEQUENCE LISTING

<160> NUMBER OF SEQ ID NOS: 17

<210> SEQ ID NO 1
<211> LENGTH: 3801
<212> TYPE: DNA
<213> ORGANISM: Artificial Sequence
<220> FEATURE:
<223> OTHER INFORMATION: Description of Artificial Sequence: plasmid pACSE

<400> SEQUENCE: 1

```
cgtatggcaa tgaaagacgg tgagctggtg atatgggata gtgttcaccc ttgttacacc      60
gttttccatg agcaaactga aacgttttca tcgctctgga gtgaatacca cgacgatttc     120
cggcagtttc tacacatata ttcgcaagat gtggcgtgtt acggtgaaaa cctggcctat     180
ttccctaaag ggtttattga gaatatgttt ttcgtctcag ccaatccctg ggtgagtttc     240
accagttttg atttaaacgt ggccatcatg tttgacagct tatcatcgac tgcacggtgc     300
accaatgctt ctggcgtcag gcagccatcg gaagctgtgg tatggctgtg caggtcgtaa     360
atcactgcat aattcgtgtc gctcaaggcg cactcccgtt ctggataatg ttttttgcgc     420
cgacatcata acggttctgg caaatattct gaaatgagct gttgacaatt aatcatccgg     480
ctcgtataat gtgtggaatt gtgagcggat aacaatttca cacaggaaac agaccatggc     540
tggtgaccac gtcgtggaat gccttcgaat tcagcacctg cacatgggac gtcgacctga     600
ggtaattata acccgggccc tatatatgga tccaattgca atgatcatca tgacagatct     660
gcgcgcgatc gatatcagcg ctttaaattt gcgcatgcta gctatagttc tagaggtacc     720
ggttgttaac gttagccggc tacgtatact ccggaatatt aataggccta ggatgcatat     780
ggcggccgcc tgcagctggc gccatcgata cgcgtacgtc gcgaccgcgg acatgtacag     840
agctcgagaa gtactagtgg ccaggaccca acgctgcccg agatgcgccg cgtgcggctg     900
ctggagatgg cggacgcgat ggatatgttc tgccaagggt tggtttgcgc attcacagtt     960
```

-continued

```
ctccgcaaga attgattggc tccaattctt ggagtggtga atccgttagc gaggtgccgc    1020
cggcttccat tcaggtcgag gtggcccggc tccatgcacc gcgacgcaac gcggggaggc    1080
agacaaggta tagggcggcg cctacaatcc atgccaaccc gttccatgtg ctcgccgagg    1140
cggcataaat cgccgtgacg atcagcggtc cagtgatcga agttaggctg gtaagagccg    1200
cgagcgatcc ttgaagctgt ccctgatggt cgtcatctac ctgcctggac agcatggcct    1260
gcaacgcggg catcccgatg ccgccggaag cgagaagaat cataatgggg aaggccatcc    1320
agcctcgcgt cgcgaacgcc agcaagacgt agcccagcgc gtcggccgcc atgccggcga    1380
taatggcctg cttctcgccg aaacgtttgg tggcgggacc agtgacgaag gcttgagcga    1440
gggcgtgcaa gattccgaat accgcaagcg acaggccgat catcgtcgcg ctccagcgaa    1500
agcggtcctc gccgaaaatg acccagagcg ctgccggcac ctgtcctacg agttgcatga    1560
taaagaagac agtcataagt gcggcgacga tagtcatgcc ccgcgcccac cggaaggagc    1620
tgactgggtt gaaggctctc aagggcatcg gtcgacgctc tcccttatgc gactcctgca    1680
ttaggaagca gcccagtagt aggttgaggc cgttgagcac cgccgccgca aggaatggtg    1740
catgcaagga gatggcgccc aacagtcccc cggccacggg gcctgccacc atacccacgc    1800
cgaaacaagc gctcatgagc ccgaagtggc gagcccgatc ttccccatcg gtgatgtcgg    1860
cgatataggc gccagcaacc gcacctgtgg cgccggtgat gccggccacg atgcgtccgg    1920
cgtagaggat ccacaggacg ggtgtggtcg ccatgatcgc gtagtcgata gtggctccaa    1980
gtagcgaagc gagcaggact gggcggcggc caaagcggtc ggacagtgct ccgagaacgg    2040
gtgcgcatag aaattgcatc aacgcatata gcgctagcag cacgccatag tgactggcga    2100
tgctgtcgga atggacgata tcccgcaaga ggcccggcag taccggcata accaagccta    2160
tgcctacagc atccaggtg acggtgccga ggatgacgat gagcgcattg ttagatttca    2220
tacacggtgc ctgactgcgt tagcaattta actgtgataa actaccgcat taaagcttat    2280
cgatgataag ctgtcaaaca tgagaattac aacttatatc gtatgggct gacttcaggt    2340
gctacatttg aagagataaa ttgcactgaa atctagaaat attttatctg attaataaga    2400
tgatcttctt gagatcgttt tggtctgcgc gtaatctctt gctctgaaaa cgaaaaaacc    2460
gccttgcagg gcggttttc gaaggttctc tgagctacca actctttgaa ccgaggtaac    2520
tggcttggag gagcgcagtc accaaaactt gtcctttcag tttagcctta accggcgcat    2580
gacttcaaga ctaactcctc taaatcaatt accagtggct gctgccagtg gtgcttttgc    2640
atgtctttcc gggttggact caagacgata gttaccggat aaggcgcagc ggtcggactg    2700
aacgggggt tcgtgcatac agtccagctt ggagcgaact gcctacccgg aactgagtgt    2760
caggcgtgga atgagacaaa cgcggccata acagcggaat gacaccggta aaccgaaagg    2820
caggaacagg agagcgcacg agggagccgc caggggaaa cgcctggtat ctttatagtc    2880
ctgtcgggtt tcgccaccac tgatttgagc gtcagatttc gtgatgcttg tcagggggc    2940
ggagcctatg gaaaaacggc tttgccgcgg ccctctcact tccctgttaa gtatcttcct    3000
ggcatcttcc aggaaatctc cgccccgttc gtaagccatt tccgctcgcc gcagtcgaac    3060
gaccgagcgt agcgagtcag tgagcgagga agcggaatat atcctgtatc acatattctg    3120
ctgacgcacc ggtgcagcct tttttctcct gccacatgaa gcacttcact gacaccctca    3180
tcagtgccaa catagtaagc cagtatacac tccgctagcg ctgatgtccg gcggtgcttt    3240
tgccgttacg caccaccccg tcagtagctg aacaggaggg acagctgata gaaacagaag    3300
ccactggagc acctcaaaaa caccatcata cactaaatca gtaagttggc agcatcaccc    3360
```

| | |
|---|---:|
| gacgcacttt gcgccgaata atacctgtg acggaagatc acttcgcaga ataaataaat | 3420 |
| cctggtgtcc ctgttgatac cgggaagccc tgggccaact tttggcgaaa atgagacgtt | 3480 |
| gatcggcacg taagaggttc caactttcac cataatgaaa taagatcact accgggcgta | 3540 |
| ttttttgagt tatcgagatt ttcaggagct aaggaagcta aaatggagaa aaaaatcact | 3600 |
| ggatatacca ccgttgatat atcccaatgg catcgtaaag aacattttga ggcatttcag | 3660 |
| tcagttgctc aatgtaccta taaccagacc gttcagctgg atattacggc cttttttaaag | 3720 |
| accgtaaaga aaaataagca caagtttttat ccggcctttta ttcacattct tgcccgcctg | 3780 |
| atgaatgctc atccggaatt c | 3801 |

<210> SEQ ID NO 2
<211> LENGTH: 5201
<212> TYPE: DNA
<213> ORGANISM: Artificial Sequence
<220> FEATURE:
<223> OTHER INFORMATION: Description of Artificial Sequence: plasmid pACSE2

<400> SEQUENCE: 2

| | |
|---|---:|
| cgtatggcaa tgaaagacgg tgagctggtg atatgggata gtgttcaccc ttgttacacc | 60 |
| gttttccatg agcaaactga acgttttca tcgctctgga gtgaatacca cgacgatttc | 120 |
| cggcagtttc tacacatata ttcgcaagat gtggcgtgtt acggtgaaaa cctggcctat | 180 |
| ttccctaaag ggtttattga gaatatgttt ttcgtctcag ccaatccctg ggtgagtttc | 240 |
| accagttttg atttaaacgt ggccatcatg tttgacagct tatcatcgac tgcacggtgc | 300 |
| accaatgctt ctggcgtcag gcagccatcg gaagctgtgg tatggctgtg caggtcgtaa | 360 |
| atcactgcat aattcgtgtc gctcaaggcg cactcccgtt ctggataatg tttttttgcgc | 420 |
| cgacatcata acggttctgg caaatattct gaaatgagct gttgacaatt aatcatccgg | 480 |
| ctcgtataat gtgtggaatt gtgagcggat aacaatttca cacaggaaac agaccatggc | 540 |
| tggtgaccac gtcgtggaat gccttcgaat tcagcacctg cacatgggac gtcgacctga | 600 |
| ggtaattata acccgggccc tatatatgga tccaattgca atgatcatca tgacagatct | 660 |
| gcgcgcgatc gatatcagcg ctttaaattt gcgcatgcta gctatagttc tagaggtacc | 720 |
| ggttgttaac gttagccggc tacgtatact ccggaatatt aataggccta ggatgcatat | 780 |
| ggcggccgcc tgcagctggc gccatcgata cgcgtacgtc gcgaccgcgg acatgtacag | 840 |
| agctcgagaa gtactagttt acgttgacac catcgaatgg cgcaaaacct ttcgcggtat | 900 |
| ggcatgatag cgcccggaag agagtcaatt cagggtggtg aatgtgaaac cagtaacgtt | 960 |
| atacgatgtc gcagagtatg ccggtgtctc ttatcagacc gtttcccgcg tggtgaacca | 1020 |
| ggccagccac gtttctgcga aaacgcggga aaaagtggaa gcggcgatgg cggagctgaa | 1080 |
| ttacattccc aaccgcgtgg cacaacaact ggcgggcaaa cagtcgttgc tgattggcgt | 1140 |
| tgccacctcc agtctggccc tgcacgcgcc gtcgcaaatt gtcgcggcga ttaaatctcg | 1200 |
| cgccgatcaa ctgggtgcca gcgtggtggt gtcgatggta gaacgaagcg gcgtcgaagc | 1260 |
| ctgtaaagcg gcggtgcaca atcttctcgc gcaacgcgtc agtgggctga tcattaacta | 1320 |
| tccgctggat gaccaggatg ccattgctgt ggaagctgcc tgcactaatg ttccggcgtt | 1380 |
| atttcttgat gtctctgacc agacacccat caacagtatt attttctccc atgaagacgg | 1440 |
| tacgcgactg ggcgtggagc atctggtcgc attgggtcac cagcaaatcg cgctgttagc | 1500 |
| gggcccatta agttctgtct cggcgcgtct gcgtctggct ggctggcata aatatctcac | 1560 |

```
tcgcaatcaa attcagccga tagcggaacg ggaaggcgac tggagtgcca tgtccggttt    1620
tcaacaaacc atgcaaatgc tgaatgaggg catcgttccc actgcgatgc tggttgccaa    1680
cgatcagatg gcgctgggcg caatgcgcgc cattaccgag tccgggctgc gcgttggtgc    1740
ggatatctcg gtagtgggat acgacgtatac cgaagacagc tcatgttata tcccgccgtc    1800
aaccaccatc aaacaggatt tcgcctgct ggggcaaacc agcgtggacc gcttgctgca     1860
actctctcag ggccaggcgg tgaagggcaa tcagctgttg cccgtctcac tggtgaaaag    1920
aaaaaccacc ctggcgccca atacgcaaac cgcctctccc cgcgcgttgg ccgattcatt    1980
aatgcagctg gcacgacagg tttcccgact ggaaagcggg cagtgagcgc aacgcaatta    2040
atgtgagtta gcgcgaattg atctgaattc tcatgtttga cagcttatca tcgactgcac    2100
ggtgcaccaa tgcttctggc gtcaggcagc catcggaagc tgtggtatgg ctgtgcaggt    2160
cgtaaatcac tgcataattc gtgtcgctca aggcgcactc ccgttctgga taatgttttt    2220
tgcgccgaca tcataacggt tctggcaaat attctagtgg ccaggaccca acgctgcccg    2280
agatgcgccg cgtgcggctg ctggagatgg cggacgcgat ggatatgttc tgccaagggt    2340
tggtttgcgc attcacagtt ctccgcaaga attgattggc tccaattctt ggagtggtga    2400
atccgttagc gaggtgccgc cggcttccat tcaggtcgag gtggcccggc tccatgcacc    2460
gcgacgcaac gcggggaggc agacaaggta tagggcggcg cctacaatcc atgccaaccc    2520
gttccatgtg ctcgccgagg cggcataaat cgccgtgacg atcagcggtc cagtgatcga    2580
agttaggctg gtaagagccg cgagcgatcc ttgaagctgt ccctgatggt cgtcatctac    2640
ctgcctggac agcatggcct gcaacgcggg catcccgatg ccgccggaag cgagaagaat    2700
cataatgggg aaggccatcc agcctcgcgt cgcgaacgcc agcaagacgt agcccagcgc    2760
gtcggccgcc atgccggcga taatggcctg cttctcgccg aaacgtttgg tggcgggacc    2820
agtgacgaag gcttgagcga gggcgtgcaa gattccgaat accgcaagcg acaggccgat    2880
catcgtcgcg ctccagcgaa agcggtcctc gccgaaaatg acccagagcg ctgccggcac    2940
ctgtcctacg agttgcatga taaagaagac agtcataagt gcggcgacga tagtcatgcc    3000
ccgcgcccac cggaaggagc tgactgggtt gaaggctctc aagggcatcg gtcgacgctc    3060
tcccttatgc gactcctgca ttaggaagca gcccagtagt aggttgaggc cgttgagcac    3120
cgccgccgca aggaatggtg catgcaagga gatggcgccc aacagtcccc cggccacggg    3180
gcctgccacc atacccacgc cgaaacaagc gctcatgagc ccgaagtggc gagcccgatc    3240
ttccccatcg gtgatgtcgg cgatataggc gccagcaacc gcacctgtgg cgccggtgat    3300 gccgccacg atgcgtccgg cgtagaggat ccacaggacg ggtgtggtcg ccatgatcgc    3360
gtagtcgata gtggctccaa gtagcgaagc gagcaggact gggcggcggc caaagcggtc    3420
ggacagtgct ccgagaacgg gtgcgcatag aaattgcatc aacgcatata gcgctagcag    3480
cacgccatag tgactggcga tgctgtcgga atggacgata tcccgcaaga ggcccggcag    3540
taccggcata accaagccta tgcctacagc atccagggtg acgtgccga ggatgacgat     3600 gagcgcattg ttagatttca tacacggtgc ctgactgcgt tagcaattta actgtgataa    3660
actaccgcat taaagcttat cgatgataag ctgtcaaaca tgagaattac aacttatatc    3720
gtatggggct gacttcaggt gctacatttg aagagataaa ttgcactgaa atctagaaat    3780 atttttatctg attaataaga tgatcttctt gagatcgttt tggtctgcgc gtaatctctt    3840
gctctgaaaa cgaaaaaacc gccttgcagg gcggttttttc gaaggttctc tgagctacca    3900
```

```
actctttgaa ccgaggtaac tggcttggag gagcgcagtc accaaaactt gtcctttcag    3960
tttagcctta accggcgcat gacttcaaga ctaactcctc taaatcaatt accagtggct    4020
gctgccagtg gtgcttttgc atgtctttcc gggttggact caagacgata gttaccggat    4080
aaggcgcagc ggtcggactg aacgggggt tcgtgcatac agtccagctt ggagcgaact     4140
gcctacccgg aactgagtgt caggcgtgga atgagacaaa cgcggccata acagcggaat    4200
gacaccggta aaccgaaagg caggaacagg agagcgcacg agggagccgc caggggaaa    4260 cgcctggtat ctttatagtc ctgtcgggtt tcgccaccac tgatttgagc gtcagatttc    4320
gtgatgcttg tcagggggc ggagcctatg gaaaaacggc tttgccgcgg ccctctcact     4380
tccctgttaa gtatcttcct ggcatcttcc aggaaatctc cgccccgttc gtaagccatt    4440
tccgctcgcc gcagtcgaac gaccgagcgt agcgagtcag tgagcgagga agcggaatat    4500
atcctgtatc acatattctg ctgacgcacc ggtgcagcct ttttctcct gccacatgaa     4560 gcacttcact gacaccctca tcagtgccaa catagtaagc cagtatacac tccgctagcg    4620
ctgatgtccg gcggtgcttt tgccgttacg caccaccccg tcagtagctg aacaggaggg    4680
acagctgata gaaacagaag ccactggagc acctcaaaaa caccatcata cactaaatca    4740
gtaagttggc agcatcaccc gacgcacttt gcgccgaata atacctgtg acggaagatc     4800 acttcgcaga ataaataaat cctggtgtcc ctgttgatac cgggaagccc tgggccaact    4860
tttggcgaaa atgagacgtt gatcggcacg taagaggttc caactttcac cataatgaaa    4920
taagatcact accgggcgta ttttttgagt tatcgagatt tcaggagct aaggaagcta     4980 aaatggagaa aaaaatcact ggatatacca ccgttgatat atcccaatgg catcgtaaag    5040
aacattttga ggcatttcag tcagttgctc aatgtaccta taaccagacc gttcagctgg    5100
atattacggc cttttaaag accgtaaaga aaataagca caagttttat ccggccttta     5160
ttcacattct tgcccgcctg atgaatgctc atccggaatt c                       5201
```

<210> SEQ ID NO 3
<211> LENGTH: 5201
<212> TYPE: DNA
<213> ORGANISM: Artificial Sequence
<220> FEATURE:
<223> OTHER INFORMATION: Description of Artificial Sequence: plasmid pACSE3

<400> SEQUENCE: 3

```
cgtatggcaa tgaaagacgg tgagctggtg atatgggata gtgttcaccc ttgttacacc     60
gttttccatg agcaaactga aacgttttca tcgctctgga gtgaatacca cgacgatttc    120
cggcagtttc tacacatata ttcgcaagat gtggcgtgtt acgtgaaaa cctggcctat     180 ttccctaaag ggtttattga gaatatgttt ttcgtctcag ccaatccctg ggtgagtttc    240
accagttttg atttaaacgt ggccatcatg tttgacagct tatcatcgac tgcacggtgc    300
accaatgctt ctggcgtcag gcagccatcg gaagctgtgg tatggctgtg caggtcgtaa    360
atcactgcat aattcgtgtc gctcaaggcg cactcccgtt ctggataatg ttttttgcgc    420
cgacatcata acggttctgg caaatattct gaaatgagct gttgacaatt aatcatccgg    480
ctcgtataat gtgtggaatt gtgagcggat aacaatttca caggaaaac agatcatgac    540 tggtgaccac gtcgtggaat gccttcgaat tcagcacctg cacatgggac gtcgacctga    600
ggtaattata acccgggccc tatatatgga tccaattgca atgatcatca tgtcagatct    660
gcgcgcgatc gatatcagcg ctttaaattt gcgcatgcta gctatagttc tagaggtacc    720
```

-continued

| | |
|---|---|
| ggttgttaac gttagccggc tacgtatact ccggaatatt aataggccta ggatgcatat | 780 |
| ggcggccgcc tgcagctggc gccatcgata cgcgtacgtc gcgaccgcgg acatgtacag | 840 |
| agctcgagaa gtactagttt acgttgacac catcgaatgg cgcaaaacct ttcgcggtat | 900 |
| ggcatgatag cgcccggaag agagtcaatt cagggtggtg aatgtgaaac cagtaacgtt | 960 |
| atacgatgtc gcagagtatg ccggtgtctc ttatcagacc gtttcccgcg tggtaaacca | 1020 |
| ggccagccac gtttctgcga aaacgcggga aaaagtggaa gcggcgatgg cggagctgaa | 1080 |
| ttacattccc aaccgcgtgg cacaacaact ggcgggcaaa cagtcgttgc tgattggcgt | 1140 |
| tgccacctcc agtctggccc tgcacgcgcc gtcgcaaatt gtcgcggcga ttaaatctcg | 1200 |
| cgccgatcaa ctgggtgcca gcgtggtggt gtcgatggta gaacgaagcg gcgtcgaagc | 1260 |
| ctgtaaagcg gcggtgcaca atcttctcgc gcaacgcgtc agtgggctga tcattaacta | 1320 |
| tccgctggat gaccaggatg ccattgctgt ggaagctgcc tgcactaatg ttccggcgtt | 1380 |
| atttcttgat gtctctgacc agacacccat caacagtatt attttctccc atgaagacgg | 1440 |
| tacgcgactg ggcgtggagc atctggtcgc attgggtcac cagcaaatcg cgctgttagc | 1500 |
| gggcccatta agttctgtct cggcgcgtct gcgtctggct ggctggcata aatatctcac | 1560 |
| tcgcaatcaa attcagccga tagcggaacg ggaaggcgac tggagtgcca tgtccggttt | 1620 |
| tcaacaaacc atgcaaatgc tgaatgaggg catcgttccc actgcgatgc tggttgccaa | 1680 |
| cgatcagatg gcgctgggcg caatgcgcgc cattaccgag tccgggctgc gcgttggtgc | 1740 |
| ggatatctcg gtagtgggat acgacgtatc cgaagacagc tcatgttata tccgccgtc | 1800 |
| aaccaccatc aaacaggatt ttcgcctgct ggggcaaacc agcgtggacc gcttgctgca | 1860 |
| actctctcag ggccaggcgg tgaagggcaa tcagctgttg cccgtctcac tggtgaaaag | 1920 |
| aaaaaccacc ctggcgccca atacgcaaac cgcctctccc cgcgcgttgg ccgattcatt | 1980 |
| aatgcagctg gcacgacagg tttcccgact ggaaagcggg cagtgagcgc aacgcaatta | 2040 |
| atgtgagtta gcgcgaattg atctgaattc tcatgtttga cagcttatca tcgactgcac | 2100 |
| ggtgcaccaa tgcttctggc gtcaggcagc catcggaagc tgtggtatgg ctgtgcaggt | 2160 |
| cgtaaatcac tgcataattc gtgtcgctca aggcgcactc ccgttctgga taatgttttt | 2220 |
| tgcgccgaca tcataacggt tctggcaaat attctagtgg ccaggaccca acgctgcccg | 2280 |
| agatgcgccg cgtgcggctg ctggagatgg cggacgcgat ggatatgttc tgccaagggt | 2340 |
| tggtttgcgc attcacagtt ctccgcaaga attgattggc tccaattctt ggagtggtga | 2400 |
| atccgttagc gaggtgccgc cggcttccat tcaggtcgag gtggcccggc tccatgcacc | 2460 |
| gcgacgcaac gcggggaggc agacaaggta tagggcggcg cctacaatcc atgccaaccc | 2520 |
| gttccatgtg ctcgccgagg cggcataaat cgccgtgacg atcagcggtc cagtgatcga | 2580 |
| agttaggctg gtaagagccg cgagcgatcc ttgaagctgt ccctgatggt cgtcatctac | 2640 |
| ctgcctggac agcatggcct gcaacgcggg catcccgatg ccgccggaag cgagaagaat | 2700 |
| cataatgggg aaggccatcc agcctcgcgt cgcgaacgcc agcaagacgt agcccagcgc | 2760 |
| gtcggccgcc atgccggcga taatggcctg cttctcgccg aaacgtttgg tggcgggacc | 2820 |
| agtgacgaag gcttgagcga gggcgtgcaa gattccgaat accgcaagcg acaggccgat | 2880 |
| catcgtcgcg ctccagcgaa agcggtcctc gccgaaaatg acccagagcg ctgccggcac | 2940 |
| ctgtcctacg agttgcatga taaagaagac agtcataagt gcggcgacga tagtcatgcc | 3000 |
| ccgcgcccac cggaaggagc tgactgggtt gaaggctctc aagggcatcg gtcgacgctc | 3060 |
| tcccttatgc gactcctgca ttaggaagca gcccagtagt aggttgaggc cgttgagcac | 3120 |

```
cgccgccgca aggaatggtg catgcaagga gatggcgccc aacagtcccc cggccacggg      3180
gcctgccacc atacccacgc cgaaacaagc gctcatgtgc ccgaagtggc gagcccgatc      3240
ttccccatcg gtgatgtcgg cgatataggc gccagcaacc gcacctgtgg cgccggtgat      3300
gccggccacg atgcgtccgg cgtagaggat ccacaggacg ggtgtggtcg ccatgatcgc      3360
gtagtcgata gtggctccaa gtagcgaagc gagcaggact gggcggcggc caaagcggtc      3420
ggacagtgct ccgagaacgg gtgcgcatag aaattgcatc aacgcatata gcgctagcag      3480
cacgccatag tgactggcga tgctgtcgga atggacgata tcccgcaaga ggcccggcag      3540
taccggcata accaagccta tgcctacagc atccagggtg acggtgccga ggatgacgat      3600
gagcgcattg ttagatttca tacacggtgc ctgactgcgt tagcaattta actgtgataa      3660
actaccgcat taaagcttat cgatgataag ctgtcaaaca tgagaattac aacttatatc      3720 gtatgggct gacttcaggt gctacatttg aagagataaa ttgcactgaa atctagaaat      3780
attttatctg attaataaga tgatcttctt gagatcgttt tggtctgcgc gtaatctctt      3840
gctctgaaaa cgaaaaaacc gccttgcagg gcggttttc gaaggttctc tgagctacca      3900
actctttgaa ccgaggtaac tggcttggag gagcgcagtc accaaaactt gtcctttcag      3960
tttagcctta accggcgcat gacttcaaga ctaactcctc taaatcaatt accagtggct      4020
gctgccagtg gtgcttttgc atgtctttcc gggttggact caagacgata gttaccggat      4080
aaggcgcagc ggtcggactg aacgggggt tcgtgcatac agtccagctt ggagcgaact      4140
gcctacccgg aactgagtgt caggcgtgga atgagacaaa cgcggccata acagcggaat      4200
gacaccggta aaccgaaagg caggaacagg agagcgcacg agggagccgc caggggggaaa      4260 cgcctggtat ctttatagtc ctgtcgggtt tcgccaccac tgatttgagc gtcagatttc      4320
gtgatgcttg tcagggggc ggagcctatg gaaaaacggc tttgccgcgg ccctctcact      4380
tccctgttaa gtatcttcct ggcatcttcc aggaaatctc cgccccgttc gtaagccatt      4440
tccgctcgcc gcagtcgaac gaccgagcgt agcgagtcag tgagcgagga agcggaatat      4500
atcctgtatc acatattctg ctgacgcacc ggtgcagcct tttttctcct gccacatgaa      4560
gcacttcact gacaccctca tcagtgccaa catagtaagc cagtatacac tccgctagcg      4620
ctgatgtccg gcggtgcttt tgccgttacg caccaccccg tcagtagctg aacaggaggg      4680
acagctgata gaaacagaag ccactggagc acctcaaaaa caccatcata cactaaatca      4740
gtaagttggc agcatcaccc gacgcacttt gcgccgaata aatacctgtg acggaagatc      4800
acttcgcaga ataaataaat cctggtgtcc ctgttgatac cgggaagccc tgggccaact      4860
tttggcgaaa atgagacgtt gatcggcacg taagaggttc aactttcac cataatgaaa      4920 taagatcact accgggcgta ttttttgagt tatcgagatt ttcaggagct aaggaagcta      4980
aaatggagaa aaaaatcact ggatatacca ccgttgatat atcccaatgg catcgtaaag      5040
aacattttga ggcatttcag tcagttgctc aatgtaccta taaccagacc gttcagctgg      5100
atattacggc cttttttaaag accgtaaaga aaaataagca caagttttat ccggccttta      5160
ttcacattct tgcccgcctg atgaatgctc atccggaatt c                         5201
```

<210> SEQ ID NO 4
<211> LENGTH: 1134
<212> TYPE: DNA
<213> ORGANISM: Unknown Organism
<220> FEATURE:
<223> OTHER INFORMATION: Description of Unknown Organism: Escherichia coli plasmid pBR322

-continued

<400> SEQUENCE: 4

```
atggtcaaaa cgacgctctg cgccttatta attaccgcct cttgctccac atttgctgcc     60
cctcaacaaa tcaacgatat tgtgcatcgc acaattaccc gcttataga gcaacaaaag    120
atcccgggta tggcggtggc ggtaatttat cagggtaaac cttattactt tacctgggc    180
tatgcggaca tcgccaaaaa gcagcccgtc acacagcaaa cgttgtttga gttaggttcg    240
gtcagcaaaa catttactgg cgtgcttggt ggcgacgcta ttgctcgagg ggaaatcaag    300
ttaagcgatc ccacaacaaa atactggcct gaacttaccg ctaaacagtg gaatgggatc    360
acactattac atctcgcaac ctacactgct ggcggcctgc cattgcaggt gccggatgag    420
gtgaaatcct caagcgactt gctgcgcttc tatcaaaact ggcagcctgc atgggctcca    480
ggaacacaac gtctgtatgc caactccagt atcggtttgt tcggcgcact ggctgtgaag    540
ccgtctggtt tgagttttga gcaggcgatg caaactcgtg tcttccagcc actcaaactc    600
aaccatacgt ggattaatgt accgcccgca gaagaaaaga ttacgcctg gggatatcgc    660
gaaggtaagg cagtgcatgt ttcgcctggg gcgttagatg ctgaagctta tggtgtgaag    720
tcgaccattg aagatatggc ccgctgggtg caaagcaatt taaaccccct tgatatcaat    780
gagaaaacgc ttcaacaagg gatacaactg gcacaatctc gctactggca aaccggcgat    840
atgtatcagg gcctgggctg ggaaatgctg gactggccgg taaatcctga cagcatcatt    900
aacggcagtg acaataaaat tgcactggca gcacgccccg taaaagcgat tacgccccca    960
actcctgcag tacgcgcatc atgggtacat aaaacagggg cgaccggcgg atttggtagc   1020
tatgtcgcgt ttattccaga aaaagagctg ggtatcgtga tgctggcaaa caaaaactat   1080
cccaatccag cgagagtcga cgccgcctgg cagattctta acgctctaca gtaa         1134
```

<210> SEQ ID NO 5
<211> LENGTH: 377
<212> TYPE: PRT
<213> ORGANISM: Unknown Organism
<220> FEATURE:
<223> OTHER INFORMATION: Description of Unknown Organism: Escherichia coli plasmid pBR322

<400> SEQUENCE: 5

```
Met Val Lys Thr Thr Leu Cys Ala Leu Leu Ile Thr Ala Ser Cys Ser
  1               5                  10                  15

Thr Phe Ala Ala Pro Gln Gln Ile Asn Asp Ile Val His Arg Thr Ile
             20                  25                  30

Thr Pro Leu Ile Glu Gln Gln Lys Ile Pro Gly Met Ala Val Ala Val
         35                  40                  45

Ile Tyr Gln Gly Lys Pro Tyr Tyr Phe Thr Trp Gly Tyr Ala Asp Ile
     50                  55                  60

Ala Lys Lys Gln Pro Val Thr Gln Gln Thr Leu Phe Glu Leu Gly Ser
 65                  70                  75                  80

Val Ser Lys Thr Phe Thr Gly Val Leu Gly Gly Asp Ala Ile Ala Arg
                 85                  90                  95

Gly Glu Ile Lys Leu Ser Asp Pro Thr Thr Lys Tyr Trp Pro Glu Leu
            100                 105                 110

Thr Ala Lys Gln Trp Asn Gly Ile Thr Leu Leu His Leu Ala Thr Tyr
        115                 120                 125

Thr Ala Gly Gly Leu Pro Leu Gln Val Pro Asp Glu Val Lys Ser Ser
    130                 135                 140
```

-continued

```
Ser Asp Leu Leu Arg Phe Tyr Gln Asn Trp Gln Pro Ala Trp Ala Pro
145                 150                 155                 160

Gly Thr Gln Arg Leu Tyr Ala Asn Ser Ile Gly Leu Phe Gly Ala
            165                 170                 175

Leu Ala Val Lys Pro Ser Gly Leu Ser Phe Glu Gln Ala Met Gln Thr
        180                 185                 190

Arg Val Phe Gln Pro Leu Lys Leu Asn His Thr Trp Ile Asn Val Pro
        195                 200                 205

Pro Ala Glu Glu Lys Asn Tyr Ala Trp Gly Tyr Arg Glu Gly Lys Ala
        210                 215                 220

Val His Val Ser Pro Gly Ala Leu Asp Ala Glu Ala Tyr Gly Val Lys
225                 230                 235                 240

Ser Thr Ile Glu Asp Met Ala Arg Trp Val Gln Ser Asn Leu Lys Pro
                245                 250                 255

Leu Asp Ile Asn Glu Lys Thr Leu Gln Gln Gly Ile Gln Leu Ala Gln
            260                 265                 270

Ser Arg Tyr Trp Gln Thr Gly Asp Met Tyr Gln Gly Leu Gly Trp Glu
        275                 280                 285

Met Leu Asp Trp Pro Val Asn Pro Asp Ser Ile Ile Asn Gly Ser Asp
290                 295                 300

Asn Lys Ile Ala Leu Ala Ala Arg Pro Val Lys Ala Ile Thr Pro Pro
305                 310                 315                 320

Thr Pro Ala Val Arg Ala Ser Trp Val His Lys Thr Gly Ala Thr Gly
                325                 330                 335

Gly Phe Gly Ser Tyr Val Ala Phe Ile Pro Glu Lys Glu Leu Gly Ile
            340                 345                 350

Val Met Leu Ala Asn Lys Asn Tyr Pro Asn Pro Ala Arg Val Asp Ala
        355                 360                 365

Ala Trp Gln Ile Leu Asn Ala Leu Gln
        370                 375
```

<210> SEQ ID NO 6
<211> LENGTH: 1134
<212> TYPE: DNA
<213> ORGANISM: Artificial Sequence
<220> FEATURE:
<223> OTHER INFORMATION: Description of Artificial Sequence: mutant
      ampicillin resistance gene AmpC13A

<400> SEQUENCE: 6

| | | | | | | |
|---|---|---|---|---|---|---|
| atggtcaaaa | cgacgctctg | cgccctatta | attaccgcct | cttgctccac | atttgctgcc | 60 |
| cctcaacaaa | tcaacgatat | tgtgcatcgc | acaattaccc | cgcttataga | gcaacaaaag | 120 |
| atcccgggta | tggcggtggc | ggtaatttat | cagggtaaac | cttattactt | tacctggggc | 180 |
| tatgcggaca | tcgctaaaaa | gcagcccgtc | acacagcaaa | cgttgtttga | gttaggttcg | 240 |
| gtcagcaaaa | catttactgg | cgtgcttggt | ggcgacgcta | ttgctcgagg | ggaaatcaag | 300 |
| ttaagcgatc | ccacaacaaa | atactggcct | gaacttaccg | ctaaacagtg | aatgggatc | 360 |
| acactattac | atctcgcaac | ctacactgct | ggcggcctgc | cattgcaggt | gccggatgag | 420 |
| gtgaaatcct | caagcgactt | gctgcgcttc | tatcaaaact | ggcagcctgc | atgggctcca | 480 |
| ggaacacaac | gtctgtatgc | caactccagt | atcggtttgt | tcggcgcact | ggctgtgaag | 540 |
| ccgtctggtt | tgagttttga | gcaggcgatg | caaactcgtg | tyttccagcc | actcaaactc | 600 |
| aaccatacgt | ggattaatgt | accgcccgca | gaagaaaaga | attacgcctg | gggatatcgc | 660 |
| gaaggtaagg | cagtgcatgt | ttcgcctggg | gcgttagatg | ctgaagctta | tggtgtgaag | 720 |

-continued

```
tcgaccattg aagatatggc cgctggggtg caaagcaatt taaaacccct tgatatcaat    780
gagaaaacgc ttcaacaagg gatacaactg gcacaatctc gctactggca aaccggcgat    840
atgtatcagg gcctgggctg ggaaatgctg gactggccgg taaatcctga cagcatcatt    900
aacggccgtg acaataaaat tgcactggca gcacgccccg taaaagcgat tacgccccca    960
actcctgcag tacgcgcatc atgggtacat aaaacagggg cgaccggcgg atttggtagc   1020
tatgtcgcgt ttattccaga aaaagagctg ggtatcgtga tgctggcaaa caaaaactat   1080
cccaatccag cgagagtgga cgccgcctgg cagattctta acgctctaca gtaa          1134
```

<210> SEQ ID NO 7
<211> LENGTH: 377
<212> TYPE: PRT
<213> ORGANISM: Artificial Sequence
<220> FEATURE:
<223> OTHER INFORMATION: Description of Artificial Sequence: mutant ampicillin resistance protein AmpC13A

<400> SEQUENCE: 7

```
Met Val Lys Thr Thr Leu Cys Ala Leu Leu Ile Thr Ala Ser Cys Ser
 1               5                  10                  15

Thr Phe Ala Ala Pro Gln Gln Ile Asn Asp Ile Val His Arg Thr Ile
                20                  25                  30

Thr Pro Leu Ile Glu Gln Gln Lys Ile Pro Gly Met Ala Val Ala Val
            35                  40                  45

Ile Tyr Gln Gly Lys Pro Tyr Tyr Phe Thr Trp Gly Tyr Ala Asp Ile
         50                  55                  60

Ala Lys Lys Gln Pro Val Thr Gln Gln Thr Leu Phe Glu Leu Gly Ser
 65                  70                  75                  80

Val Ser Lys Thr Phe Thr Gly Val Leu Gly Gly Asp Ala Ile Ala Arg
                 85                  90                  95

Gly Glu Ile Lys Leu Ser Asp Pro Thr Thr Lys Tyr Trp Pro Glu Leu
            100                 105                 110

Thr Ala Lys Gln Trp Asn Gly Ile Thr Leu Leu His Leu Ala Thr Tyr
        115                 120                 125

Thr Ala Gly Gly Leu Pro Leu Gln Val Pro Asp Glu Val Lys Ser Ser
    130                 135                 140

Ser Asp Leu Leu Arg Phe Tyr Gln Asn Trp Gln Pro Ala Trp Ala Pro
145                 150                 155                 160

Gly Thr Gln Arg Leu Tyr Ala Asn Ser Ser Ile Gly Leu Phe Gly Ala
                165                 170                 175

Leu Ala Val Lys Pro Ser Gly Leu Ser Phe Glu Gln Ala Met Gln Thr
            180                 185                 190

Arg Val Phe Gln Pro Leu Lys Leu Asn His Thr Trp Ile Asn Val Pro
        195                 200                 205

Pro Ala Glu Glu Lys Asn Tyr Ala Trp Gly Tyr Arg Glu Gly Lys Ala
    210                 215                 220

Val His Val Ser Pro Gly Ala Leu Asp Ala Glu Ala Tyr Gly Val Lys
225                 230                 235                 240

Ser Thr Ile Glu Asp Met Ala Arg Trp Val Gln Ser Asn Leu Lys Pro
                245                 250                 255

Leu Asp Ile Asn Glu Lys Thr Leu Gln Gln Gly Ile Gln Leu Ala Gln
            260                 265                 270

Ser Arg Tyr Trp Gln Thr Gly Asp Met Tyr Gln Gly Leu Gly Trp Glu
        275                 280                 285
```

```
Met Leu Asp Trp Pro Val Asn Pro Asp Ser Ile Ile Asn Gly Arg Asp
    290                 295                 300
Asn Lys Ile Ala Leu Ala Ala Arg Pro Val Lys Ala Ile Thr Pro Pro
305                 310                 315                 320
Thr Pro Ala Val Arg Ala Ser Trp Val His Lys Thr Gly Ala Thr Gly
                325                 330                 335
Gly Phe Gly Ser Tyr Val Ala Phe Ile Pro Glu Lys Glu Leu Gly Ile
            340                 345                 350
Val Met Leu Ala Asn Lys Asn Tyr Pro Asn Pro Ala Arg Val Asp Ala
        355                 360                 365
Ala Trp Gln Ile Leu Asn Ala Leu Gln
    370                 375

<210> SEQ ID NO 8
<211> LENGTH: 1134
<212> TYPE: DNA
<213> ORGANISM: Artificial Sequence
<220> FEATURE:
<223> OTHER INFORMATION: Description of Artificial Sequence: mutant
      ampicillin resistance gene AmpC41A

<400> SEQUENCE: 8
atggtcaaaa cgacgctctg cgccctatta attaccgcct cttgctccac atttgctgcc      60
cctcaacaaa tcaacgatat tgtgcatcgc acaattaccc gcttataga gcaacaaaag      120
atcccgggta tggcggtggc ggtaatttat cagggtaaac cttattactt tacctggggc     180
tatgcggaca tcgctaaaaa gcagcccgtc acacagcaaa cgttgtttga gttaggttcg     240
gtcagcaaaa catttactgg cgtgcttggt ggcgacgcta ttgctcgagg ggaaatcaag     300
ttaagcgatc ccacaacaaa atactggcct gaacttaccg ctaaacagtg aatgggatc     360
tcactattac atctcgcaac ctacactgct ggcggcctgc cattgcaggt gccggatgag     420
gtgaaatcct caagcgactt gctgcgcttc tatcaaaact ggcagcctgc atgggctcca     480
ggaacacaac gtctgtatgc caactccagt atcggtttgt tcggcgcact ggctgtgaag     540
ccgtctggtt tgagttttga gcaggcgatg caaactcgtg tcttccagcc actcaaactc     600
aaccatacgt ggattaatgt accgccgca aagaaaaga attacgcctg gggatatcgc       660
gagggtaagg cagtgcatgt ttcgcctggg gcgttagatg ctgaagctta tggtgtgaag     720
tcgaccattg aagatatggc ccgctgggtg caaagcaatt taaaaccct tgatatcaat     780
gagaaaacgc ttcaacaagg gatacaactg gcacaatctc gctactggca aaccggcgat     840
atgtatcagg gcctgggctg ggaaatgctg gactggccgg taaatcctga cagcatcatt     900
aacggccgtg acaataaaat tgcactggca gcacgccccg taaaagcgat tacgccccca     960
actcctgcag tacgcgcatc atgggtacat aaaacagggg cgaccggcgg atttggtagc    1020
tatgtcgcgt ttattccaga aaaagagctg gtatcgtga tgctggcaaa caaaaactat     1080
cccaatccag cgagagtcga cgccgcctgg cagattctta acgccctaca gtaa           1134

<210> SEQ ID NO 9
<211> LENGTH: 377
<212> TYPE: PRT
<213> ORGANISM: Artificial Sequence
<220> FEATURE:
<223> OTHER INFORMATION: Description of Artificial Sequence: mutant
      ampicillin resistance protein AmpC41A

<400> SEQUENCE: 9
```

-continued

```
Met Val Lys Thr Thr Leu Cys Ala Leu Leu Ile Thr Ala Ser Cys Ser
 1               5                  10                  15

Thr Phe Ala Ala Pro Gln Gln Ile Asn Asp Ile Val His Arg Thr Ile
             20                  25                  30

Thr Pro Leu Ile Glu Gln Gln Lys Ile Pro Gly Met Ala Val Ala Val
         35                  40                  45

Ile Tyr Gln Gly Lys Pro Tyr Tyr Phe Thr Trp Gly Tyr Ala Asp Ile
     50                  55                  60

Ala Lys Lys Gln Pro Val Thr Gln Gln Thr Leu Phe Glu Leu Gly Ser
 65                  70                  75                  80

Val Ser Lys Thr Phe Thr Gly Val Leu Gly Gly Asp Ala Ile Ala Arg
                 85                  90                  95

Gly Glu Ile Lys Leu Ser Asp Pro Thr Thr Lys Tyr Trp Pro Glu Leu
            100                 105                 110

Thr Ala Lys Gln Trp Asn Gly Ile Ser Leu Leu His Leu Ala Thr Tyr
        115                 120                 125

Thr Ala Gly Gly Leu Pro Leu Gln Val Pro Asp Glu Val Lys Ser Ser
    130                 135                 140

Ser Asp Leu Leu Arg Phe Tyr Gln Asn Trp Gln Pro Ala Trp Ala Pro
145                 150                 155                 160

Gly Thr Gln Arg Leu Tyr Ala Asn Ser Ser Ile Gly Leu Phe Gly Ala
                165                 170                 175

Leu Ala Val Lys Pro Ser Gly Leu Ser Phe Glu Gln Ala Met Gln Thr
            180                 185                 190

Arg Val Phe Gln Pro Leu Lys Leu Asn His Thr Trp Ile Asn Val Pro
        195                 200                 205

Pro Ala Glu Glu Lys Asn Tyr Ala Trp Gly Tyr Arg Glu Gly Lys Ala
    210                 215                 220

Val His Val Ser Pro Gly Ala Leu Asp Ala Glu Ala Tyr Gly Val Lys
225                 230                 235                 240

Ser Thr Ile Glu Asp Met Ala Arg Trp Val Gln Ser Asn Leu Lys Pro
                245                 250                 255

Leu Asp Ile Asn Glu Lys Thr Leu Gln Gln Gly Ile Gln Leu Ala Gln
            260                 265                 270

Ser Arg Tyr Trp Gln Thr Gly Asp Met Tyr Gln Gly Leu Gly Trp Glu
        275                 280                 285

Met Leu Asp Trp Pro Val Asn Pro Asp Ser Ile Ile Asn Gly Arg Asp
    290                 295                 300

Asn Lys Ile Ala Leu Ala Ala Arg Pro Val Lys Ala Ile Thr Pro Pro
305                 310                 315                 320

Thr Pro Ala Val Arg Ala Ser Trp Val His Lys Thr Gly Ala Thr Gly
                325                 330                 335

Gly Phe Gly Ser Tyr Val Ala Phe Ile Pro Glu Lys Glu Leu Gly Ile
            340                 345                 350

Val Met Leu Ala Asn Lys Asn Tyr Pro Asn Pro Ala Arg Val Asp Ala
        355                 360                 365

Ala Trp Gln Ile Leu Asn Ala Leu Gln
    370                 375
```

<210> SEQ ID NO 10
<211> LENGTH: 1134
<212> TYPE: DNA
<213> ORGANISM: Artificial Sequence
<220> FEATURE:
<223> OTHER INFORMATION: Description of Artificial Sequence: mutant ampicillin resistance gene AmpC21B

<400> SEQUENCE: 10

```
atggtcaaaa cgacgctctg cgccttatta attaccgcct cttgctccac atttgctgcc    60
cctcaacaaa tcaacgatat tgtgcatcgc acaattaccc cgcttataga gcaacaaaag   120
atcccgggta tggcggtggc ggtaatttat cagggtaaac cttattactt tacctggggc   180
tatgcggaca tcgccaaaaa gcagcccgtc acacagcaaa cgttgtttga gttaggttcg   240
gtcagcaaaa catttactgg cgtgcttggt ggcgacgcta ttgctcgagg ggaaatcaag   300
ttaagcgatc ccacaacaaa atactggcct gaacttaccg ctaaacagtg gaatgggatc   360
acactattac atctcgcaac ctacactgct ggcggcctgc cattgcaggt gccggatgag   420
gtgaaatcct caagcgactt gctgcgcttc tatcaaaact ggcagcctgc atgggctcca   480
ggaacacaac gtctgtatgc caactccagt atcggtttgt tcggcgcact ggctgtgaag   540
ccgtctggtt tgagttttga gcaggcgatg caaactcgtg tcttccggcc actcaaactc   600
aaccatacgt ggattaatgt accgcccgca gaagaaaaga attaccgctg ggatatcgc    660
gaaggtaagg cagtgcatgt ttcgcctggg gcgttagatg ccgaagctta tggtgtgaag   720
tcgaccattg aagatatggc ccgctgggtg caaagcaatt taaaacccct tgatatcaat   780
gagaaaacgc ttcaacaagg gatacaactg gcacaatctc gctactggca aaccggcgat   840
atgtatcagg gcctgggctg ggaaatgcgg gactggccgg taagtcctga cagcatcatt   900
aacggcagtg acaataaaat tgcactggca gcacgccccg taaaagcgat tacgccccca   960
actcctgcag tacgcgcatc atgggtacat aaaacagggg cgaccggcgg atttggtagc  1020
tatgtcgcgt ttattccaga aaagagctg ggtatcgtga tgctggcaaa caaaaactat  1080
cccaatccag cgagagtcga cgccgcctgg cagattctta acgctctaca gtaa         1134
```

<210> SEQ ID NO 11
<211> LENGTH: 377
<212> TYPE: PRT
<213> ORGANISM: Artificial Sequence
<220> FEATURE:
<223> OTHER INFORMATION: Description of Artificial Sequence: mutant ampicillin resistance protein AmpC21B

<400> SEQUENCE: 11

```
Met Val Lys Thr Thr Leu Cys Ala Leu Leu Ile Thr Ala Ser Cys Ser
  1               5                  10                  15

Thr Phe Ala Ala Pro Gln Gln Ile Asn Asp Ile Val His Arg Thr Ile
             20                  25                  30

Thr Pro Leu Ile Glu Gln Gln Lys Ile Pro Gly Met Ala Val Ala Val
         35                  40                  45

Ile Tyr Gln Gly Lys Pro Tyr Tyr Phe Thr Trp Gly Tyr Ala Asp Ile
     50                  55                  60

Ala Lys Lys Gln Pro Val Thr Gln Gln Thr Leu Phe Glu Leu Gly Ser
 65                  70                  75                  80

Val Ser Lys Thr Phe Thr Gly Val Leu Gly Gly Asp Ala Ile Ala Arg
                 85                  90                  95

Gly Glu Ile Lys Leu Ser Asp Pro Thr Thr Lys Tyr Trp Pro Glu Leu
            100                 105                 110

Thr Ala Lys Gln Trp Asn Gly Ile Thr Leu Leu His Leu Ala Thr Tyr
        115                 120                 125

Thr Ala Gly Gly Leu Pro Leu Gln Val Pro Asp Glu Val Lys Ser Ser
    130                 135                 140
```

```
Ser Asp Leu Leu Arg Phe Tyr Gln Asn Trp Gln Pro Ala Trp Ala Pro
145                 150                 155                 160

Gly Thr Gln Arg Leu Tyr Ala Asn Ser Ser Ile Gly Leu Phe Gly Ala
                165                 170                 175

Leu Ala Val Lys Pro Ser Gly Leu Ser Phe Glu Gln Ala Met Gln Thr
            180                 185                 190

Arg Val Phe Arg Pro Leu Lys Leu Asn His Thr Trp Ile Asn Val Pro
        195                 200                 205

Pro Ala Glu Glu Lys Asn Tyr Ala Trp Gly Tyr Arg Glu Gly Lys Ala
    210                 215                 220

Val His Val Ser Pro Gly Ala Leu Asp Ala Glu Ala Tyr Gly Val Lys
225                 230                 235                 240

Ser Thr Ile Glu Asp Met Ala Arg Trp Val Gln Ser Asn Leu Lys Pro
                245                 250                 255

Leu Asp Ile Asn Glu Lys Thr Leu Gln Gln Gly Ile Gln Leu Ala Gln
                260                 265                 270

Ser Arg Tyr Trp Gln Thr Gly Asp Met Tyr Gln Gly Leu Gly Trp Glu
            275                 280                 285

Met Arg Asp Trp Pro Val Ser Pro Asp Ser Ile Ile Asn Gly Ser Asp
290                 295                 300

Asn Lys Ile Ala Leu Ala Ala Arg Pro Val Lys Ala Ile Thr Pro Pro
305                 310                 315                 320

Thr Pro Ala Val Arg Ala Ser Trp Val His Lys Thr Gly Ala Thr Gly
                325                 330                 335

Gly Phe Gly Ser Tyr Val Ala Phe Ile Pro Glu Lys Glu Leu Gly Ile
            340                 345                 350

Val Met Leu Ala Asn Lys Asn Tyr Pro Asn Pro Ala Arg Val Asp Ala
        355                 360                 365

Ala Trp Gln Ile Leu Asn Ala Leu Gln
    370                 375

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 12 gggggtggc catcatgttt gacagcttat catcg                              35

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 13
caggctgaaa atcttctctc atc                                          23

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 14
```

```
tcatccggct cgtataatgt gtgga                                              25

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:  primer

<400> SEQUENCE: 15
atcgcgtccg ccatctccag                                                    20

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence:  primer

<400> SEQUENCE: 16
aaaaccatgg tcaaaacgac gctct                                              25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence:  primer

<400> SEQUENCE: 17
gttgggtcct ggccactagt acttc                                              25
```